(12) United States Patent  (10) Patent No.: US 9,181,241 B2
Chen et al.  (45) Date of Patent: Nov. 10, 2015

(54) ANTAGONISTS OF CHEMOKINE RECEPTORS

(71) Applicant: ChemoCentryx, Inc., Mountain View, CA (US)

(72) Inventors: Xi Chen, Palo Alto, CA (US); Dean R. Dragoli, Los Altos, CA (US); Pingchen Fan, Fremont, CA (US); Yandong Li, San Jose, CA (US); Jay P. Powers, Pacifica, CA (US); Sreenivas Punna, Sunnyvale, CA (US); Hiroko Tanaka, Foster City, CA (US); Penglie Zhang, Foster City, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 150 days.

(21) Appl. No.: 14/011,174

(22) Filed: Aug. 27, 2013

(65) Prior Publication Data

US 2014/0057937 A1  Feb. 27, 2014

Related U.S. Application Data

(60) Provisional application No. 61/693,758, filed on Aug. 27, 2012, provisional application No. 61/831,694, filed on Jun. 6, 2013.

(51) Int. Cl.
  *C07D 471/04* (2006.01)
  *A61K 31/437* (2006.01)
  *A61K 45/06* (2006.01)
  *C07D 487/04* (2006.01)
  *C07D 491/052* (2006.01)
  *A61L 31/16* (2006.01)

(52) U.S. Cl.
  CPC ............ *C07D 471/04* (2013.01); *A61K 31/437* (2013.01); *A61K 45/06* (2013.01); *A61L 31/16* (2013.01); *C07D 487/04* (2013.01); *C07D 491/052* (2013.01); *A61L 2300/436* (2013.01)

(58) Field of Classification Search
  CPC ... A61K 31/437; A61K 45/06; C07D 471/04; C07D 487/04; A61L 2300/436; A61L 31/16
  See application file for complete search history.

(56) References Cited

U.S. PATENT DOCUMENTS

2007/0088036 A1  4/2007  Zhang et al.

FOREIGN PATENT DOCUMENTS

WO  2012/087782 A1  6/2012

OTHER PUBLICATIONS

International Search Report corresponding to PCT/US2013/056796, mailed Jan. 10, 2014 (3 pages).

*Primary Examiner* — Kendra D Carter
(74) *Attorney, Agent, or Firm* — Kilpatrick Townsend & Stockton LLP; William B. Kezer

(57) ABSTRACT

Compounds are provided that act as potent antagonists of the CCR1 receptor, and have in vivo anti-inflammatory activity. The compounds are generally aryl piperazine derivatives and are useful in pharmaceutical compositions, methods for the treatment of CCR1-mediated diseases, and as controls in assays for the identification of competitive CCR1 antagonists.

19 Claims, No Drawings

ANTAGONISTS OF CHEMOKINE RECEPTORS

CROSS-REFERENCES TO RELATED APPLICATIONS

This application claims the benefit of priority to U.S. Application Ser. Nos. 61/693,758, filed Aug. 27, 2012, and 61/831,694, filed Jun. 6, 2013, the disclosures of which are incorporated herein by reference in their entirety.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The present invention provides compounds, pharmaceutical compositions containing one or more of those compounds or their pharmaceutically acceptable salts, which are effective in inhibiting the binding of various chemokines, such as MIP-1α, leukotactin, MPIF-1 and RANTES, to the CCR1 receptor. As antagonists or modulators for the CCR1 receptor, the compounds and compositions have utility in treating inflammatory and immune disorder conditions and diseases.

Human health depends on the body's ability to detect and destroy foreign pathogens that might otherwise take valuable resources from the individual and/or induce illness. The immune system, which comprises leukocytes (white blood cells (WBCs): T and B lymphocytes, monocytes, macrophages granulocytes, NK cell, mast cells, dendritic cell, and immune derived cells (for example, osteoclasts)), lymphoid tissues and lymphoid vessels, is the body's defense system. To combat infection, white blood cells circulate throughout the body to detect pathogens. Once a pathogen is detected, innate immune cells and cytotoxic T cells in particular are recruited to the infection site to destroy the pathogen. Chemokines act as molecular beacons for the recruitment and activation of immune cells, such as lymphocytes, monocytes and granulocytes, identifying sites where pathogens exist.

Despite the immune system's regulation of pathogens, certain inappropriate chemokine signaling can develop and has been attributed to triggering or sustaining inflammatory disorders, such as rheumatoid arthritis, multiple sclerosis and others. For example, in rheumatoid arthritis, unregulated chemokine accumulation in bone joints attracts and activates infiltrating macrophages and T-cells. The activities of these cells induce synovial cell proliferation that leads, at least in part, to inflammation and eventual bone and cartilage loss (see, DeVries, M. E., et al., *Semin Immunol* 11(2): 95-104 (1999)). A hallmark of some demyelinating diseases such as multiple sclerosis is the chemokine-mediated monocyte/macrophage and T cell recruitment to the central nervous system (see, Kennedy, et al., *J. Clin. Immunol.* 19(5):273-279 (1999)). Chemokine recruitment of destructive WBCs to transplants has been implicated in their subsequent rejection. See, DeVries, M. E., et al., ibid. Because chemokines play pivotal roles in inflammation and lymphocyte development, the ability to specifically manipulate their activity has enormous impact on ameliorating and halting diseases that currently have no satisfactory treatment. In addition, transplant rejection may be minimized without the generalized and complicating effects of costly immunosuppressive pharmaceuticals.

Chemokines, a group of greater than 40 small peptides (7-10 kD), ligate receptors expressed primarily on WBCs or immune derived cells, and signal through G-protein-coupled signaling cascades to mediate their chemoattractant and chemostimulant functions. Receptors may bind more than one ligand; for example, the receptor CCR1 ligates RANTES (regulated on activation normal T cell expressed), MIP-1α (macrophage inflammatory protein), MPIF-1/CKβ8, and Leukotactin chemokines (among others with lesser affinities). To date, 24 chemokine receptors are known. The sheer number of chemokines, multiple ligand binding receptors, and different receptor profiles on immune cells allow for tightly controlled and specific immune responses. See, Rossi, et al., *Ann. Rev. Immunol.* 18(1):217-242 (2000). Chemokine activity can be controlled through the modulation of their corresponding receptors, treating related inflammatory and immunological diseases and enabling organ and tissue transplants.

The receptor CCR1 and its chemokine ligands, including, for example MIP-1α, MPIF-1/CKβ8, leukotactin and RANTES, represent significant therapeutic targets (see Saeki, et al., *Current Pharmaceutical Design* 9:1201-1208 (2003)) since they have been implicated in rheumatoid arthritis, transplant rejection (see, DeVries, M. E., et al., ibid.), and multiple sclerosis (see, Fischer, et al., *J Neuroimmunol.* 110 (1-2):195-208 (2000); Izikson, et al., *J. Exp. Med.* 192(7): 1075-1080 (2000); and Rottman, et al., *Eur. J. Immunol.* 30(8):2372-2377 (2000). In fact, function-blocking antibodies, modified chemokine receptor ligands and small organic compounds have been discovered, some of which have been successfully demonstrated to prevent or treat some chemokine-mediated diseases (reviewed in Rossi, et al., ibid.). Notably, in an experimental model of rheumatoid arthritis, disease development is diminished when a signaling-blocking, modified-RANTES ligand is administered (see Plater-Zyberk, et al., *Immunol Lett.* 57(1-3):117-120 (1997)). While function-blocking antibody and small peptide therapies are promising, they suffer from the perils of degradation, extremely short half-lives once administered, and prohibitive expense to develop and manufacture, characteristic of most proteins. Small organic compounds are preferable since they often have longer half lives in vivo, require fewer doses to be effective, can often be administered orally, and are consequently less expensive. Some organic antagonists of CCR1 have been previously described (see, Hesselgesser, et al., *J. Biol. Chem.* 273(25):15687-15692 (1998); Ng, et al., *J. Med. Chem.* 42(22):4680-4694 (1999); Liang, et al., *J. Biol. Chem.* 275(25):19000-19008 (2000); and Liang, et al., *Eur. J. Pharmacol.* 389(1):41-49 (2000)). In view of the effectiveness demonstrated for treatment of disease in animal models (see, Liang, et al., *J. Biol. Chem.* 275(25):19000-19008 (2000)), the search has continued to identify additional compounds that can be used in the treatment of diseases mediated by CCR1 signaling.

BRIEF SUMMARY OF THE INVENTION

Described herein are compounds having the formula:

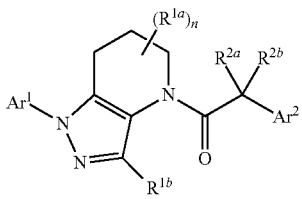
(I)

and salts, rotamers and optical isomers thereof, wherein the subscript n, and the substituents $R^{1a}$, $R^{1b}$, $R^{2a}$, $R^{2b}$, $Ar^1$ and $Ar^2$ have the meanings provided in the description and claims.

Selected groups of compounds are those of formulae Ia, Ia1, Ia2, II, III and IV:

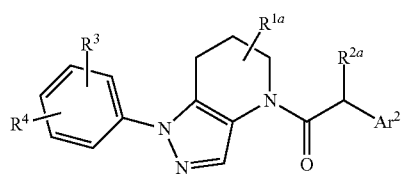
(Ia)

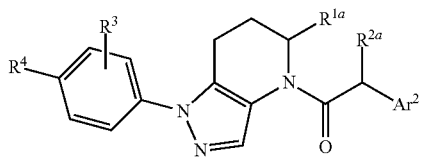
(Ia1)

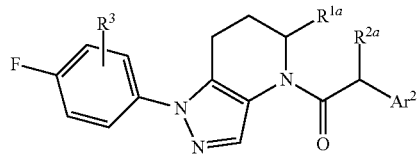
(Ia2)

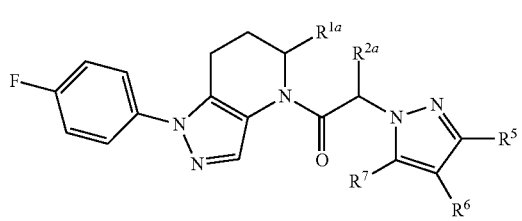
(II)

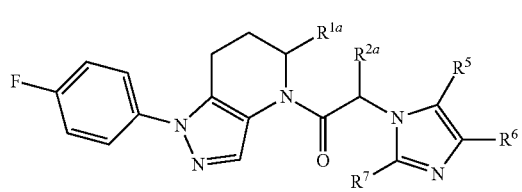
(III)

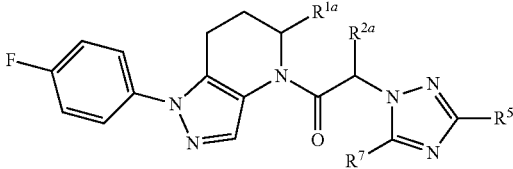
(IV)

In addition to the compounds provided herein, the present invention further provides pharmaceutical compositions containing one or more of these compounds, as well as methods for the use of these compounds in therapeutic methods, primarily to treat diseases associated with CCR1 signaling activity.

BRIEF DESCRIPTION OF THE DRAWINGS

None

DETAILED DESCRIPTION OF THE INVENTION

I. Abbreviation and Definitions

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycyclic ring system. Non limiting examples of heterocycloalkyl groups include pyrrolidine, piperidinyl, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-5-oxide, thiomorpholine-S,S-oxide, piperazine, pyran, pyridone, 3-pyrroline, thiopyran, pyrone, tetrahydrofuran, tetrahydrothiophene, quinuclidine, and the like. A heterocycloalkyl group can be attached to the remainder of the molecule through a ring carbon or a heteroatom.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene"

is a shorter chain alkyl or alkylene group, generally having four or fewer carbon atoms. Similarly, "alkenylene" and "alkynylene" refer to the unsaturated forms of "alkylene" having double or triple bonds, respectively.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —NR$^a$R$^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like).

The above terms (e.g., "alkyl," "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below, while the term "alkyl" and related aliphatic radicals is meant to refer to unsubstituted version, unless indicated to be substituted.

Substituents for the alkyl radicals (including those groups often referred to as alkylene, alkenyl, alkynyl and cycloalkyl) can be a variety of groups selected from: -halogen, —OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)═NH, —NR'C(NH$_2$)═NH, —NH—C(NH$_2$)═NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R'" each independently refer to hydrogen, unsubstituted $C_{1-8}$ alkyl, unsubstituted heteroalkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)═NH, —NR'C(NH$_2$)═NH, —NH—C(NH$_2$)═NR', —S(O)R', —S(O)$_2$R', —S(O)$_2$NR'R", —NR'S(O)$_2$R", —N$_3$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, $C_{1-8}$ alkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

II. General

The present invention derives from the discovery that compounds of formula I (as well as the subgeneric formulae Ia, Ia1, Ia2, II, III and IV) act as potent antagonists of the CCR1 receptor. The compounds have in vivo anti-inflammatory activity. Accordingly, the compounds provided herein are useful in pharmaceutical compositions, methods for the treatment of CCR1-mediated diseases, and as controls in assays for the identification of competitive CCR1 antagonists.

III. Compounds

In one aspect, the present invention provides compounds having the formula:

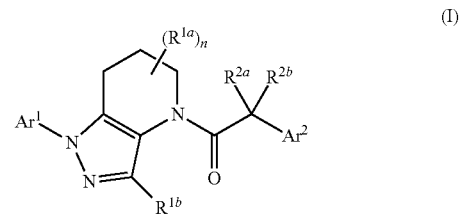

(I)

and salts, rotamers and optical isomers thereof.

In formula I, the subscript n is an integer of from 0 to 3; each $R^{1a}$ and $R^{1b}$ is a member independently selected from the group consisting of H, $C_{1-8}$ alkyl, $C_{1-8}$ haloalkyl, $C_{3-6}$ cycloalkyl, —$COR^a$, —$CO_2R^a$, —$CONR^aR^b$, —$NR^aCOR^b$, —$OR^a$, —$X^1COR^a$, —$X^1CO_2R^a$, —$X^1CONR^aR^b$, $X^1NR^aCOR^b$, —$X^1NR^aR^b$, and —$X^1OR^a$, wherein $X^1$ is a member selected from the group consisting of $C_{1-4}$ alkylene, and each $R^a$ and $R^b$ is independently selected from the group consisting of hydrogen, $C_{1-8}$ alkyl, $C_{1-8}$ haloalkyl, and $C_{3-6}$ cycloalkyl, and optionally two $R^{1a}$ groups on adjacent carbon atoms are joined to form a 5-, 6- or 7-membered carbocyclic or heterocyclic ring; each of $R^{2a}$ and $R^{2b}$ is a member independently selected from the group consisting of H, hydroxyl, $C_{1-8}$ alkyl, $C_{1-8}$ haloalkyl, $C_{1-8}$ alkoxy, $C_{1-4}$ alkoxy-$C_{1-4}$ alkyl, $C_{1-8}$ hydroxyalkyl, $C_{1-4}$ alkoxy-$C_{1-4}$ alkoxy, $C_{3-6}$ cycloalkyl, $C_{3-6}$ cycloalkyl-$C_{1-4}$ alkyl, 3- to 7-membered heterocycloalkyl, 3- to 7-membered heterocycloalkyl-$C_{1-4}$ alkyl, —$X^1CO_2R^a$, —$X^1CONR^aR^b$, —$X^1NR^aCOR^b$, —$X^1NR^aR^b$, wherein $X^1$, $R^a$ and $R^b$ are defined above.

The symbol $Ar^1$ represents a six- or ten-membered monocyclic or fused bicyclic aryl ring, or a five- to ten-membered monocyclic or fused bicyclic heteroaryl ring; each of which is substituted with from one to five substituents, $R^3$, $R^{3a}$, $R^{3b}$, $R^4$ and $R^{4a}$ which are independently selected from the group consisting of H, halogen, —$OR^c$, —$OC(O)R^c$, —$NR^cR^d$, —$SR^c$, —$R^e$, —$CN$, —$NO_2$, —$CO_2R^c$, —$CONR^cR^d$, —$C(O)R^c$, —$OC(O)NR^cR^d$, —$NR^dC(O)R^c$, —$NR^dC(O)_2R^e$, —$NR^c$—$C(O)NR^cR^d$, —$NH$—$C(NH_2)$=$NH$, —$NR^eC(NH_2)$=$NH$, —$NH$—$C(NH_2)$=$NR^e$, —$NH$—$C(NHR^e)$=$NH$, —$S(O)R^e$, —$S(O)_2R^e$, —$NR^cS(O)_2R^e$, —$S(O)_2NR^cR^d$, —$N_3$, —$X^2OR^c$, —$O$—$X^2OR^c$, —$X^2OC(O)R^c$, —$X^2NR^cR^d$, —$O$—$X^2NR^cR^d$, —$X^2SR^c$, —$X^2CN$, —$X^2NO_2$, —$X^2CO_2R^c$, —$O$—$X^2CO_2R^c$, —$X^2CONR^cR^d$, —$O$—$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^cR^d$, —$X^2NH$—$C(NH_2)$=$NH$, —$X^2NR^eC(NH_2)$=$NH$, —$X^2NH$—$C(NH_2)$=$NR^e$, —$X^2NH$—$C(NHR^e)$=$NH$, —$X^2S(O)R^e$, —$X^2S(O)_2R^e$, —$X^2NR^cS(O)_2R^e$, —$X^2S(O)_2NR^cR^d$, —$X^2N_3$, —$NR^d$—$X^2OR^c$, —$NR^d$—$X^2NR^cR^d$, —NR$^d$—X$^2$CO$_2$R$^c$, and —NR$^d$—X$^2$CONR$^c$R$^d$, wherein each X$^2$ is a member independently selected from the group consisting of C$_{1-4}$ alkylene, and each R$^c$ and R$^d$ is independently selected from hydrogen, C$_{1-8}$ alkyl, C$_{1-8}$ hydroxyalkyl, C$_{1-8}$ haloalkyl and C$_{3-6}$ cycloalkyl, or optionally R$^c$ and R$^d$ when attached to the same nitrogen atom can be combined with the nitrogen atom to form a five or six-membered ring having from 0 to 2 additional heteroatoms as ring members; and each R$^e$ is independently selected from the group consisting of C$_{1-8}$ alkyl, C$_{1-8}$ hydroxyalkyl, C$_{1-8}$ haloalkyl and C$_{3-6}$ cycloalkyl.

The symbol Ar$^2$ represents a six- or ten-membered monocyclic or fused bicyclic aryl ring, or a five- to ten-membered monocyclic or fused bicyclic heteroaryl ring; each of which is substituted with from one to five substituents, R$^5$, R$^6$, R$^7$, R$^8$ and R$^9$, independently selected from the group consisting of H, halogen, —OR$^f$, —OC(O)R$^f$, —NR$^f$R$^g$, —SR$^f$, —R$^h$, —CN, —NO$_2$, —CO$_2$R$^f$, —CONR$^f$R$^g$, —C(O)R$^f$, —OC(O)NR$^f$R$^g$, —NR$^g$C(O)R$^f$, —NR$^g$C(O)$_2$R$^h$, —NR$^f$—C(O)NR$^f$R$^g$, —NH—C(NH$_2$)—NH, —NR$^h$C(NH$_2$)—NH, —NH—C(NH$_2$)—NR$^h$, —NH—C(NHR$^h$)—NH, —S(O)R$^h$, —S(O)$_2$R$^h$, —NR$^f$S(O)$_2$R$^h$, —S(O)$_2$NR$^f$R$^g$, —NR$^f$S(O)$_2$NR$^f$R$^g$, —N$_3$, —X$^3$OR$^f$, —X$^3$OC(O)R$^f$, —X$^3$NR$^f$R$^g$, —X$^3$SR$^f$, —X$^3$CN, —X$^3$NO$_2$, —X$^3$CO$_2$R$^f$, —X$^3$CONR$^f$R$^g$, —X$^3$C(O)R$^f$, —X$^3$OC(O)NR$^f$R$^g$, —X$^3$NR$^g$C(O)R$^f$, —X$^3$NR$^g$C(O)$_2$R$^h$, —X$^3$NR$^f$—C(O)NR$^f$R$^g$, —X$^3$NH—C(NH$_2$)—NH, —X$^3$NR$^h$C(NH$_2$)—NH, —X$^3$NH—C(NH$_2$)—NR$^h$, —X$^3$NH—C(NHR$^h$)—NH, —X$^3$S(O)R$^h$, —X$^3$S(O)$_2$R$^h$, —X$^3$NR$^f$S(O)$_2$R$^h$, —X$^3$S(O)$_2$NR$^f$R$^g$, —Y, —X$^3$Y, —S(O)$_2$Y, —C(O)Y, —X$^3$N$_3$, —O—X$^3$OR$^f$, —O—X$^3$NR$^f$R$^g$, —O—X$^3$CO$_2$R$^f$, —O—X$^3$CONR$^f$R$^g$, —NR$^g$—X$^3$OR$^f$, —NR$^g$—X$^3$NR$^f$R$^g$, —NR$^g$—X$^3$CO$_2$R$^f$, and —NR$^g$—X$^3$CONR$^f$R$^g$, wherein Y is a five or six- membered aryl, heteroaryl or heterocyclic ring, optionally substituted with from one to three substitutents selected from the group consisting of halogen, —OR$^f$, —OC(O)R$^f$, —NR$^f$R$^g$, —R$^h$, —SR$^f$, —CN, —NO$_2$, —CO$_2$R$^f$, —CONR$^f$R$^g$, —C(O)R$^f$, —NR$^g$C(O)R$^f$, —NR$^g$C(O)$_2$R$^h$, —S(O)R$^h$, —S(O)$_2$R$^h$, —NR$^f$S(O)$_2$R$^h$, —S(O)$_2$NR$^f$R$^g$, —X$^3$OR$^f$, X$^3$SR$^f$, —X$^3$CN, —X$^3$NO$_2$, —X$^3$CO$_2$R$^f$, —X$^3$CONR$^f$R$^g$, —X$^3$C(O)R$^f$, —X$^3$OC(O)NR$^f$R$^g$, —X$^3$NR$^g$C(O)R$^f$, —X$^3$NR$^g$C(O)$_2$R$^h$, —X$^3$NR$^f$—C(O)NR$^f$R$^g$, —X$^3$OC(O)R$^f$, —X$^3$S(O)R$^h$, —X$^3$S(O)$_2$R$^h$, —X$^3$NR$^f$R$^g$, —X$^3$NR$^f$S(O)$_2$R$^h$, —X$^3$S(O)$_2$NR$^f$R$^g$, —O—X$^3$OR$^f$, —O—X$^3$NR$^f$R$^g$, —O—X$^3$CO$_2$R$^f$, —O—X$^3$CONR$^f$R$^g$, —NR$^g$—X$^3$OR$^f$, —NR$^g$—X$^3$NR$^f$R$^g$, —NR$^g$—X$^3$CO$_2$R$^f$, and —NR$^g$—X$^3$CONR$^f$R$^g$ and wherein each X$^3$ is independently selected from the group consisting of C$_{1-4}$ alkylene, and each R$^f$ and R$^g$ is independently selected from hydrogen, C$_{1-8}$ alkyl, C$_{1-8}$ hydroxyalkyl, C$_{1-8}$ haloalkyl and C$_{3-6}$ cycloalkyl, or when attached to the same nitrogen atom can be combined with the nitrogen atom to form a five or six-membered ring having from 0 to 2 additional heteroatoms as ring members, and each R$^h$ is independently selected from the group consisting of C$_{1-8}$ alkyl, C$_{2-8}$ alkenyl, C$_{2-8}$ alkynyl, C$_{1-8}$ hydroxyalkyl, C$_{1-8}$ haloalkyl and C$_{3-6}$ cycloalkyl; or when two of R$^5$, R$^6$, R$^7$, R$^8$ and R$^9$, are attached to adjacent ring vertices of Ar$^2$, are optionally combined to form a five or six membered ring having zero, one or two heteroatoms selected from O and N as ring members.

In some embodiments, the compounds of formula I are those in which Ar$^1$ is selected from the group consisting of phenyl, naphthyl, pyridyl, pyrazinyl, pyridazinyl, pyrimidinyl, triazinyl, quinolinyl, quinoxalinyl and purinyl, each of which is optionally substituted with R$^3$, R$^{3a}$, R$^{3b}$, R$^4$ and R$^{4a}$.

In other embodiments, the compounds of formula I are those in which Ar$^1$ is selected from the group consisting of phenyl, naphthyl and pyridyl, each of which is optionally substituted with R$^3$, R$^{3a}$, R$^{3b}$, R$^4$ and R$^{4a}$.

In still other embodiments, the compounds of formula I are those in which Ar$^2$ is selected from the group consisting of phenyl, pyrazolyl, imidazolyl, triazolyl, tetrazolyl, oxazolyl, isoxazolyl, oxadiazolyl, oxathiadiazolyl, pyrrolyl, thiazolyl, isothiazolyl, benzimidazolyl, benzoxazolyl, benzopyrazolyl, benzotriazolyl, pyrazolo[3,4-b]pyridine, pyrazolo[3,4-d]pyrimidine, imidazo[4,5-b]pyridine, imidazo[1,5-a]pyridine, and pyrrolo[2,3-b]pyridine, each of which is optionally substituted with R$^5$, R$^6$ and R$^7$.

In yet other embodiments, the compounds of formula I are those in which Ar$^2$ is selected from the group consisting of pyrazolyl, imidazolyl and triazolyl, each of which is substituted with R$^5$, R$^6$ and R$^7$.

In certain embodiments, the compounds of formula I are those in which Ar$^1$ is selected from the group consisting of phenyl, naphthyl and pyridyl, each of which is substituted with from one to five substituents, R$^3$, R$^{3a}$, R$^{3b}$, R$^4$ and R$^{4a}$; and Ar$^2$ is selected from the group consisting of pyrazolyl, imidazolyl and triazolyl, each of which is substituted with R$^5$, R$^6$ and R$^7$.

In selected embodiments, the compounds of formula I are those in which Ar$^1$ is phenyl, which is substituted with from one to five substituents, R$^3$, R$^{3a}$, R$^{3b}$, R$^4$ and R$^{4a}$, and Ar$^2$ is selected from the group consisting of pyrazolyl, imidazolyl, benzimidazolyl, benzopyrazolyl, pyrazolo[3,4-b]pyridine, pyrazolo[3,4-d]pyrimidine, imidazo[4,5-b]pyridine, imidazo[1,5-a]pyridine, and pyrrolo[2,3-b]pyridine, each of which is optionally substituted with R$^5$, R$^6$ and R$^7$.

Still other embodiments of the invention are the compounds of formulae Ia, Ia1, Ia2, II, III and IV.

Accordingly, in some embodiments, the compounds are those of formula Ia:

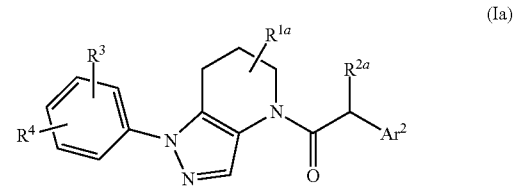

(Ia)

or a pharmaceutically acceptable salt, rotamer or optical isomer thereof, wherein R$^3$ and R$^4$ are independently selected from the group consisting of H, halogen, —R$^e$, —CN, and —SO$_2$R$^e$; and the groups R$^{1a}$, R$^{2a}$ and Ar$^2$ have the meanings provided with reference to formula I above, or the other embodiments provided.

In still other embodiments of formula I or Ia, Ar$^2$ is a heteroaryl group; in other embodiments, Ar$^2$ is a heteroaryl group, optionally substituted and attached to the remainder of the molecule through a nitrogen atom ring vertex; and in still other embodiments, Ar$^2$ has the formula:

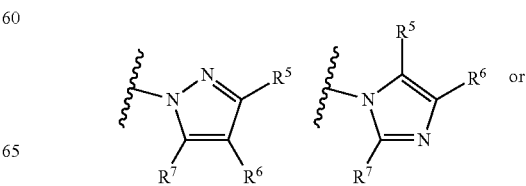

-continued

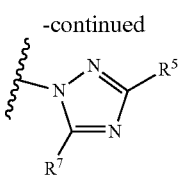

wherein $R^5$, $R^6$, and $R^7$ are independently selected from the group consisting of H, halogen, —$R^h$, —CN, —$SO_2R^h$, —$CO_2R^f$, —$CONR^fR^g$, and Y, wherein —$R^h$, $R^f$, $R^g$, and Y have the meanings provided above with respect to formula I.

In one group of selected embodiments, the compounds have the formula:

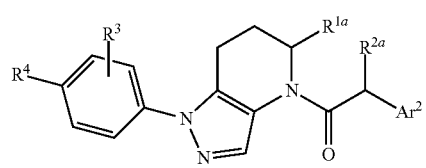

(Ia1)

or a pharmaceutically acceptable salt, rotamer or optical isomer thereof, wherein $R^4$ is selected from the group consisting of F and Cl; and the groups $R^{1a}$, $R^{2a}$, $R^3$ and $Ar^2$ have the meanings provided with reference to formula I or Ia above, or the other embodiments provided.

In another group of selected embodiments, the compounds have the formula:

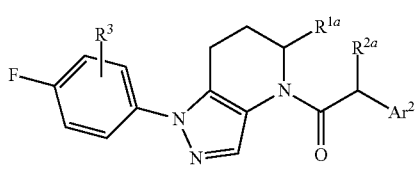

(Ia2)

or a pharmaceutically acceptable salt, rotamer or optical isomer thereof, wherein $R^3$ is selected from the group consisting of H, halogen, $C_{1-8}$ alkyl, $C_{1-8}$ haloalkyl and $C_{1-8}$ alkoxy; $R^{1a}$ and $R^{2a}$ are independently selected from the group consisting of H, $C_{1-8}$ alkyl, $C_{1-8}$ haloalkyl, $C_{1-8}$ alkoxy and $C_{1-8}$ hydroxyalkyl; and $Ar^2$ has the meaning provided with reference to formula I or Ia above, or the embodiments provided.

In yet another group of selected embodiments, the compounds have the formula:

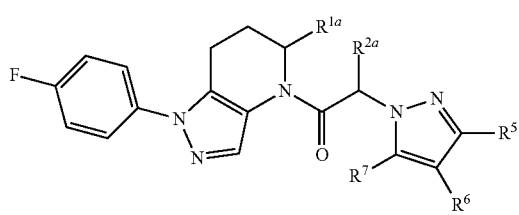

(II)

or a pharmaceutically acceptable salt, rotamer or optical isomer thereof, wherein $R^{1a}$ and $R^{2a}$ are independently selected from the group consisting of H, $C_{1-8}$ alkyl, $C_{1-8}$ haloalkyl, $C_{1-8}$ alkoxy and $C_{1-8}$ hydroxyalkyl; and $R^5$, $R^6$, and $R^7$ are independently selected from the group consisting of H, halogen, —$R^h$, —CN, —$SO_2R^h$, —$CO_2R^f$, —$CONR^fR^g$, and Y; wherein —$R^h$, $R^f$, $R^g$, and Y have the meanings provided above with respect to formula I.

In still another group of selected embodiments, the compounds have the formula:

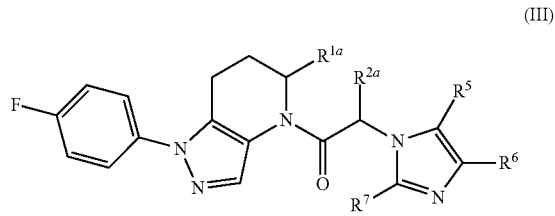

(III)

or a pharmaceutically acceptable salt, rotamer or optical isomer thereof, wherein $R^{1a}$ and $R^{2a}$ are independently selected from the group consisting of H, $C_{1-8}$ alkyl, $C_{1-8}$ haloalkyl, $C_{1-8}$ alkoxy and $C_{1-8}$ hydroxyalkyl; and $R^5$, $R^6$, and $R^7$ are independently selected from the group consisting of H, halogen, —$R^h$, —CN, —$SO_2R^h$, —$CO_2R^f$, —$CONR^fR^g$, and Y; wherein —$R^h$, $R^f$, $R^g$, and Y have the meanings provided above with respect to formula I.

In another group of selected embodiments, the compounds have the formula:

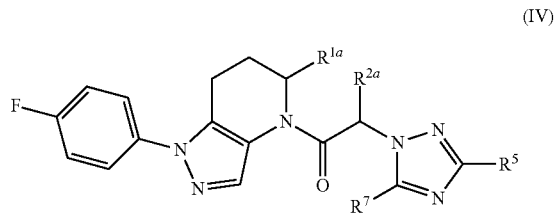

(IV)

or a pharmaceutically acceptable salt, rotamer or optical isomer thereof, wherein $R^{1a}$ and $R^{2a}$ are each independently selected from the group consisting of H, $C_{1-8}$ alkyl, $C_{1-8}$ haloalkyl, $C_{1-8}$ alkoxy, and $C_{1-8}$ hydroxyalkyl; and $R^5$ and $R^7$ are each independently selected from the group consisting of H, halogen, —$R^h$, —CN, —$SO_2R^h$, —$CO_2R^f$, —$CONR^fR^g$, and Y; wherein —$R^h$, $R^f$, $R^g$, and Y have the meanings provided above with respect to formula I.

For any of the embodiments above, when Y is present, selected embodiments are those in which Y is selected from the group consisting of pyridyl, pyrimidinyl, imidazolyl, oxazolyl, oxadiazolyl, triazolyl, thiazolyl, imidazolinyl and pyrazolyl.

Specific compounds of particular interest are those provided in Table 1, along with their pharmaceutically acceptable salts, hydrates or N-oxides, rotamers, and stereoisomers thereof.

Preparation of Compounds

As provided in the examples below, the compounds and intermediates of the present invention can be prepared by one of skill in the art in a component assembly manner.

IV. Pharmaceutical Compositions

In addition to the compounds provided above, compositions for modulating CCR1 activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of this invention may also be coupled to a carrier that is a suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the invention may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like. In one embodiment of the invention, the compound of the invention is coupled to a polymer or semipermeable polymer matrix that is formed as a stent or stent-graft device.

V. Methods of Treating Diseases Modulated by CCR1

In yet another aspect, the present invention provides methods of treating CCR1-mediated conditions or diseases by administering to a subject having such a disease or condition, a therapeutically effective amount of a compound of formula I above. The "subject" is defined herein to include animals such as mammals, including, but not limited to, primates (e.g., humans), cows, sheep, goats, horses, dogs, cats, rabbits, rats, mice and the like.

CCR1 provides a target for interfering with or promoting specific aspects of immune cell functions, or more generally, with functions associated with CCR1 expression on a wide range of cell types in a mammal, such as a human. Compounds that inhibit CCR1, are particularly useful for modulating monocyte, macrophage, lymphocyte, granulocyte, NK cell, mast cells, dendritic cell, neutrophils, and certain immune derived cell (for example, osteoclasts) function for therapeutic purposes. Accordingly, the present invention is directed to compounds which are useful in the prevention and/or treatment of a wide variety of inflammatory and immunoregulatory disorders and diseases (see Saeki, et al., *Current Pharmaceutical Design* 9:1201-1208 (2003)).

For example, an instant compound that inhibits one or more functions of CCR1 may be administered to inhibit (i.e., reduce or prevent) inflammation or cellular infiltration associated with an immune disorder. As a result, one or more inflammatory processes, such as leukocyte emigration or infiltration, chemotaxis, exocytosis (e.g., of enzymes, histamine) or inflammatory mediator release, can be inhibited. For example, monocyte infiltration to an inflammatory site (e.g., an affected joint in arthritis, or into the CNS in MS) can be inhibited according to the present method.

Similarly, an instant compound that promotes one or more functions of CCR1 is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, monocytes can be recruited to combat bacterial infections.

Diseases and conditions associated with inflammation, immune disorders and infection can be treated using the method of the present invention. In a preferred embodiment, the disease or condition is one in which the actions of immune cells such monocyte, macrophage, lymphocyte, granulocyte, NK cell, mast cell, dendritic cell, or certain immune derived cell (for example, osteoclasts) are to be inhibited or promoted, in order to modulate the inflammatory or autoimmune response.

In one group of embodiments, diseases or conditions, including chronic diseases, of humans or other species can treated with modulators of CCR1 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as allergic asthma, allergic rhinitis, hypersensitivity lung diseases and the like, (9) autoimmune diseases, such as fibromyalgia, scleroderma, ankylosing spondylitis, juvenile RA, Still's disease, polyarticular juvenile RA, pauciarticular juvenile RA, polymyalgia rheumatica, rheumatoid arthritis, psoriatic arthritis, osteoarthritis, polyarticular arthritis, multiple sclerosis, systemic lupus erythematosus, type I diabetes, type II diabetes, glomerulonephritis, and the like, (10) graft rejection (including allograft rejection and graft-v-host disease), and (11) other diseases in which undesired inflammatory responses or immune disorders are to be inhibited, such as cardiovascular disease including atherosclerosis and restenosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout, (12) osteoporosis and other disorders of the bone (13) immune mediated food allergies such as Celiac disease and (14) radiation-induced pulmonary disease (RIPD). See eg Yang et al, Am J Respir Cell Mol Biol. 45(1):127-35 (2011).

In another group of embodiments, diseases or conditions can be treated with modulators of CCR1 function. Examples of diseases to be treated with modulators of CCR1 function include cancers such as multiple myeloma and related osteolytic bone disease, cardiovascular diseases, diseases in which angiogenesis or neovascularization play a role (neoplastic diseases, retinopathy and macular degeneration), infectious diseases (viral infections, e.g., HIV and RSV infection, and bacterial infections) and immunosuppressive diseases such as organ transplant conditions and skin transplant conditions. The term "organ transplant conditions" is meant to include bone marrow transplant conditions and solid organ (e.g., kidney, liver, lung, heart, pancreas or combination thereof) transplant conditions.

The compounds of the present invention are accordingly useful in the prevention and treatment of a wide variety of inflammatory and immunoregulatory disorders and diseases.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection, or implant), by implantation (e.g., as when the compound is coupled to a stent device), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

Diseases and conditions associated with inflammation, immune disorder, infection and cancer can be treated or prevented with the present compounds, compositions, and methods.

The compounds and compositions of the present invention can be combined with other compounds and compositions having related utilities to prevent and treat the condition or disease of interest, such as inflammatory or autoimmune disorders, conditions and diseases, including inflammatory bowel disease, rheumatoid arthritis, osteoarthritis, psoriatic arthritis, polyarticular arthritis, multiple sclerosis, allergic diseases, psoriasis, atopic dermatitis and asthma, and those pathologies noted above.

For example, in the treatment or prevention of inflammation or autoimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non sedating antihistamine.

Likewise, compounds and compositions of the present invention may be used in combination with other drugs that are used in the treatment, prevention, suppression or amelioration of the diseases or conditions for which compounds and compositions of the present invention are useful. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106,203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) peptide and antibody modulators of immune regulatory molecules such as etanercept (Enbrel®), infliximab (Remicade®), adalimumab (Humira®), certolizumab pegol (Cimzia®), Abatacept (Orencia®), and golimumab (Simponi®), (k) antibody therapies such as orthoclone (OKT3), daclizumab (Zenapax®), basiliximab (Simulect®) and infliximab (Remicade®), (l) other antagonists of the chemokine receptors, especially CCR5, CXCR2, CXCR3, CCR2, CCR3, CCR4, CCR7, $CX_3CR1$ and CXCR6; (m) lubricants or emollients such as petrolatum and lanolin, (n) keratolytic agents (e.g., tazarotene), (o) vitamin $D_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon (β-1α (Avonex®), azathioprine (Imurek®, Imuran®), glatiramer acetate (Capoxone®), a glucocorticoid (e.g., prednisolone) and cyclophosphamide (t) DMARDS such as methotrexate (u) other compounds such as 5-aminosalicylic acid and prodrugs thereof; hydroxychloroquine; D-penicillamine; antimetabolites such as azathioprine, 6-mercaptopurine and methotrexate; DNA synthesis inhibitors such as hydroxyurea and microtubule disrupters such as colchicine. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

VI. Examples

The following examples are offered to illustrate, but not to limit the claimed invention.

Reagents and solvents used below can be obtained from commercial sources such as Aldrich Chemical Co. (Milwaukee, Wis., USA). $^1$H-NMR spectra were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In the examples, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP 1100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM $NH_4OAc$ in acetonitrile/water as delivery system.

Compounds within the scope of this invention can be synthesized as described below, using a variety of reactions known to the skilled artisan. A sample of useful routes to the azaindazole derivatives and certain compounds of the invention are provided below or elsewhere within the present application. In the descriptions of the syntheses that follow, some of the arylpiperazine and heteroaromatic subunit precursors were obtained from commercial sources. These commercial sources include Aldrich Chemical Co., Acros Organics, Ryan Scientific Incorporated, Oakwood Products Incorporated, Lancaster Chemicals, Sigma Chemical Co., Lancaster Chemical Co., TCI-America, Alfa Aesar, Davos Chemicals, and GFS Chemicals. Certain relevant arylpiperazine compounds can be commercially obtained. Others could be prepared as described in U.S. patent application Ser. No. 11/008,774, the contents of which is hereby incorporated in its entirety for all purposes. Also, standard chemistries have been employed to link the arylpiperazine and heteroaromatic subunits (whether commercially obtained or prepared by the methods below) using a suitably optimized linker, such as the acetyl unit described in the body of this invention.

One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

Regioisomerism is a common property in organic chemistry, and is especially common with regards to certain structural types provided herein. Those skilled in the art will recognize, with respect to the compounds described herein, that the coupling reactions with the heteroaromatic ring systems can lead to either one of or a mixture of detectable regioisomers.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Examples

General Method A: HATU Coupling. The desired amine (1.2 equiv) and carboxylic acid were combined in THF (0.2 M) with $Et_3N$ (1-2 equiv) followed by the addition of HATU (1.3 equiv) at room temperature. Upon completion of the reaction, the mixture was diluted with EtOAc, washed with saturated $NaHCO_3$ solution and brine, dried over Na2SO4, filtered, and concentrated under reduced pressure.

General Method B: Acid Chloride Formation and Coupling. The desired carboxylic acid was diluted in $CHCl_3$ (0.25 M) with 2 drops of DMF. Oxalyl chloride (1.2 equiv) was added at room temperature, giving gas evolution from the mixture. After 20-30 minutes, the desired amine (1.2 equiv) was added followed by $Et_3N$ (2.5 equiv) or an equal volume (to $CHCl_3$) of saturated $NaHCO_3$ solution. Upon completion of the reaction, the mixture was diluted with EtOAc, washed with NaHCO₃ and brine, dried over Na2SO4, filtered, and concentrated under reduced pressure.

Example 1

Synthesis of 2-[4-amino-3-(1H-imidazol-2-yl)pyrazolo[3,4-d]pyrimidin-1-yl]-1-[1-(4-fluorophenyl)-6,7-dihydro-5H-pyrazolo[4,3-b]pyridin-4-yl]ethanone

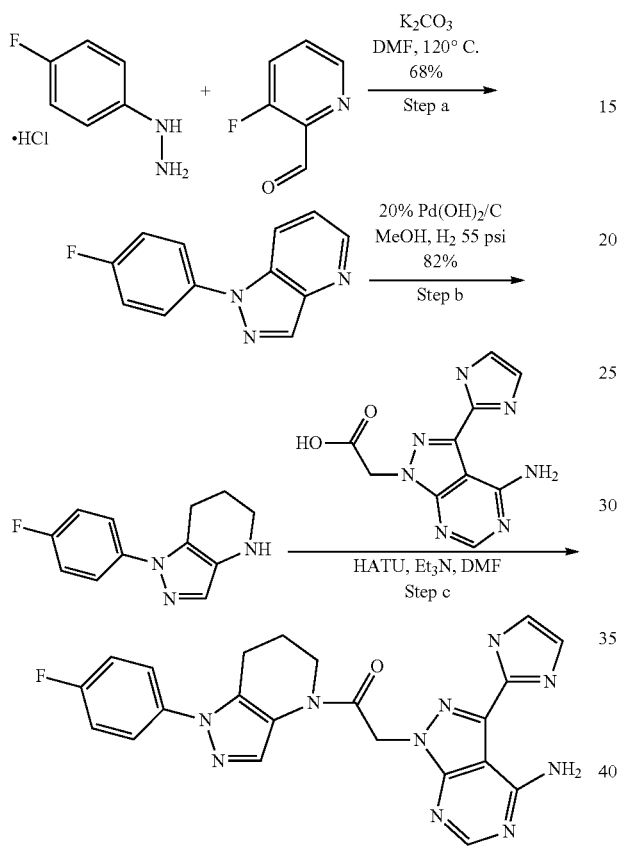

a) To a 500-mL round-bottomed flask was added 4-fluorophenylhydrazine hydrochloride (18.9 g, 116 mmol), 3-fluoro-2-formylpyridine (14.2 g, 113 mmol), K₂CO₃ (47.0 g, 340 mmol), and DMF (150 mL). The slurry was heated to 120° C. in an oil bath for 41 hours at which point the reaction mixture was cooled and poured into 1.2 L of H₂O. The tan precipitate was collected via vacuum filtration and washed with 3×H₂O. The solid was dissolved in CH₂Cl₂ and the resulting solution was washed with brine, dried over Na₂SO₄, filtered, and concentrated under reduced pressure to give a brown solid. The solid was triturated with 200 mL of 9:1 hexanes:EtOAc and dried to provide 1-(4-fluorophenyl)-1H-pyrazolo[4,3-b]pyridine (16.3 g, 68%) as a tan powder. MS: (ES) m/z calculated for $C_{12}H_9FN_3$ [M+H]⁺ 214.1, found 214.1.

b) The heterocycle obtained above (16.3 g, 77 mmol) was dissolved in 380 mL of methanol and treated with 20% Pd(OH)₂/C (10.7 g) in a 2-L Parr bottle. The system was purged and filled with hydrogen (3×) and then shaken under 56 psi hydrogen. An additional 8.0 g of catalyst was added after 1 day. Once the starting material was consumed, the bottle was flushed with nitrogen and the reaction mixture filtered through a pad of Celite, washing with several portions of methanol. The filtrate was concentrated under reduced pressure to provide 1-(4-fluorophenyl)-4,5,6,7-tetrahydro-1H-pyrazolo[4,3-b]pyridine (13.7 g, 82%) as a light tan solid. MS: (ES) m/z calculated for $C_{12}H_{13}FN_3$ [M+H]⁺ 218.1, found 218.1.

c) The compound was prepared from 2-(4-amino-3-(1H-imidazol-2-yl)-1H-pyrazolo[3,4-d]pyrimidin-1-yl)acetic acid and 1-(4-fluorophenyl)-4,5,6,7-tetrahydro-1H-pyrazolo[4,3-b]pyridine above using General Method A. The product was purified by reverse phase HPLC (C18 column, acetonitrile-H₂O with 0.1% TFA as eluent) to give the desired product as a white solid (6.4 mg). ¹H NMR (400 MHz, MeOH-d₄) δ 8.35 (s, 1H), 8.15 (s, 1H), 7.54 (m, 2H), 7.27 (m, 4H), 5.70 (s, 2H), 4.00 (m, 2H), 2.91 (t, J=6.2 Hz, 2H), 2.18 (m, 2H); MS: (ES) m/z calculated for $C_{22}H_{20}FN_{10}O$ [M+H]⁺ 459.18, found 459.1.

Synthesis of 2-(4-chloro-5-methyl-3-(trifluoromethyl)-1H-pyrazol-1-yl)acetic acid

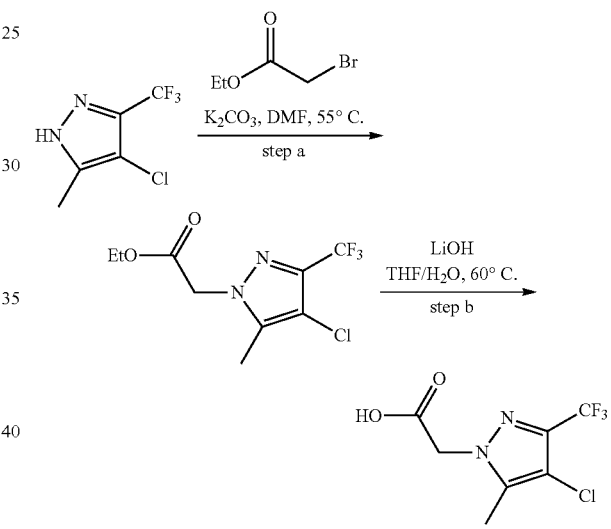

a) To a solution of 4-chloro-5-methyl-3-(trifluoromethyl)pyrazole (15 g, 81.3 mmol) in DMF (82 mL) was added ethyl 2-bromoacetate (13.6 g, 81.3 mmol) and potassium carbonate (12.4 g, 89.4 mmol). The mixture was heated at 55° C. for 10 hours with stirring. After cooling to room temperature, the reaction mixture was diluted with water (100 mL) and extracted with ethyl acetate (3×150 mL). The combined organic layers were washed with brine, dried (Na₂SO₄), filtered, and concentrated in vacuo. The crude residue was purified by flash chromatography (SiO₂, 0-30% ethyl acetate in hexanes) to afford the desired product (18.5 g, 68.4 mmol, 84%).

b) To a solution of ethyl 2-(4-chloro-5-methyl-3-(trifluoromethyl)-1H-pyrazol-1-yl)acetate (7.5 g, 27.7 mmol) in THF (100 mL) and water (50 mL) was added LiOH.H₂O (2.33 g, 55.4 mmol). The mixture was stirred at 60° C. for 5 hours. After cooling to room temperature, the mixture was acidified with 1 N HCl (80 mL) and extracted with 1:2 IPA/CHCl₃ (2×150 mL). The combined organic layers were washed with brine, dried (Na₂SO₄), filtered, and concentrated in vacuo to give the desired compound (6 g, 24.7 mmol, 89%).

¹H NMR (400 MHz, DMSO-d₆) δ 4.98 (s, 2H), 2.21 (s, 3H); MS: (ES) m/z calculated for C₇H₆ClF₃N₂O₂ [M+H]⁺ 243.0, found 243.0.

Example 2

Synthesis of 2-[4-chloro-5-methyl-3-(trifluoromethyl)pyrazol-1-yl]-1-[1-(4-fluorophenyl)-6,7-dihydro-5H-pyrazolo[4,3-b]pyridin-4-yl]ethanone

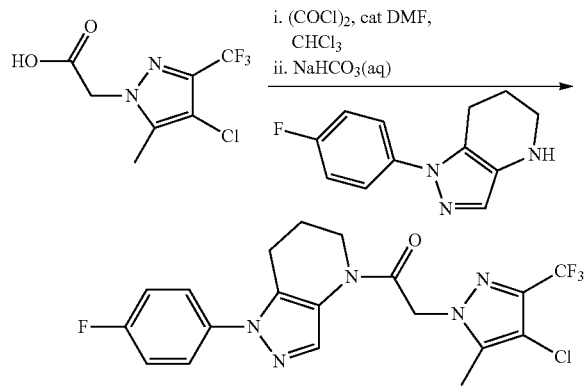

The compound was prepared from 2-(4-chloro-5-methyl-3-(trifluoromethyl)-1H-pyrazol-1-yl)acetic acid and 1-(4-fluorophenyl)-4,5,6,7-tetrahydro-1H-pyrazolo[4,3-b]pyridine using General Method B. The product mixture was washed with 2×1 M NaHSO₄ and 2×1.5 M KOH and the organics were eluted through a silica plug. The resulting slurry was concentrated to a white solid that was triturated with 1:1 hexanes:EtOAc to give the title compound as a crystalline white solid (75.9 mg). ¹H NMR (400 MHz, CDCl₃, mixture of rotamers) δ 8.34 (s, 0.7H), 7.57 (s, 0.3H), 7.44 (m, 2H), 7.15 (m, 2H), 5.24 (s, 0.4H), 5.13 (s, 1.6H), 3.92 (m, 0.5H), 3.84 (m, 1.5H), 2.87 (m, 2H), 2.33 (s, 2.3H), 2.32 (s, 0.7H), 2.12 (m, 1.5H), 2.05 (m, 0.5H); MS: (ES) m/z calculated for C₁₉H₁₇ClF₄N₅O [M+H]⁺ 442.1, found 442.0.

Example 3

Synthesis of 2-(4-chlorophenyl)-1-[1-(4-fluorophenyl)-6,7-dihydro-5H-pyrazolo[4,3-b]pyridin-4-yl]ethanone

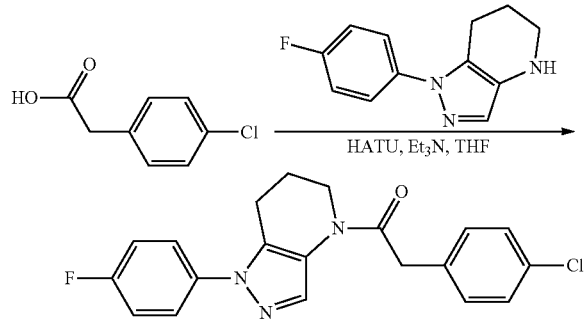

The compound was from prepared from 4-chlorophenylacetic acid and 1-(4-fluorophenyl)-4,5,6,7-tetrahydro-1H-pyrazolo[4,3-b]pyridine using General Method A. The product mixture was crystallized from 4:1 CH₃CN:H₂O to give the title compound as an off-white crystalline solid (37.6 mg). ¹H NMR (400 MHz, MeOD-d₄, mixture of rotamers) δ 8.18 (s, 0.9H), 7.84 (s, 0.1H), 7.56 (m, 2H), 7.25-7.37 (m, 6H), 4.02 (s, 0.2H), 3.92 (s, 1.8H), 2.81 (t, J=6.2 Hz, 2H), 2.49 (m, 2H), 1.90 (m, 2H); MS: (ES) m/z calculated for C₂₀H₁₈ClFN₃O [M+H]⁺ 370.1, found 370.1.

Example 4

Synthesis of 1-[1-(4-chloro-3-methoxy-phenyl)-6,7-dihydro-5H-pyrazolo[4,3-b]pyridin-4-yl]-2-[4-chloro-5-methyl-3-(trifluoromethyl)pyrazol-1-yl]ethanone and 1-(2-(4-chloro-3-methoxyphenyl)-6,7-dihydro-2H-pyrazolo[4,3-b]pyridin-4(5H)-yl)-2-(4-chloro-5-methyl-3-(trifluoromethyl)-1H-pyrazol-1-yl)ethanone

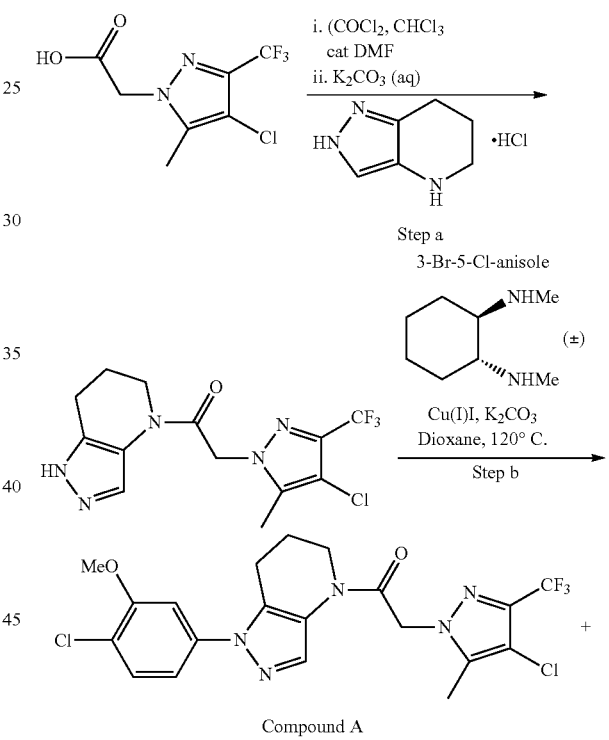

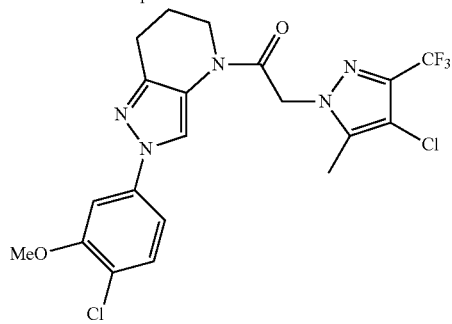

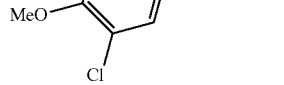

a) 2-(4-Chloro-5-methyl-3-(trifluoromethyl)-1H-pyrazol-1-yl)acetic acid (255 mg, 1.05 mmol) was diluted in 5 mL of CHCl₃ and 2 drops of DMF. Oxalyl chloride (105 μL, 1.2 mmol) was added slowly giving gas evolution. After 30 minutes, 160 mg (1 mmol) of 4,5,6,7-tetrahydro-2H-pyrazolo[4,3-b]pyridine.HCl was added followed by 0.75 mL of 3 M $K_2CO_3$. After 30 minutes, 1 mL of 3 M KOH and 1 mL of MeOH were added to the reaction slurry and the mixture was stirred for 90 minutes. The reaction slurry was washed with brine and the organic layer was dried on MgSO4, filtered, and concentrated to give the amide as a tan solid (184 mg, 53%) that was used without further purification. MS: (ES) m/z calculated for $C_{13}H_{14}ClF_3N_5O$ [M+H]+ 348.1, found 348.0.

b) The amide formed above (104 mg, 0.3 mmol) was combined with 5-bromo-2-chloroanisole (199 mg, 0.9 mmol), 0.3 mL of dioxane, Cu(I)I (11.4 mg, 0.06 mmol, 20%), (±)-trans-N,N'-dimethylcyclohexane-1,2-diamine (21.3 mg, 0.15 mmol, 50%), and $K_2CO_3$ (82.9 mg, 0.6 mmol). The slurry was heated to 120° C. until reaction completion. The product was purified by reverse phase HPLC (C18 column, acetonitrile-$H_2O$ with 0.1% TFA as eluent) to provide two regioisomers. First eluting, Compound A: 1-[1-(4-chloro-3-methoxy-phenyl)-6,7-dihydro-5H-pyrazolo[4,3-b]pyridin-4-yl]-2-[4-chloro-5-methyl-3-(trifluoromethyl)pyrazol-1-yl]ethanone was isolated as a white foam (8.1 mg). $^1$H NMR (400 MHz, CDCl$_3$, mixture of rotamers) δ 8.37 (s, 0.7H), 7.60 (s, 0.3H), 7.41 (d, J=8.4 Hz, 1H), 7.19 (d, J=2.6 Hz, 1H), 6.92 (dd, J=2.2, 8.4 Hz, 1H), 5.24 (s, 0.5H), 5.14 (s, 1.5H), 3.97 (s, 0.6H), 3.95 (s, 2.4H), 3.85 (m, 2H), 2.92 (m, 2H), 2.34 (s, 2.6H), 2.33 (s, 0.4H), 2.13 (m, 1.4H), 2.05 (m, 0.6H); MS: (ES) m/z calculated for $C_{20}H_{19}F_3N_5O_2$ [M+H]$^+$ 488.1, found 488.1. Second eluting, Compound B: 1-(2-(4-chloro-3-methoxyphenyl)-6,7-dihydro-2H-pyrazolo[4,3-b]pyridin-4(5H)-yl)-2-(4-chloro-5-methyl-3-(trifluoromethyl)-1H-pyrazol-1-yl)ethanone was isolated as a white solid (26.8 mg). $^1$H NMR (400 MHz, CDCl$_3$, mixture of rotamers) δ 8.57 (s, 1H), 7.35 (d, J=8.4 Hz, 1H), 7.26 (d, J=2.2 Hz, 1H), 7.11 (dd, J=2.2, 8.4 Hz, 1H), 5.22 (s, 0.2H), 5.16 (s, 1.8H), 3.95 (s, 2.5H), 3.86 (s, 0.5H) 3.84 (m, 2H), 2.93 (t, J=6.6 Hz, 2H), 2.32 (s, 3H), 2.19 (m, 2H); MS: (ES) m/z calculated for $C_{20}H_{19}F_3N_5O_2$ [M+H]$^+$ 488.1, found 488.0.

Example 5a

Synthesis of 1-[1-(4-chlorophenyl)-6,7-dihydro-5H-pyrazolo[4,3-b]pyridin-4-yl]-2-[4-chloro-5-methyl-3-(trifluoromethyl)pyrazol-1-yl]ethanone and 1-(2-(4-chlorophenyl)-6,7-dihydro-2H-pyrazolo[4,3-b]pyridin-4(5H)-yl)-2-(4-chloro-5-methyl-3-(trifluoromethyl)-1H-pyrazol-1-yl)ethanone

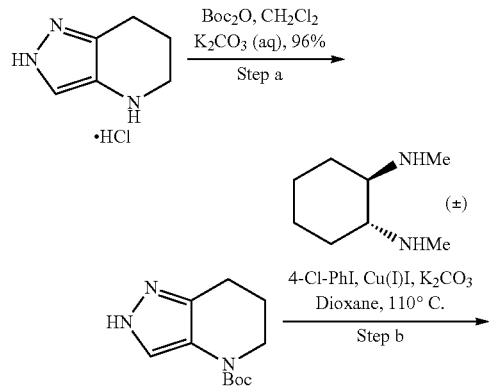

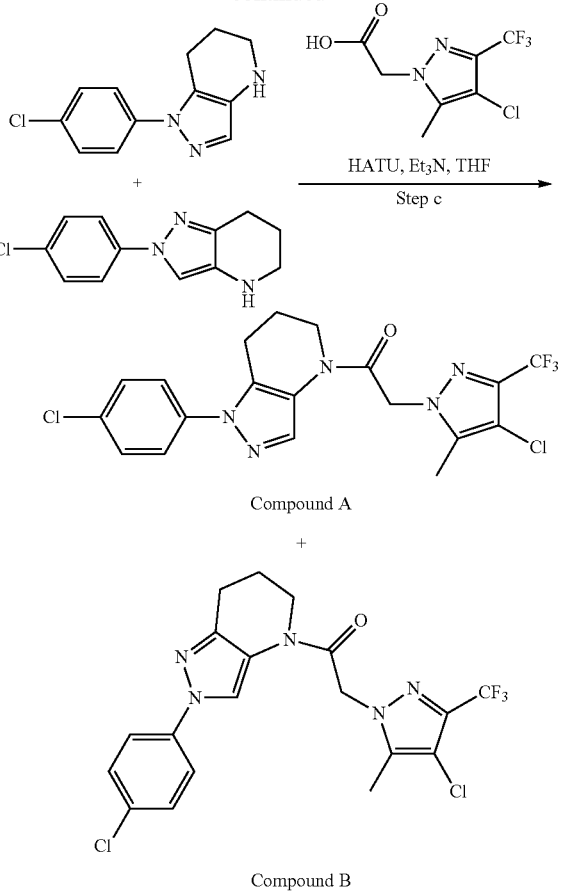

Compound A

Compound B a) 4,5,6,7-Tetrahydro-2H-pyrazolo[4,3-b]pyridine.HCl (319 mg, 2 mmol) was combined with Boc$_2$O (480 mg, 2.2 mmol) and $K_2CO_3$ (1.3 mL, 3 M aqueous, 2 equiv) in $CH_2Cl_2$ (10 mL). After 15 hours, the starting amine was consumed (LCMS). The reaction slurry was washed with brine and the organic layer was dried on MgSO$_4$, filtered, and concentrated to give a viscous yellow oil (446 mg, 96%) that was used without further purification. MS: (ES) m/z calculated for $C_{11}H_{18}N_3O_2$ [M+H]+ 224.1, found 224.2.

b) The Boc-amine formed above (112 mg, 0.5 mmol) was combined with 4-chloroiodobenzene (239 mg, 1 mmol), 6 mL of dioxane, Cu(I)I (12 mg, 0.06 mmol, 10%), (±)-trans-N,N'-dimethylcyclohexane-1,2-diamine (18.5 mg, 0.13 mmol, 25%), and $K_2CO_3$ (138 mg, 1 mmol). The slurry was heated to 110° C. overnight. Two regioisomers are obtained in roughly equal quantities. The reaction slurry was diluted with 20 mL of EtOAc and washed with brine and 2×1 M NaHSO$_4$. The organic layer was dried over MgSO$_4$, filtered, and concentrated to an orange oil that was used without further purification.

c) The regioisomer mixture obtained above (66 mg, approx 0.25 mmol total) was combined with 2-(4-chloro-5-methyl-3-(trifluoromethyl)-1H-pyrazol-1-yl)acetic acid (67 mg, 0.275 mmol), HATU (114 mg, 0.3 mmol), and Et$_3$N (52 µL, 0.38 mmol) in THF (1 mL). After 90 minutes the reaction slurry was diluted with EtOAc, washed with $H_2O$, and concentrated. The residue was purified by reverse phase HPLC (C18 column, acetonitrile-$H_2O$ with 0.1% TFA as eluent) to provide two regioisomers. First eluting, Compound A: 1-[1-(4-chlorophenyl)-6,7-dihydro-5H-pyrazolo[4,3-b]pyridin-4- yl]-2-[4-chloro-5-methyl-3-(trifluoromethyl)pyrazol-1-yl]ethanone was isolated as a white solid (1.7 mg). $^1$H NMR (400 MHz, CDCl$_3$, mixture of rotamers) δ 8.36 (s, 0.8H), 7.59 (s, 0.2H), 7.43 (s, 4H), 5.24 (s, 0.4H), 5.13 (s, 1.6H), 3.92 (m, 0.4H), 3.85 (m, 1.6H), 2.90 (m, 1.8H), 2.77 (m, 0.2H), 2.34 (s, 2.4H), 2.32 (s, 0.6H), 2.13 (m, 1.5H), 2.05 (m, 0.5H); MS: (ES) m/z calculated for $C_{19}H_{17}Cl_2F_3N_5O$ [M+H]$^+$ 458.1, found 458.0. Second eluting, Compound B: 1-(2-(4-chlorophenyl)-6,7-dihydro-2H-pyrazolo[4,3-b]pyridin-4(5H)-yl)-2-(4-chloro-5-methyl-3-(trifluoromethyl)-1H-pyrazol-1-yl)ethanone was isolated as a white solid (31.0 mg). $^1$H NMR (400 MHz, CDCl$_3$) δ 8.56 (s, 1H), 7.56 (m, 2H), 7.36 (m, 2H), 5.16 (s, 2H), 3.84 (s, 2H), 2.93 (t, J=6.6 Hz, 2H), 2.32 (s, 3H), 2.19 (m, 2H); MS: (ES) m/z calculated for $C_{19}H_{17}Cl_2F_3N_5O$ [M+H]$^+$ 458.1, found 458.0.

Example 5b

Synthesis of 1-[1-(4-fluorophenyl)-6,7-dihydro-5H-pyrazolo[4,3-b]pyridin-4-yl]-2-pyrazolo[3,4-b]pyridin-1-yl-ethanone

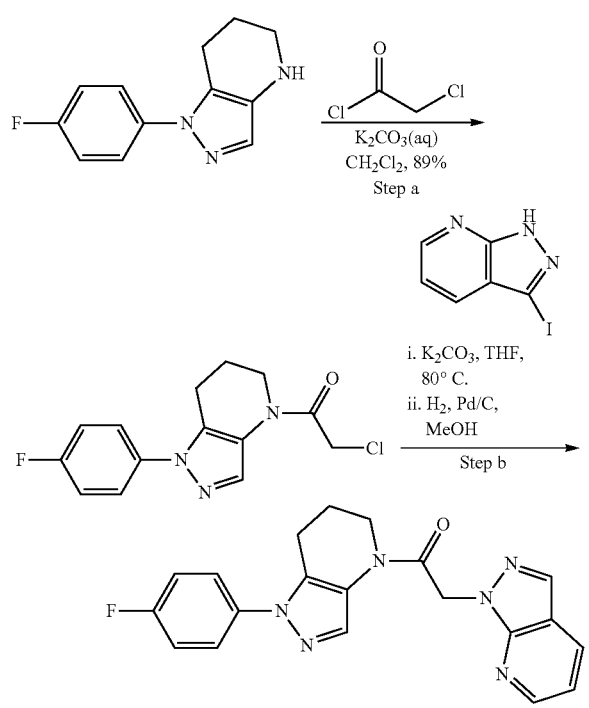

a) To a flask containing 1-(4-fluorophenyl)-4,5,6,7-tetrahydro-1H-pyrazolo[4,3-b]pyridine (0.869 g, 4 mmol) and 3 M K$_2$CO$_3$(aq) (2.6 mL, 8 mmol) in 10 mL of CH$_2$Cl$_2$ was added chloroacetyl chloride (0.35 mL, 4.4 mmol) dropwise. After 20 minutes, the slurry was diluted with 5 mL of H$_2$O and the layers were separated. The organic layer was washed with brine and 2×1 M NaHSO$_4$, dried on MgSO$_4$, filtered, and concentrated to a tan foamy solid (1.05 g, 89%). MS: (ES) m/z calculated for $C_{14}H_{14}ClFN_3O$ [M+H]+ 294.1, found 294.1.

b) The α-chloroacetamide obtained above (147 mg, 0.5 mmol) was diluted in 1.5 mL of THF and treated with K$_2$CO$_3$ (138 mg, 1 mmol) and 3-iodo-1H-pyrazolo[3,4-b]pyridine (130 mg, 0.53 mmol). The slurry was heated to 75° C. Upon completion, 4 mL of methanol and 50 mg of 10% Pd/C were added to the vessel. The reaction mixture was then shaken on a Parr apparatus under 50 psi of H$_2$ overnight. The reaction mixture was filtered through Celite washing with methanol and concentrated. The residue was purified by reverse phase HPLC (C18 column, acetonitrile-H$_2$O with 0.1% TFA as eluent) to provide 30.9 mg of product as a white crystalline solid. $^1$H NMR (400 MHz, CDCl$_3$, mixture of rotamers) δ 8.54 (dd, J=1.5, 4.4 Hz, 1H), 8.35 (s, 0.8H), 8.14 (s, 1H), 8.11 (m, 1H), 7.75 (s, 0.2H), 7.43-7.51 (m, 2H), 7.12-7.21 (m, 3H), 5.70 (s, 0.4H), 5.59 (s, 1.6H), 3.91 (m, 2H), 2.87 (m, 2H), 2.15 (m, 1.6H), 2.05 (m, 0.4H); MS: (ES) m/z calculated for $C_{20}H_{18}FN_6O$ [M+H]$^+$ 377.1, found 377.1.

Example 6

Synthesis of 1-[1-(4-fluorophenyl)-6,7-dihydro-5H-pyrazolo[4,3-b]pyridin-4-yl]-2-pyrazolo[3,4-b]pyridin-1-yl-ethanone

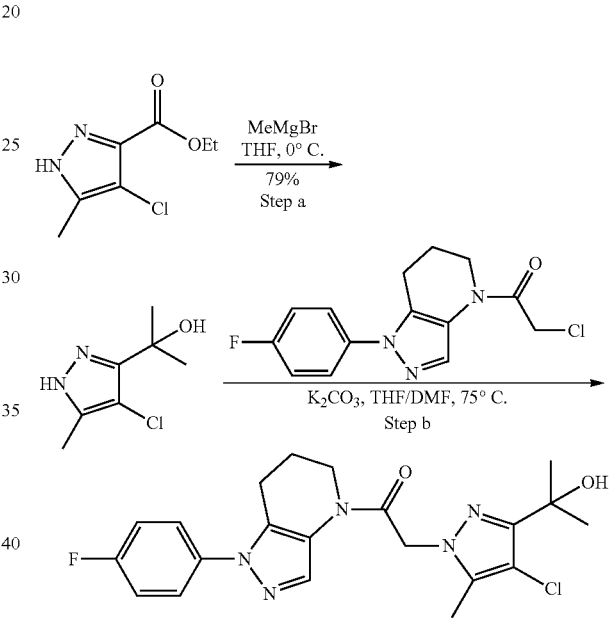

a) A septum-capped vial with stirring bar was rinsed with dry THF and charged with ethyl 4-chloro-5-methyl-1H-pyrazole-3-carboxylate (94 mg, 0.5 mmol) and 1 mL of dry THF. Under N$_2$, the reaction vessel was cooled in an ice bath before dropwise addition of 520 μL of MeMgBr (1.55 mmol, 3 M in Et$_2$O). After 40 minutes, an additional 150 μL of MeMgBr (0.45 mmol) was added. Upon completion, the reaction mixture was treated with 3 mL of 1 M NaHSO$_4$ and extracted with 3×EtOAc. The organic layers were combined, dried on MgSO$_4$, filtered, and concentrated to provide a yellow-tan solid (69 mg, 79%) that was used without further purification. MS: (ES) m/z calculated for $C_7H_{12}ClN_2O$ [M+H]$^+$ 175.1, found 175.1.

b) The carbinol obtained above (69 mg, 0.4 mmol) was diluted in 1.2 mL of THF and 500 μL of DMF and treated with K$_2$CO$_3$ (111 mg, 0.8 mmol) and 2-chloro-1-(1-(4-fluorophenyl)-6,7-dihydro-1H-pyrazolo[4,3-b]pyridin-4(5H)-yl)ethanone (118 mg, 0.4 mmol). The slurry was heated to 75° C. The reaction slurry was diluted with EtOAc and washed with brine, dried on MgSO$_4$, filtered, and concentrated. The residue was purified by reverse phase HPLC (C18 column, acetonitrile-H$_2$O with 0.1% TFA as eluent) to provide 69 mg of the desired product (43%) as a white solid. $^1$H NMR (400 MHz, CDCl$_3$, mixture of rotamers) δ 8.37 (s, 0.8H), 7.63 (s, 0.2H), 7.42-7.46 (m, 2H), 7.13-7.19 (m, 2H), 5.14 (s, 0.4H), 5.03 (s, 1.6H), 3.90 (m, 0.4H), 3.87 (m, 1.6H), 2.86 (m, 2H), 2.28 (s, 2.4H), 2.25 (s, 0.6H), 2.05-2.13 (m, 2H), 1.62 (s, 6H); MS: (ES) m/z calculated for C$_{21}$H$_{24}$ClFN$_5$O$_2$ [M+H]$^+$ 432.2, found 432.1.

Example 7

Synthesis of 2-(4-chloro-5-methyl-3-pyrimidin-2-yl-pyrazol-1-yl)-1-[1-(4-fluorophenyl)-6,7-dihydro-5H-pyrazolo[4,3-b]pyridin-4-yl]ethanone trifluoroacetic acid salt and 2-(4-chloro-3-methyl-5-pyrimidin-2-yl-pyrazol-1-yl)-1-[1-(4-fluorophenyl)-6,7-dihydro-5H-pyrazolo[4,3-b]pyridin-4-yl]ethanone trifluoroacetic acid salt

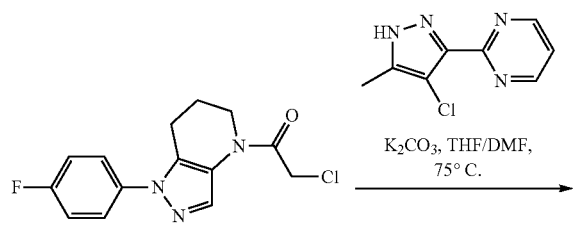

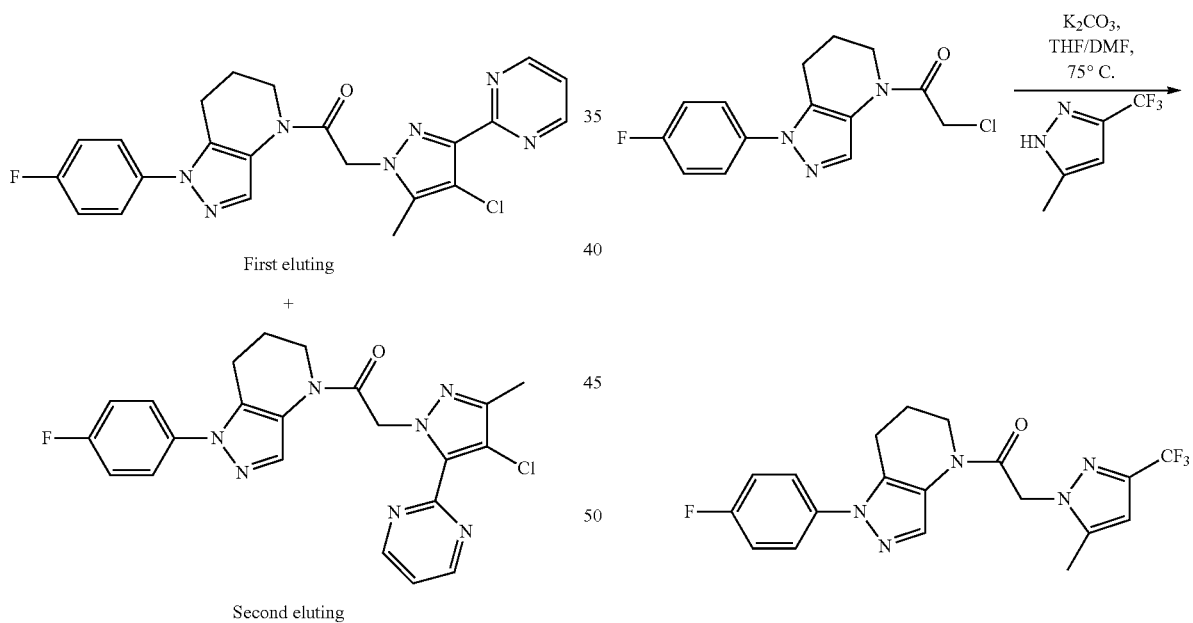

First eluting

+

Second eluting

2-Chloro-1-(1-(4-fluorophenyl)-6,7-dihydro-1H-pyrazolo[4,3-b]pyridin-4(5H)-yl)ethanone (118 mg, 0.4 mmol) was diluted in 1.2 mL of 2:1 THF:DMF and treated with K$_2$CO$_3$ (111 mg, 0.8 mmol) and 2-(4-chloro-5-methyl-1H-pyrazol-3-yl)pyrimidine (78 mg, 0.4 mmol). The slurry was heated to 75° C. and stirred overnight. Two isomers with the same MW were present as assessed by LCMS. The reaction slurry was diluted with EtOAc and washed with brine, dried on MgSO$_4$, filtered, and concentrated. The residue was purified by reverse phase HPLC (C18 column, acetonitrile-H$_2$O with 0.1% TFA as eluent) to provide two regio-isomers. First eluting isomer: 2-(4-Chloro-5-methyl-3-pyrimidin-2-yl-pyrazol-1-yl)-1-[1-(4-fluorophenyl)-6,7-dihydro-5H-pyrazolo[4,3-b]pyridin-4-yl]ethanone trifluoroacetic acid salt: Obtained 25 mg of white needle-shaped crystals. $^1$H NMR (400 MHz, DMSO-d$_6$) δ 8.86 (d, J=5.1 Hz, 2H), 8.13 (s, 1H), 7.59 (m, 2H), 7.44 (t, J=4.8 Hz, 1H), 7.34 (m, 2H), 5.50 (s, 2H), 3.84 (m, 2H), 2.87 (t, J=6.2 Hz, 2H), 2.24 (s, 3H), 2.02 (m, 2H); MS: (ES) m/z calculated for C$_{22}$H$_{20}$ClFN$_7$O [M+H]$^+$ 452.1, found 452.1. Second eluting isomer: 2-(4-Chloro-3-methyl-5-pyrimidin-2-yl-pyrazol-1-yl)-1-[1-(4-fluorophenyl)-6,7-dihydro-5H-pyrazolo[4,3-b]pyridin-4-yl]ethanone trifluoroacetic acid salt: Obtained 8.8 mg of pale orange solid. $^1$H NMR (400 MHz, DMSO-d6, mixture of rotamers) δ 8.87 (d, J=5.1, 1.6H), 8.81 (d, J=5.1 Hz, 0.4H), 7.96 (s, 1H), 7.66 (m, 0.4H), 7.56 (m, 1.6H), 7.42 (t, J=4.8, 1H), 7.33 (m, 2H), 5.72 (s, 2H), 3.84 (m, 2H), 2.85 (t, J=6.2 Hz, 2H), 2.23 (s, 3H), 1.99 (m, 2H); MS: (ES) m/z calculated for C$_{22}$H$_{20}$ClFN$_7$O [M+H]$^+$ 452.1, found 452.1.

Example 8

Synthesis of 1-[1-(4-fluorophenyl)-6,7-dihydro-5H-pyrazolo[4,3-b]pyridin-4-yl]-2-[5-methyl-3-(trifluoromethyl)pyrazol-1-yl]ethanone 2-Chloro-1-(1-(4-fluorophenyl)-6,7-dihydro-1H-pyrazolo[4,3-b]pyridin-4(5H)-yl)ethanone (118 mg, 0.4 mmol) was diluted in 1.2 mL of 2:1 THF:DMF and treated with K$_2$CO$_3$ (111 mg, 0.8 mmol) and 5-methyl-3-(trifluoromethyl)-1H-pyrazole (60 mg, 0.4 mmol). The slurry was heated to 75° C. for 2 hours. The reaction slurry was purified by normal phase flash chromatography (24 g column, eluting with 10-80% EtOAc in hexanes) to provide 109 mg (67%) of the title compound as a white solid. $^1$H NMR (400 MHz, CDCl$_3$) δ 8.36 (s, 0.8H), 7.59 (s, 0.2H), 7.42-7.47 (m, 2H), 7.12-7.25 (m, 2H), 5.25 (s, 0.4H), 5.14 (s, 1.6H), 3.92 (m, 0.4H), 3.86 (m, 1.6H), 2.86 (t, J=6.2 Hz, 2H), 2.37 (s, 2.4H), 2.36 (m, 0.6H), 2.11 (m, 1.6H), 2.04 (m, 0.4H); MS: (ES) m/z calculated for $C_{19}H_{18}F_4N_5O$ [M+H]$^+$ 408.1, found 408.1.

Example 9

Synthesis of 2-[4-chloro-5-methyl-3-(trifluoromethyl)pyrazol-1-yl]-1-[1-(4-fluorophenyl)-6,7-dihydro-5H-pyrazolo[4,3-b]pyridin-4-yl]propan-1-one

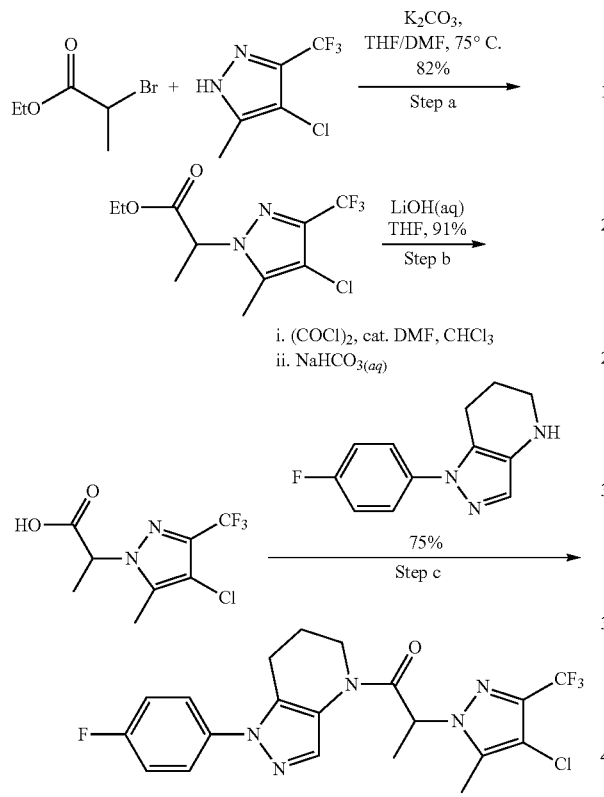

a) Ethyl bromopropionate (1.448 g, 8 mmol), 4-chloro-5-methyl-3-(trifluoromethyl)-1H-pyrazole (1.476 g, 8 mmol), and $K_2CO_3$ (2.211 g, 16 mmol) were combined in 24 mL of 2:1 THF:DMF at 75° C. for 3 hours. The volatiles were evaporated and the residue slurried in 20 mL of 4:1 hexanes: EtOAc and washed with 3×$H_2O$ and 2× brine. The organic layer was dried and purified by flash chromatography (SiO$_2$, 80 g column, eluting with 5-80% EtOAc in hexanes) to provide 1.859 g (82%) of the title compound as a colorless oil. $^1$H NMR (400 MHz, CDCl$_3$) δ 4.95 (q, J=7.3 Hz, 1H), 4.21 (q, J=7.3 Hz, 2H), 2.27 (s, 3H), 1.83 (d, J=7.3 Hz, 3H), 1.81 (t, J=7.3 Hz, 1H); MS: (ES) m/z calculated for $C_{10}H_{13}ClF_3N_2O_2$ [M+H]$^+$ 285.1, found 285.0.

b) The ester obtained above was slurried in 13 mL of THF and 6.5 mL of 2 M LiOH. Upon completion of the reaction, the volatiles were evaporated and 9 mL of 2 M HCl was added to precipitate the product. The precipitate was washed with water (3×5 mL) and dried under vacuum to constant weight. The title compound was obtained as a white solid (1.53 g, 82%). MS: (ES) m/z calculated for $C_8H_9ClF_3N_2O_2$ [M+H]$^+$ 257.0, found 257.0.

c) The title compound was prepared from 2-(4-chloro-5-methyl-3-(trifluoromethyl)-1H-pyrazol-1-yl)propanoic acid and 1-(4-fluorophenyl)-4,5,6,7-tetrahydro-1H-pyrazolo[4,3-b]pyridine using General Method B. The product mixture was washed with 2×1 M NaHSO$_4$. The reaction slurry was purified by flash chromatography (SiO$_2$, 24 g column, eluting with 5-50% EtOAc in hexanes) to provide 137 mg (75%) of the title compound as a white foam. $^1$H NMR (400 MHz, CDCl$_3$) δ 8.41 (s, 1H), 7.43 (m, 2H), 7.15 (m, 2H), 5.52 (q, J=7.0 Hz, 1H), 3.75 (m, 1H), 3.41 (m, 1H), 2.81 (m, 2H), 2.28 (s, 3H), 1.85-1.99 (m, 2H), 1.81 (d, J=7 Hz, 1H); MS: (ES) m/z calculated for $C_{20}H_{19}ClF_4N_5O$ [M+H]$^+$ 456.1, found 456.1.

Example 10

Synthesis of 2-(4-chlorophenyl)-1-[1-(4-fluorophenyl)-6,7-dihydro-5H-pyrazolo[4,3-b]pyridin-4-yl]ethanone

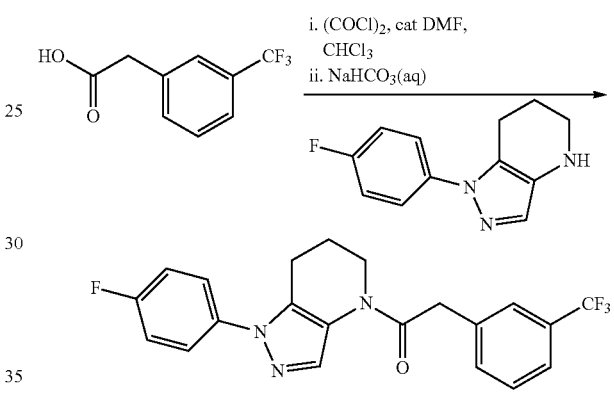

The compound was prepared from 3-trifluoromethylphenylacetic acid and 1-(4-fluorophenyl)-4,5,6,7-tetrahydro-1H-pyrazolo[4,3-b]pyridine using General Method B. The product mixture was washed with 2×1 M NaHSO$_4$. The reaction slurry was purified by flash chromatography (SiO$_2$, 24 g column, eluting with 5-50% EtOAc in hexanes) to provide 83 mg (69%) of the title compound as a white solid. $^1$H NMR (400 MHz, CDCl$_3$, mixture of rotamers) δ 8.45 (s, 1H), 7.42-7.55 (m, 6H), 7.14 (m, 2H), 4.08 (s, 0.3H), 3.95 (s, 1.7H), 3.77 (m, 2H), 2.83 (t, J=6.6 Hz, 2H), 2.01 (m, 2H); MS: (ES) m/z calculated for $C_{21}H_{18}F_4N_3O$ [M+H]$^+$ 404.1, found 404.1.

Example 11

Synthesis of 2-[4-chloro-5-methyl-3-(trifluoromethyl)pyrazol-1-yl]-1-[1-(4-fluorophenyl)-3-methyl-6,7-dihydro-5H-pyrazolo[4,3-b]pyridin-4-yl]ethanone

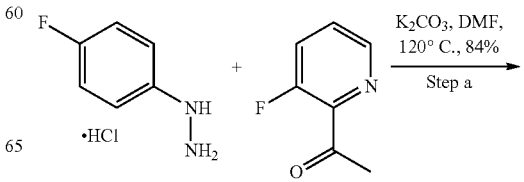

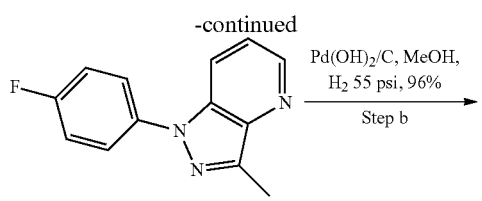

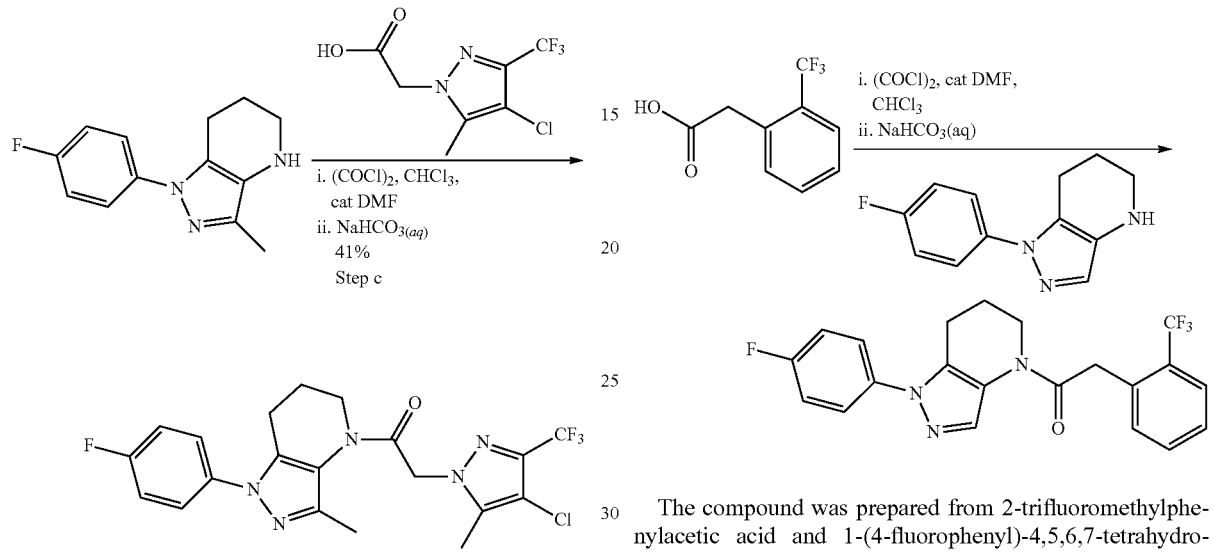

a) To a 100-mL roundbottomed flask was added 4-fluorophenylhydrazine hydrochloride (3.33 g, 20.5 mmol), K₂CO₃ (8.29 g, 60 mmol), and DMF (27 mL). To this slurry was added 2.78 g (20 mmol) of 1-(3-fluoropyridin-2-yl)ethanone, giving a yellow suspension. The mixture was heated to 120° C. for 24 hours at which point the starting materials were consumed. The slurry was cooled to room temperature and 70 mL of H₂O was added to precipitate the product. The solid was collected on a medium fit and washed with 3×H₂O. The solid was dried at 60° C. to provide the product as a tan solid (3.82 g, 84%). MS: (ES) m/z calculated for $C_{13}H_{11}FN_3$ [M+H]⁺ 228.1, found 228.1.

b) Methanol (80 mL), 20% Pd(OH)₂/C (472 mg, approx 0.33 mmol), and 1-(4-fluorophenyl)-3-methyl-1H-pyrazolo[4,3-b]pyridine (3.82 g, 16.8 mmol) were combined in a Parr flask and purged with H₂. The flask was charged to 55 psi H₂ and then the slurry was shaken overnight. The mixture was filtered through Celite, washing with several portions of methanol. The filtrate was then concentrated to give 3.73 g (96% crude yield) of an orange oil that solidified on standing. MS: (ES) m/z calculated for $C_{13}H_{15}FN_3$ [M+H]⁺ 232.1, found 232.1.

c) The title compound was prepared from 2-(4-chloro-5-methyl-3-(trifluoromethyl)-1H-pyrazol-1-yl)acetic acid and 1-(4-fluorophenyl)-3-methyl-4,5,6,7-tetrahydro-1H-pyrazolo[4,3-b]pyridine using General Method B. The product mixture was washed with 1 M NaHSO₄. The reaction slurry was purified by flash chromatography (SiO₂, 24 g column, eluting with 5-50% EtOAc in hexanes) to provide 75 mg (41%) of the title compound as a white solid. ¹H NMR (400 MHz, CDCl₃, mixture of rotamers) δ 7.47 (m, 0.8H), 7.40 (m, 1.2H), 7.14 (m, 2H), 5.11 (s, 1.2H), 5.01 (s, 0.8H), 3.81 (m, 2H), 2.85 (m, 2H), 2.29-2.40 (m, 6H), 2.07 (m, 2H); MS: (ES) m/z calculated for $C_{20}H_{19}ClF_4N_5O$ [M+H]⁺ 456.1, found 456.1.

Example 12

Synthesis of 1-(1-(4-fluorophenyl)-6,7-dihydro-1H-pyrazolo[4,3-b]pyridin-4(5H)-yl)-2-(2-(trifluoromethyl)phenyl)ethanone

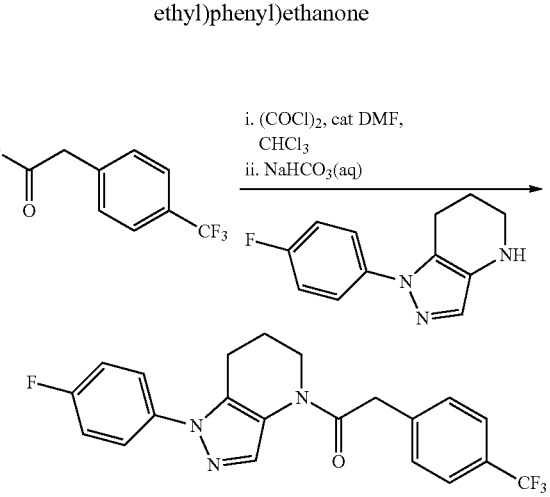

The compound was prepared from 2-trifluoromethylphenylacetic acid and 1-(4-fluorophenyl)-4,5,6,7-tetrahydro-1H-pyrazolo[4,3-b]pyridine using General Method B. The product mixture was washed with 1 M NaHSO₄. The reaction slurry was purified by flash chromatography (SiO₂, 24 g column, eluting with 5-50% EtOAc in hexanes) to provide 72 mg (59%) of the title compound as a white solid. ¹H NMR (400 MHz, CDCl₃, mixture of rotamers) δ 8.46 (s, 0.8H), 7.70 (m, 1H), 7.55 (m, 1.2H), 7.41-7.50 (m, 4H), 7.15 (m, 2H), 4.19 (s, 0.3H), 4.06 (s, 1.7H), 3.95 (m, 0.3H), 3.76 (m, 1.7H), 2.82-2.88 (m, 2H), 2.03 (m, 2H); MS: (ES) m/z calculated for $C_{21}H_{18}F_4N_3O$ [M+H]⁺ 404.1, found 404.1.

Example 13

Synthesis of 1-(1-(4-fluorophenyl)-6,7-dihydro-1H-pyrazolo[4,3-b]pyridin-4(5H)-yl)-2-(4-(trifluoromethyl)phenyl)ethanone The compound was prepared from 4-trifluoromethylphenylacetic acid and 1-(4-fluorophenyl)-4,5,6,7-tetrahydro-1H-pyrazolo[4,3-b]pyridine using General Method B. The product mixture was washed with 1 M NaHSO₄. The reaction slurry was purified by flash chromatography (SiO₂, 24 g column, eluting with 5-50% EtOAc in hexanes) to provide 77 mg (64%) of the title compound as a white solid. $^1$H NMR (400 MHz, CDCl₃, mixture of rotamers) δ 8.45 (s, 0.8H), 7.62 (d, J=7.8 Hz, 2H), 7.55 (s, 0.2H), 7.40-7.49 (m, 4H), 7.15 (m, 2H), 4.08 (s, 0.3H), 3.96 (m, 2H), 3.75 (m, 1.7H), 2.80-2.86 (m, 2H), 2.00 (m, 2H); MS: (ES) m/z calculated for $C_{21}H_{18}F_4N_3O$ [M+H]⁺ 404.1, found 404.1.

Example 14

Synthesis of 2-(4-chloro-3-(trifluoromethyl)phenyl)-1-(1-(4-fluorophenyl)-6,7-dihydro-1H-pyrazolo[4,3-b]pyridin-4(5H)-yl)ethanone

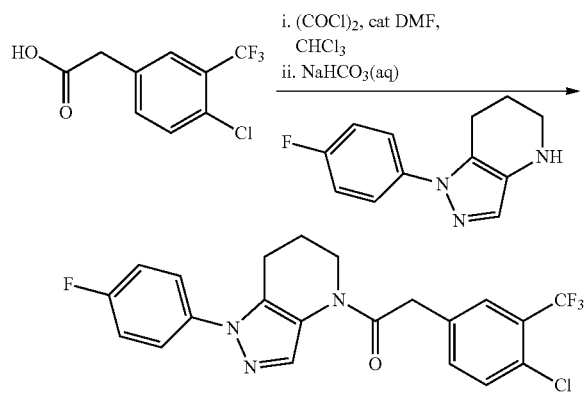

The compound was prepared from 4-chloro-3-trifluoromethylphenylacetic acid and 1-(4-fluorophenyl)-4,5,6,7-tetrahydro-1H-pyrazolo[4,3-b]pyridine using General Method B. The product mixture was washed with brine and 2×1 M NaHSO₄. The reaction slurry was purified by flash chromatography (SiO₂, 24 g column, eluting with 5-50% EtOAc in hexanes) to provide 54 mg (41%) of the title compound as a white solid. $^1$H NMR (400 MHz, CDCl₃, mixture of rotamers) δ 8.44 (s, 0.8H), 7.59 (m, 1H), 7.57 (s, 0.2H), 7.41-7.51 (m, 4H), 7.17 (m, 2H), 4.03 (s, 0.3H), 3.95 (m, 0.3H), 3.91 (s, 1.7H), 3.78 (m, 1.7H), 2.82-2.85 (m, 2H), 2.05 (m, 2H); MS: (ES) m/z calculated for $C_{21}H_{17}ClF_4N_3O$ [M+H]⁺ 438.1, found 438.1.

Example 15

Synthesis of 2-(3-chloro-4-(trifluoromethyl)phenyl)-1-(1-(4-fluorophenyl)-6,7-dihydro-1H-pyrazolo[4,3-b]pyridin-4(5H)-yl)ethanone

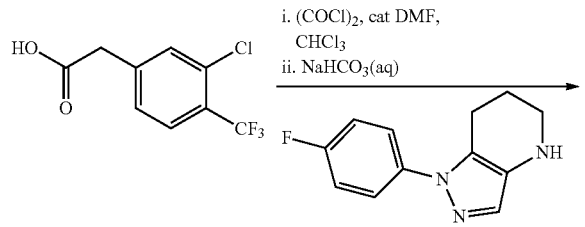

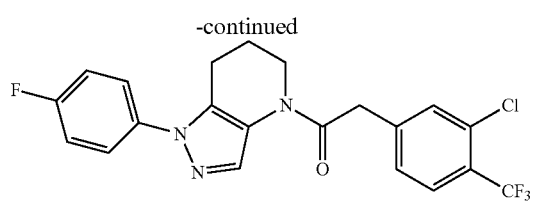

The compound was from prepared from 3-chloro-4-trifluoromethylphenylacetic acid and 1-(4-fluorophenyl)-4,5,6,7-tetrahydro-1H-pyrazolo[4,3-b]pyridine using General Method B. The product mixture was washed with brine and 2×1 M NaHSO₄. The reaction slurry was purified by flash chromatography (SiO₂, 24 g column, eluting with 5-60% EtOAc in hexanes) to provide 68 mg (52%) of the title compound as a white solid. $^1$H NMR (400 MHz, CDCl₃, mixture of rotamers) δ 8.45 (s, 0.8H), 7.67 (m, 1H), 7.55 (s, 0.2H), 7.44-7.49 (m, 3H), 7.30 (m, 1H), 7.14-7.21 (m, 2H), 4.04 (s, 0.4H), 3.94 (m, 0.4H), 3.92 (s, 1.6H), 3.77 (m, 1.6H), 2.82-2.87 (m, 2H), 2.04 (m, 2H); MS: (ES) m/z calculated for $C_{21}H_{17}ClF_4N_3O$ [M+H]⁺ 438.1, found 438.1.

Example 16

Synthesis of 2-[4-chloro-5-methyl-3-(trifluoromethyl)pyrazol-1-yl]-1-[1-(4-fluorophenyl)-3-methyl-6,7-dihydro-5H-pyrazolo[4,3-b]pyridin-4-yl]ethanone

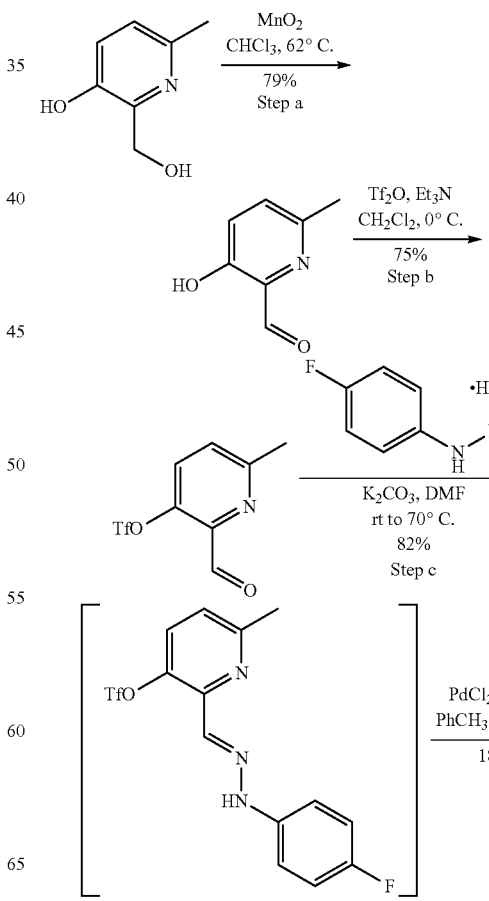

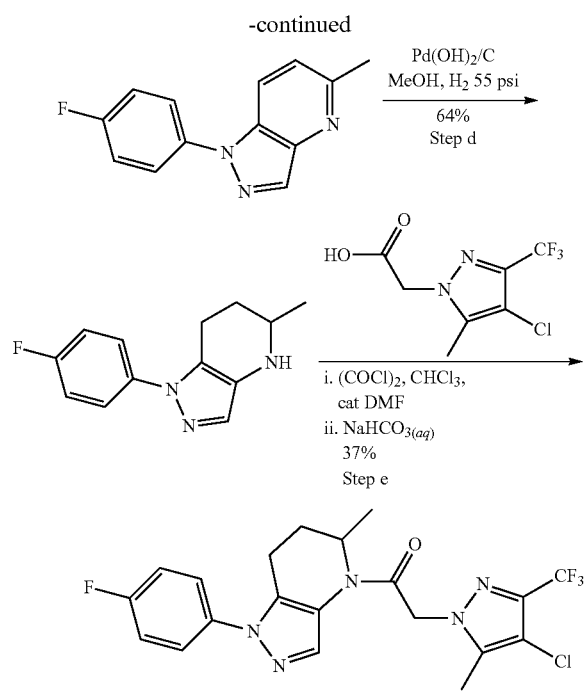

a) 2,6-Lutidine-α-2,3-diol (4.17 g, 30 mmol) was dissolved in 60 mL of CHCl₃ and treated with MnO₂ (15.65 g, 180 mmol). The slurry was heated to 62° C. for 90 minutes at which point the reaction was complete. The reaction mixture was filtered through a thin layer of Celite and washed with several portions of CHCl₃. The filtrate was concentrated to provide the product as a tan crystalline solid (3.24 g, 79%). MS: (ES) m/z calculated for $C_7H_8NO_2$ [M+H]⁺ 138.0, found 138.0.

b) The aldehyde obtained above was dissolved in CH₂Cl₂ (20 mL) and Et₃N (2.3 mL, 16.5 mmol). Trifluoromethanesulfonic anhydride (Tf₂O, 2.78 mL, 16.5 mmol) was added dropwise over 5 minutes. Additional portions of Et₃N (500 μL) and Tf₂O (200 μL) were added after 30 minutes. After 75 minutes, the reaction mixture was washed with 2×H₂O and 2× saturated NaHCO₃. The organic layer was dried on MgSO₄, filtered, and concentrated to provide 3.02 g (75%) of orange oil that was used directly in the next step.

c) The triflate above (1.08 g, 4 mmol) was dissolved in 5 mL of DMF in a septum-capped vial. Potassium carbonate (1.66 g, 12 mmol) and 4-fluorophenylhydrazine hydrochloride (678 mg, 4.17 mmol) were added and the slurry was stirred at room temperature, becoming a deep orange-red. Within 3 hours, LCMS indicated that the starting material was consumed providing the hydrazine intermediate (both with and without triflate). To this reaction mixture was added 400 mg (0.55 mmol) of PdCl₂(dppf) and 5 mL of PhCH₃. The flask was placed in a 100° C. heating block overnight. The reaction mixture was poured into 100 mL of H₂O and 80 mL of EtOAc. The mixture was filtered through a plug of Celite and the layers separated. The organic layer was concentrated and the residue was purified by normal phase flash chromatography (40 g column, eluting with 15-70% EtOAc in hexanes) to provide 160 mg (18%) of the title compound as an orange oily solid. MS: (ES) m/z calculated for $C_{13}H_{11}FN_3$ [M+H]⁺ 228.1, found 228.1.

d) Methanol (3.5 mL), 20% Pd(OH)₂/C (200 mg, approx 0.14 mmol), and 1-(4-fluorophenyl)-5-methyl-1H-pyrazolo[4,3-b]pyridine (160 mg, 0.7 mmol) were combined in a Parr flask and purged 2×H₂. The flask was charged to 55 psi H₂ and then the slurry was shaken for 2 days. The mixture was filtered through Celite washing with several portions of methanol. The filtrate was concentrated to 103 mg (64% crude yield) of an orange oily solid. MS: (ES) m/z calculated for $C_{13}H_{15}FN_3$ [M+H]⁺ 232.1, found 232.1.

e) The compound was from prepared from 2-(4-chloro-5-methyl-3-(trifluoromethyl)-1H-pyrazol-1-yl)acetic acid and 1-(4-fluorophenyl)-5-methyl-4,5,6,7-tetrahydro-1H-pyrazolo[4,3-b]pyridine using General Method B. The product mixture was washed with 2×1 M NaHSO₄. The reaction slurry was purified by flash chromatography (SiO₂, 24 g column, eluting with 5-50% EtOAc in hexanes) to provide 37 mg (37%) of the title compound as a white foam. ¹H NMR (400 MHz, CDCl₃, mixture of rotamers) δ 8.37 (s, 0.8H), 7.58 (s, 0.2H), 7.49 (m, 2H), 7.17 (m, 2H), 5.08-5.31 (m, 2H), 4.51 (m, 1H), 2.78-2.99 (m, 2H), 2.34 (s, 2.3H), 2.31 (s, 0.7H), 1.97-2.09 (m, 2H), 1.36 (d, J=6.7 Hz, 2.4H), 1.15 (d, J=6.6 Hz, 0.6H); MS: (ES) m/z calculated for $C_{20}H_{19}ClF_4N_5O$ [M+H]⁺ 456.1, found 456.1.

General Scheme for Examples 17-20

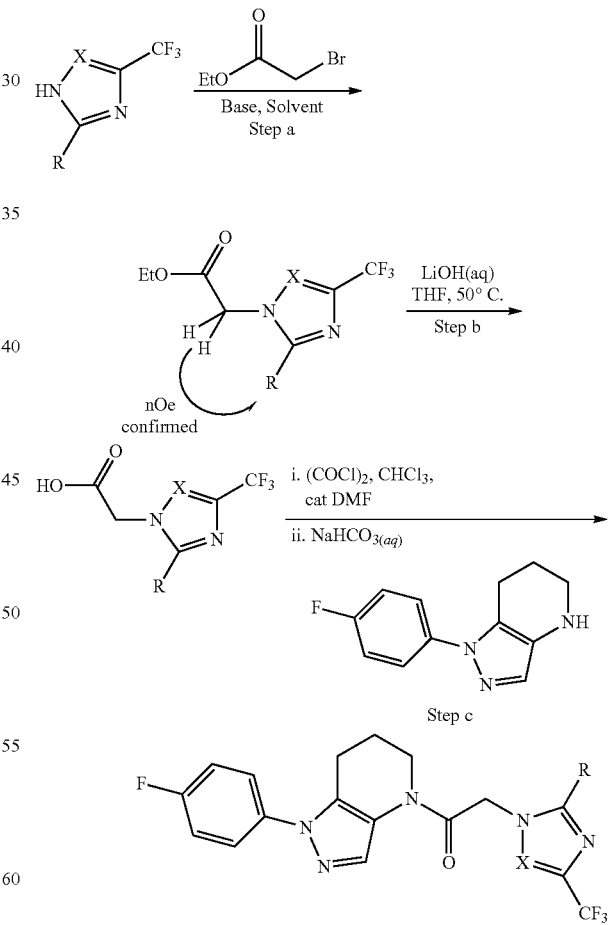

X = CH, N
R = H, Me

Example 17

Synthesis of 1-(1-(4-fluorophenyl)-6,7-dihydro-1H-pyrazolo[4,3-b]pyridin-4(5H)-yl)-2-(4-(trifluoromethyl)-1H-imidazol-1-yl)ethanone trifluoroacetic acid salt

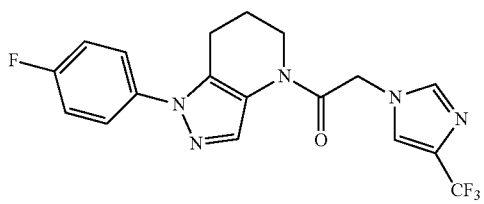 [SMILES: O=C(Cn1cnc(C(F)(F)F)c1)N1CCCc2c1cnn2-c1ccc(F)cc1]

a) To a vial was added 4-trifluoromethyl-1H-imidazole (953 mg, 7 mmol), 7 mL of ethanol, and sodium ethoxide (524 mg, 7.7 mmol). To this mixture was slowly added ethyl bromoacetate (1.29 g, 7.7 mmol). After 18 hours, an additional 100 μL of ethyl bromoacetate and approximately 100-200 mg of NaOEt were added. After 90 minutes, the reaction was quenched with NaHCO$_3$ and extracted with 3×EtOAc. The organic layer was concentrated and the residue was purified by flash chromatography (SiO$_2$, 80 g column, eluting with 15-90% EtOAc in hexanes) to provide 746 mg (48%) of the title compound as a crystalline solid. MS: (ES) m/z calculated for C$_8$H$_{10}$F$_3$N$_2$O$_2$ [M+H]$^+$ 223.1, found 223.1.

b) The ester obtained above (746 mg, 3.35 mmol) was dissolved in 10 mL of THF and treated with 3.5 mL of 2 M LiOH(aq). The mixture was heated in a 50° C. bath for 5 hours. The volatiles were evaporated and 1 mL of 6 N HCl (aq) and 1 mL of 1 M NaHSO$_4$ were added. The resulting precipitate was collected and washed with H$_2$O, dissolved in EtOAc, and concentrated to white solid (200 mg). The aqueous washes were concentrated to half volume and a second crop was collected (141 mg). $^1$H NMR (400 MHz, CD$_3$OD) δ 7.80 (s, 1H), 7.64 (s, 1H), 4.94 (s, 2H); MS: (ES) m/z calculated for C$_6$H$_6$F$_3$N$_2$O$_2$ [M+H]$^+$ 195.0, found 195.1 The regiochemistry of the system was confirmed by nOe between the α-methylene and both imidazole ring protons.

c) The title compound was prepared from 2-(4-(trifluoromethyl)-1H-imidazol-1-yl)acetic acid and 1-(4-fluorophenyl)-4,5,6,7-tetrahydro-1H-pyrazolo[4,3-b]pyridine using General Method B. The product mixture was washed with 2× brine. The reaction slurry was purified by reverse phase HPLC (C18 column, acetonitrile-H$_2$O with 0.1% TFA as eluent) to provide 29 mg of the title compound as a white solid. $^1$H NMR (400 MHz, CD$_3$OD, mixture of rotamers) δ 8.25 (s, 0.9H), 7.85 (s, 0.1H), 7.82 (s, 1H), 7.65 (s, 1H), 7.55 (m, 2H), 7.27 (m, 2H), 5.45 (s, 0.2H), 5.33 (s, 1.8H), 3.90 (m, 0.2H), 3.87 (m, 1.8H), 2.88 (t, J=6.6 Hz, 2H), 2.13 (m, 1.8H), 2.03 (m, 0.2H); MS: (ES) m/z calculated for C$_{18}$H$_{16}$F$_4$N$_5$O [M+H]$^+$ 394.1, found 394.1.

Example 18

Synthesis of 1-(1-(4-fluorophenyl)-6,7-dihydro-1H-pyrazolo[4,3-b]pyridin-4(5H)-yl)-2-(2-methyl-4-(trifluoromethyl)-1H-imidazol-1-yl)ethanone trifluoroacetic acid salt

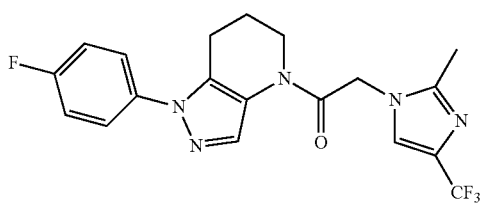 [SMILES: Cc1nc(C(F)(F)F)cn1CC(=O)N1CCCc2c1cnn2-c1ccc(F)cc1]

a) To a vial was added 2-methyl-4-(trifluoromethyl)-1H-imidazole (750 mg, 5 mmol), 5 mL of THF, 2.5 mL of DMF, and K$_2$CO$_3$ (2.07 g, 15 mmol). To this mixture was slowly added ethyl bromoacetate (1.00 g, 6 mmol). After 2 hours, the slurry was diluted with EtOAc, filtered on Celite, and concentrated. The residue was purified by flash chromatography (SiO$_2$, 80 g column, eluting with 15-100% EtOAc in hexanes) to provide 476 mg (40%) of the title compound as a colorless oil. $^1$H NMR (400 MHz, CDCl$_3$) δ 7.20 (s, 1H), 4.61 (s, 2H), 4.28 (q, J=7.0 Hz, 2H), 1.63 (s, 3H), 1.31 (t, J=7.0 Hz, 3H); MS: (ES) m/z calculated for C$_9$H$_{12}$F$_3$N$_2$O$_2$ [M+H]$^+$ 237.1, found 237.1. The regiochemistry of the system was confirmed by nOe between the α-methylene and both the imidazole ring and methyl protons.

b) The ester obtained above (476 mg, 2 mmol) was dissolved in 6 mL of THF and treated with 2 mL of 2 M LiOH the resulting mixture was stirred at room temperature overnight. The volatiles were then evaporated and 670 μL of 6 N HCl (aq) was added. The resulting precipitate was collected, washed with H$_2$O, and dried under vacuum to constant weight to provide the title compound as a white powder (284 mg, 68%). MS: (ES) m/z calculated for C$_6$H$_6$F$_3$N$_2$O$_2$ [M+H]$^+$ 209.0, found 209.0.

c) The title compound was prepared from 2-(2-methyl-4-(trifluoromethyl)-1H-imidazol-1-yl)acetic acid and 1-(4-fluorophenyl)-4,5,6,7-tetrahydro-1H-pyrazolo[4,3-b]pyridine using General Method B. The product mixture was diluted with 1 mL of CHCl$_3$ and washed with H$_2$O. The organic layer was concentrated and the residue was purified by reverse phase HPLC (C18 column, acetonitrile-H$_2$O with 0.1% TFA as eluent) to provide 31 mg of the title compound as a white solid. $^1$H NMR (400 MHz, CD$_3$OD, mixture of rotamers) δ 8.24 (s, 0.9H), 7.88 (s, 0.1H), 7.52-7.60 (m, 3H), 7.24-7.32 (m, 2H), 5.36 (s, 0.2H), 5.26 (s, 1.8H), 3.89 (m, 2H), 2.89 (t, J=6.2 Hz, 2H), 2.38 (s, 2.7H), 2.36 (m, 0.3H), 2.14 (m, 2H); MS: (ES) m/z calculated for C$_{19}$H$_{18}$F$_4$N$_5$O [M+H]$^+$ 408.1, found 408.1.

Example 19

Synthesis of 1-(1-(4-fluorophenyl)-6,7-dihydro-1H-pyrazolo[4,3-b]pyridin-4(5H)-yl)-2-(3-(trifluoromethyl)-1H-1,2,4-triazol-1-yl)ethanone

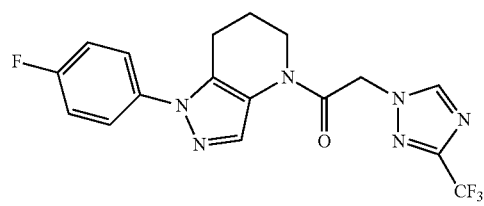 [SMILES: O=C(Cn1cnc(C(F)(F)F)n1)N1CCCc2c1cnn2-c1ccc(F)cc1]

a) To a vial was added 3-(trifluoromethyl)-1H-1,2,4-triazole (358 mg, 2.6 mmol), 2.6 mL of ethanol, and sodium ethoxide (354 mg, 5.2 mmol). To this mixture was slowly added ethyl bromoacetate (320 μL, 2.9 mmol). After 18 hours, the reaction mixture was concentrated and acidified with 1 mL of 6 N HCl (aq). The slurry was diluted in EtOAc and H$_2$O and the layers were separated. The organic layer was concentrated and the residue was purified by flash chromatography (SiO$_2$, 40 g column, eluting with 2-80% EtOAc in hexanes) to provide 423 mg (73%) of the title compound as a crystalline solid. $^1$H NMR (400 MHz, CDCl$_3$) δ 8.30 (s, 1H), 5.05 (s, 2H), 4.29 (q, J=7.3 Hz, 2H), 1.32 (t, J=7.1 Hz, 3H); MS: (ES) m/z calculated for C$_8$H$_{10}$F$_3$N$_2$O$_2$ [M+H]$^+$ 224.1, found 224.1. The regiochemistry of the system was confirmed by nOe between the α-methylene and triazole ring proton.

b) The ester obtained above (142 mg, 0.64 mmol) was dissolved in 2 mL of THF and treated with 650 μL of 2 M LiOH (aq). The mixture was stirred at 50° C. for 75 minutes. The volatiles were evaporated and 500 μL of 6 N HCl (aq) was added. The solution was extracted with 2×EtOAc, dried on MgSO$_4$, filtered, and concentrated to provide the title compound as a colorless oil (108 mg, 76%). MS: (ES) m/z calculated for $C_5H_3F_3N_3O_2$ [M−H]$^-$ 194.1, found 194.1.

c) The title compound was prepared from 2-(3-(trifluoromethyl)-1H-1,2,4-triazol-1-yl)acetic acid and 1-(4-fluorophenyl)-4,5,6,7-tetrahydro-1H-pyrazolo[4,3-b]pyridine using General Method B. The product mixture was washed with 2× brine. The reaction slurry was purified by reverse phase HPLC (C18 column, acetonitrile-H$_2$O with 0.1% TFA as eluent) to provide 33 mg of the title compound as a white solid. $^1$H NMR (400 MHz, CD$_3$OD, mixture of rotamers) δ 8.41 (s, 1H), 8.35 (s, 0.75H), 7.60 (s, 0.25H), 7.43-7.50 (m, 2H), 7.15-7.23 (m, 2H), 5.41 (s, 0.5H), 5.30 (s, 1.5H), 3.94 (m, 0.5H), 3.84 (m, 1.5H), 2.89 (m, 2H), 2.15 (m, 1.5H), 2.07 (m, 0.5H); MS: (ES) m/z calculated for $C_{17}H_{15}F_4N_6O$ [M+H]$^+$ 395.1, found 395.1.

Example 20

Synthesis of 1-(1-(4-fluorophenyl)-6,7-dihydro-1H-pyrazolo[4,3-b]pyridin-4(5H)-yl)-2-(5-methyl-3-(trifluoromethyl)-1H-1,2,4-triazol-1-yl)ethanone

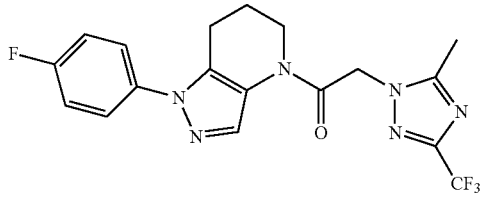 [SMILES: Cc1nc(C(F)(F)F)nn1CC(=O)N1CCCc2c1cnn2-c1ccc(F)cc1]

a) To a flask was added 5-methyl-3-(trifluoromethyl)-1H-1,2,4-triazole (2.27 g, 15 mmol), 15 mL of EtOH, and sodium ethoxide (2.04 g, 30 mmol). To this mixture was slowly added ethyl bromoacetate (2.76 g, 16.5 mmol). After 5 hours, the reaction was quenched with 3 mL of 6 N HCl (aq) and adjusted to pH 7 with saturated NaHCO$_3$. The volume was reduced by half and the slurry was diluted with 30 mL of EtOAc. The layers were separated and the organic layer washed with H$_2$O. The organic layer was concentrated and the residue was purified by flash chromatography (SiO$_2$, 80 g column, eluting with 5-60% EtOAc in hexanes) to provide 2.00 g (56%) of the title compound as a pale yellow oil. $^1$H NMR (400 MHz, CDCl$_3$) δ 4.91 (s, 2H), 4.28 (q, J=7.0 Hz, 2H), 2.50 (s, 3H), 1.31 (t, J=7.3 Hz, 3H); MS: (ES) m/z calculated for $C_8H_{11}F_3N_3O_2$ [M+H]$^+$ 238.1, found 238.1. The regiochemistry of the system was confirmed by nOe between the α-methylene and both the triazole methyl protons.

b) The ester obtained above (2.00 g, 8.4 mmol) was dissolved in 10 mL of THF and treated with 8 mL of 2 M LiOH (aq). The mixture was stirred at 50° C. for 2 hours. The volatiles were evaporated and 2.5 mL of 6 N HCl (aq) was added. The slurry was extracted with 20 mL of EtOAc, dried on MgSO$_4$, filtered, and concentrated to provide the title compound (1.59 g, 90%) as yellow oil that solidified on standing. MS: (ES) m/z calculated for $C_6H_5F_3N_3O_2$ [M−H]$^-$ 208.0, found 208.1.

c) The title compound was prepared from 2-(5-methyl-3-(trifluoromethyl)-1H-1,2,4-triazol-1-yl)acetic acid and 1-(4-fluorophenyl)-4,5,6,7-tetrahydro-1H-pyrazolo[4,3-b]pyridine using General Method B. The product mixture was diluted with 1 mL of CHCl$_3$ and washed with H$_2$O. The organic layer was concentrated and the residue was purified by reverse phase HPLC (C18 column, acetonitrile-H$_2$O with 0.1% TFA as eluent) to provide 37 mg of the title compound as a white solid. $^1$H NMR (400 MHz, CDCl$_3$, mixture of rotamers) δ 8.34 (s, 0.8H), 7.59 (s, 0.2H), 7.44-7.50 (m, 2H), 7.14-7.27 (m, 2H), 5.29 (s, 0.4H), 5.18 (s, 1.6H), 3.93 (m, 0.4H), 3.86 (m, 1.6H), 2.88 (m, 2H), 2.56 (s, 2.4H), 2.55 (m, 0.6H), 2.14 (m, 1.6H), 2.06 (m, 0.4H); MS: (ES) m/z calculated for $C_{18}H_{17}F_4N_6O$ [M+H]$^+$ 409.1, found 409.1.

Example 21

Synthesis of 2-(4-chloro-5-methyl-3-(trifluoromethyl)-1H-pyrazol-1-yl)-1-(1-(5-fluoropyridin-2-yl)-6,7-dihydro-1H-pyrazolo[4,3-b]pyridin-4(5H)-yl)ethanone

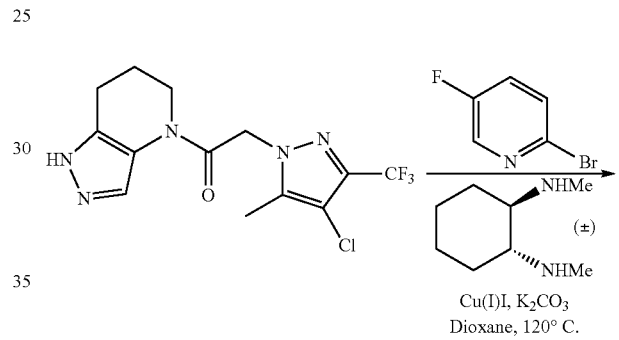

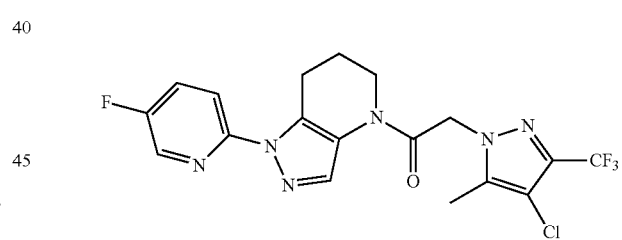

2-(4-Chloro-5-methyl-3-(trifluoromethyl)-1H-pyrazol-1-yl)-1-(6,7-dihydro-1H-pyrazolo[4,3-b]pyridin-4(5H)-yl) ethanone (104 mg, 0.3 mmol) was combined with 5-fluoro-2-bromopyridine (106 mg, 0.6 mmol), 0.3 mL of dioxane, Cu(I)I (11.4 mg, 0.06 mmol, 20%), (±)-trans-N,N'-dimethylcyclohexane-1,2-diamine (21.3 mg, 0.15 mmol, 50%), and K$_2$CO$_3$ (83 mg, 0.6 mmol). The slurry was heated to 120° C. until complete (approx 3 hours). The reaction mixture was diluted in 4 mL of EtOAc and washed with 2×H$_2$O. The organic layer was concentrated and the residue was purified by reverse phase HPLC (C18 column, acetonitrile-H$_2$O with 0.1% TFA as eluent) to provide the title compound as a white solid. $^1$H NMR (400 MHz, CDCl$_3$, mixture of rotamers) δ 8.91 (s, 0.8H), 8.33 (d, J=2.7 Hz, 0.2H), 8.28 (d, J=2.9 Hz, 0.8H), 7.87-7.94 (m, 1H), 7.68-7.77 (m, 1H), 5.42 (s, 1.6H), 5.41 (s, 0.4H), 3.93 (s, 1.6H), 3.88 (s, 0.4H), 2.88 (t, J=6.4 Hz, 2H), 2.29 (s, 0.6H), 2.28 (s, 2.4H), 2.18 (m, 2H); MS: (ES) m/z calculated for $C_{18}H_{16}ClF_4N_6O$ [M+H]$^+$ 443.1, found 443.0.

Example 22

Synthesis of ethyl 2-(4-chloro-5-methyl-3-(trifluoromethyl)-1H-pyrazol-1-yl)-2-methylpropanoate and ethyl 3-(4-chloro-5-methyl-3-(trifluoromethyl)-1H-pyrazol-1-yl)-2-methylpropanoate

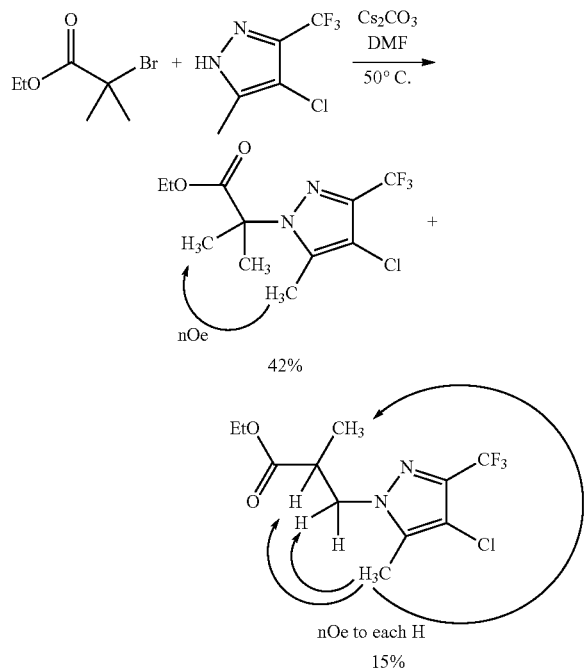

To 4-chloro-5-methyl-3-(trifluoromethyl)-1H-pyrazole (1.846 g, 2.22 mL, 10 mmol) and cesium carbonate (6.516 g, 20 mmol) slurried in DMF (20 mL) was added ethyl α-bromoisobutyrate (2.926 g, 15 mmol) in one portion. The flask was placed in an oil bath and the system heated to 50° C. After 2 hours, an additional portion of ethyl α-bromoisobutyrate (1 mL) was added and heating continued. Upon completion as determined by consumption of the pyrazole, the slurry was diluted with EtOAc and filtered through Celite, washing with an additional 150 mL of EtOAc. The filtrate was washed with 3× brine (half saturated), dried on MgSO$_4$, filtered, and concentrated to a yellow oil. The product was purified by flash chromatography (SiO$_2$, 150 g column, eluting with 5-60% EtOAc in hexanes) to provide 1.24 g (42%) of the geminal dimethyl compound and 434 mg (15%) of the α-methyl compound as colorless oils. Ethyl 2-(4-chloro-5-methyl-3-(trifluoromethyl)-1H-pyrazol-1-yl)-2-methylpropanoate. $^1$H NMR (400 MHz, CDCl$_3$) δ 4.25 (q, J=7.1 Hz, 2H), 2.19 (s, 3H), 1.81 (s, 6H), 1.27 (t, J=7.1 Hz, 3H); MS: (ES) m/z calculated for $C_{11}H_{15}ClF_3N_2O_2$ [M+H]$^+$ 299.1, found 299.0. The regiochemistry of the system was confirmed by nOe between the α-methyl and pyrazole methyl protons. Ethyl 3-(4-chloro-5-methyl-3-(trifluoromethyl)-1H-pyrazol-1-yl)-2-methylpropanoate. $^1$H NMR (400 MHz, CDCl$_3$) δ 4.35 (dd, J=8.2, 13.8 Hz, 1H), 4.11 (q, J=7.1 Hz, 2H), 4.02 (dd, J=6.5, 13.8 Hz, 1H), 3.18 (m, 1H), 2.30 (s, 3H), 1.21 (t, J=7.0 Hz, 3H), 1.21 (d, J=7.1 Hz, 3H); MS: (ES) m/z calculated for $C_{11}H_{15}ClF_3N_2O_2$ [M+H]$^+$ 299.1, found 299.0. The regiochemistry of the system was confirmed by nOe between the pyrazole methyl and neighboring protons.

Example 23

Synthesis of 2-[4-chloro-5-methyl-3-(trifluoromethyl)pyrazol-1-yl]-1-[1-(4-fluorophenyl)-6,7-dihydro-5H-pyrazolo[4,3-b]pyridin-4-yl]-2-methyl-propan-1-one

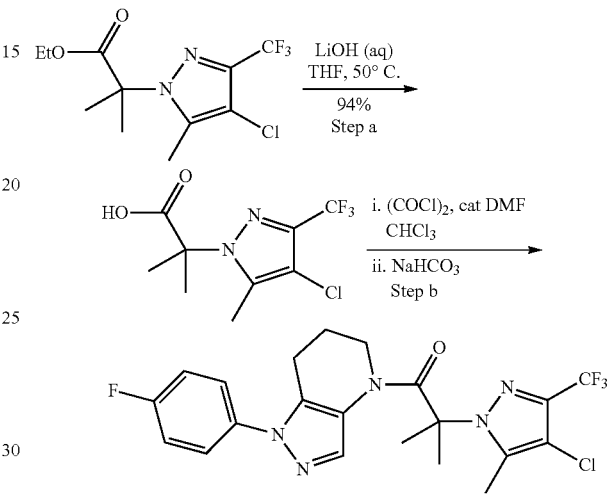

a) To ethyl 2-(4-chloro-5-methyl-3-(trifluoromethyl)-1H-pyrazol-1-yl)-2-methylpropanoate (1.24 g, 4.2 mmol) was added 12 mL of THF and 4.2 mL of 2 M LiOH (aq). The slurry was heated at 50° C. for 80 min and then the volume reduced by half. The solution was acidified with HCl to provide a white precipitate that was washed with 1 M NaHSO$_4$ and 2×H$_2$O. Drying provided 1.06 g (94%) the title compound. MS: (ES) m/z calculated for $C_9H_{11}ClF_3N_2O_2$ [M+H]$^+$ 271.0, found 271.0.

b) The title compound was from prepared from 2-(4-chloro-5-methyl-3-(trifluoromethyl)-1H-pyrazol-1-yl)-2-methylpropanoic acid and 1-(4-fluorophenyl)-4,5,6,7-tetrahydro-1H-pyrazolo[4,3-b]pyridine using General Method B. The product mixture was washed with 2×1 M NaHSO$_4$. The organic layer was concentrated and the residue was purified by flash chromatography (SiO$_2$, 24 g column, eluting with 5-50% EtOAc in hexanes) to provide 80 mg (68%) of the title compound as a white solid. $^1$H NMR (400 MHz, CDCl$_3$) δ 8.44 (s, 1H), 7.44 (m, 2H), 7.16 (m, 2H), 3.08 (m, 2H), 2.74 (t, J=6.6 Hz, 2H), 2.21 (s, 3H), 1.91 (s, 6H), 1.76 (ddd, J=5.8, 6.2, 10.5 Hz, 2H); MS: (ES) m/z calculated for $C_{21}H_{21}ClF_4N_5O$ [M+H]$^+$ 470.1, found 470.1.

General Scheme for Examples 24 and 25

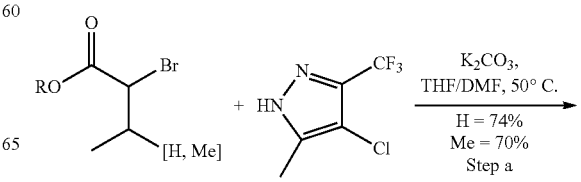

-continued

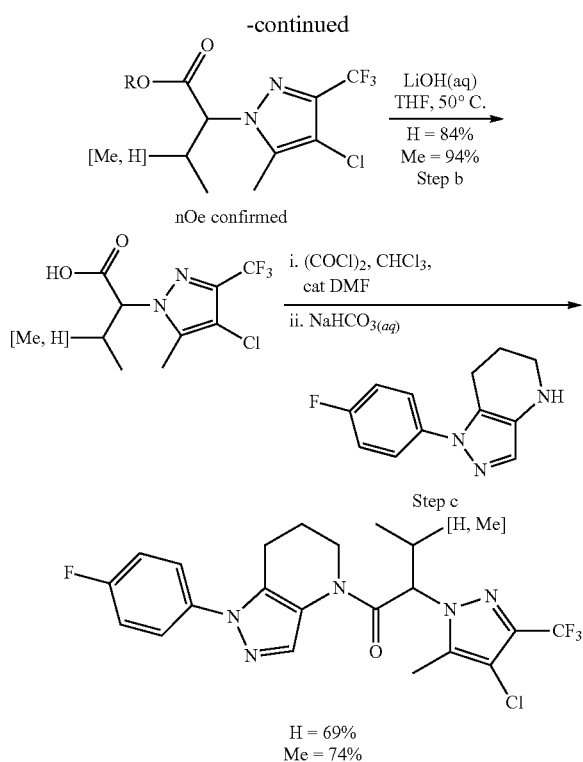

nOe confirmed

Example 24

Synthesis of 2-(4-chloro-5-methyl-3-(trifluoromethyl)-1H-pyrazol-1-yl)-1-(1-(4-fluorophenyl)-6,7-dihydro-1H-pyrazolo[4,3-b]pyridin-4(5H)-yl)butan-1-one

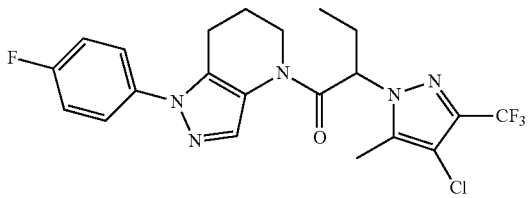 [SMILES: CCC(C(=O)N1CCCc2c1cnn2-c1ccc(F)cc1)n1nc(C(F)(F)F)c(Cl)c1C]

a) Methyl bromobutyrate (996 mg, 5.5 mmol), 4-chloro-5-methyl-3-(trifluoromethyl)-1H-pyrazole (923 mg, 5 mmol), and $K_2CO_3$ (1.382 g, 10 mmol) were combined in 15 mL of 2:1 THF:DMF at 50° C. overnight. The solids were filtered off washing with EtOAc and the volatiles were evaporated. The residue was diluted in EtOAc and washed with 3×$H_2O$ and 2× brine. The organic layer was concentrated and the residue was purified by flash chromatography ($SiO_2$, 40 g column, eluting with 2-50% EtOAc in hexanes) to provide 1.06 g (74%) of the product as a colorless oil. $^1$H NMR (400 MHz, $CDCl_3$) δ 4.27 (dd, J=6.7, 9.0 Hz, 1H), 3.74 (s, 3H), 2.34 (m, 2H), 2.27 (s, 3H), 0.89 (t, J=6.5 Hz, 3H); MS: (ES) m/z calculated for $C_{10}H_{13}ClF_3N_2O_2$ [M+H]$^+$ 285.1, found 285.0. The regiochemistry of the system was confirmed by nOe between the α-methine proton and pyrazole methyl protons (and those of the ethyl group).

b) The ester obtained above (1.06 g, 3.72 mmol) was slurried in 10 mL THF and 3.7 mL of 2 M LiOH (aq) at 50° C. After 70 minutes, the volatiles were evaporated and 1.25 mL of 6 M HCl (aq) was added. The slurry was extracted with 2×$CH_2Cl_2$ and the organic layer dried on $MgSO_4$, filtered, and concentrated to a pale yellow solid (0.844 mg, 84%). MS: (ES) m/z calculated for $C_9H_{11}ClF_3N_2O_2$ [M+H]$^+$ 270.0, found 270.0.

c) The title compound was prepared from 2-(4-chloro-5-methyl-3-(trifluoromethyl)-1H-pyrazol-1-yl)butanoic acid and 1-(4-fluorophenyl)-4,5,6,7-tetrahydro-1H-pyrazolo[4,3-b]pyridine using General Method B. The product mixture was washed with 2×1 M $NaHSO_4$. The reaction slurry was purified by flash chromatography ($SiO_2$, 24 g column, eluting with 5-50% EtOAc in hexanes) to provide 81 mg (69%) of the title compound as a white solid. $^1$H NMR (400 MHz, $CDCl_3$) δ 8.43 (s, 1H), 7.44 (m, 2H), 7.16 (m, 2H), 5.30 (dd, J=6.7, 8.6 Hz, 1H), 3.81 (ddd, J=3.2, 8.6, 11.5 Hz, 1H), 3.50 (ddd, J=3.1, 7.4, 10.2 Hz, 1H), 2.79 (dt, J=2.8, 6.3 Hz, 2H), 2.33 (m, 1H), 2.30 (s, 3H), 2.22 (m, 1H), 1.96 (m, 1H), 1.86 (m, 1H), 0.98 (t, J=7.0 Hz, 3H); MS: (ES) m/z calculated for $C_{20}H_{19}ClF_4N_5O$ [M+H]$^+$ 470.1, found 470.1.

Example 25

Synthesis of 2-[4-chloro-5-methyl-3-(trifluoromethyl)pyrazol-1-yl]-1-[1-(4-fluorophenyl)-6,7-dihydro-5H-pyrazolo[4,3-b]pyridin-4-yl]-3-methyl-butan-1-one

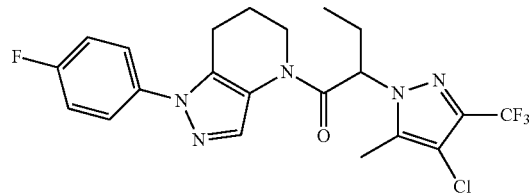 [SMILES: CCC(C(=O)N1CCCc2c1cnn2-c1ccc(F)cc1)n1nc(C(F)(F)F)c(Cl)c1C]

a) Ethyl 2-bromo-3-methylbutanoate (836 mg, 4 mmol), 4-chloro-5-methyl-3-(trifluoromethyl)-1H-pyrazole (738 mg, 4 mmol), and $K_2CO_3$ (1.106 g, 8 mmol) were combined in 12 mL of 2:1 THF:DMF at 50° C. overnight. An additional 400 µL of alkylator was added and stirring continued overnight. The solids were filtered off washing with EtOAc and the volatiles were evaporated. The residue was diluted in EtOAc and washed with 2× brine (half-saturated). The organic layer was concentrated and the residue purified by normal phase flash chromatography (40 g column, eluting with 5% EtOAc in hexanes) to provide 870 mg (70%) of the title compound as a colorless oil. $^1$H NMR (400 MHz, $CDCl_3$) δ 4.42 (d, J=10.2 Hz, 1H), 4.20 (q, J=7.4 Hz, 2H), 2.83 (m, 1H), 2.31 (s, 3H), 1.24 (t, J=7.4 Hz, 3H), 1.09 (d, J=6.7 Hz, 3H), 0.82 (d, J=6.6 Hz, 3H); MS: (ES) m/z calculated for $C_{12}H_{17}ClF_3N_2O_2$ [M+H]$^+$ 313.1, found 313.1. The regiochemistry of the system was confirmed by nOe between the α-methine proton and pyrazole methyl protons (and those of the isopropyl group).

b) The ester obtained above (870 mg, 2.8 mmol) was slurried in 8.3 mL THF and 2.8 mL of 2 M LiOH (aq) at 50° C. After 80 minutes, the volatiles were evaporated and 1 mL of 6 M HCl (aq) was added. The resulting precipitate was collected, washed with 3×$H_2O$, and dried to afford the title compound as a white solid (844 mg, 94%). MS: (ES) m/z calculated for $C_{10}H_{13}ClF_3N_2O_2$ [M+H]$^+$ 285.1, found 285.0.

c) The title compound was prepared from 2-(4-chloro-5-methyl-3-(trifluoromethyl)-1H-pyrazol-1-yl)-3-methylbutanoic acid and 1-(4-fluorophenyl)-4,5,6,7-tetrahydro-1H-pyrazolo[4,3-b]pyridine using General Method B. The product mixture was washed with 2×1 M NaHSO$_4$. The reaction slurry was purified by flash chromatography (SiO$_2$, 24 g column, eluting with 5-50% EtOAc in hexanes) to provide 89 mg (74%) of the title compound as a glassy white solid. $^1$H NMR (400 MHz, CDCl$_3$) δ 8.44 (s, 1H), 7.44 (m, 2H), 7.16 (m, 2H), 5.03 (d, J=10.9 Hz, 1H), 3.89 (ddd, J=2.7, 8.2, 10.9 Hz, 1H), 3.78 (ddd, J=2.7, 7.8, 10.9 Hz, 1H), 2.96 (m, 1H), 2.79 (m, 2H), 2.37 (s, 3H), 1.99 (m, 1H), 1.82 (m, 1H), 1.12 (d, J=6.3 Hz, 3H), 0.79 (d, J=7.1 Hz, 3H); MS: (ES) m/z calculated for C$_{22}$H$_{23}$ClF$_4$N$_5$O [M+H]$^+$ 484.1, found 484.1.

Example 26

Synthesis of 1-[1-(4-fluorophenyl)-6,7-dihydro-5H-pyrazolo[4,3-b]pyridin-4-yl]-2-[3-(trifluoromethyl)pyrazolo[3,4-b]pyridin-1-yl]ethanone

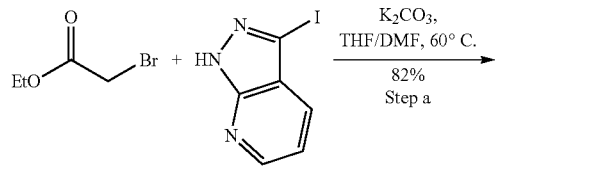

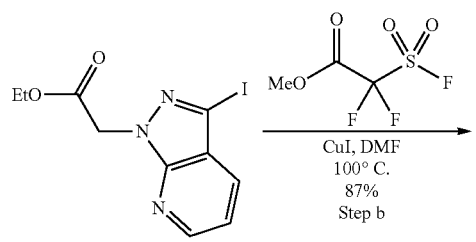

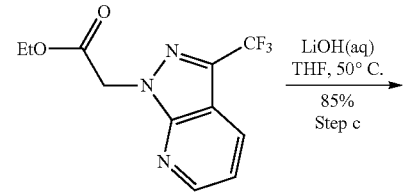

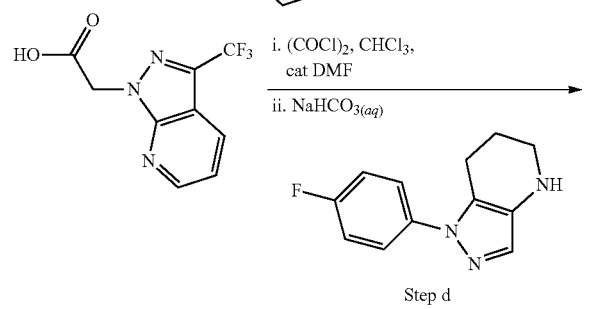

a) Ethyl bromoacetate (1.336 g, 8 mmol), 3-iodo-1H-pyrazolo[3,4-b]pyridine (1.953 mg, 8 mmol), and K$_2$CO$_3$ (2.211 g, 16 mmol) were combined in 32 mL of 2:1 THF:DMF at 60° C. After 4 hours, the volatiles were removed, the residue diluted with 50 mL of EtOAc, and the slurry washed with 3× brine (half-saturated). The organic layer was concentrated and the residue purified by flash chromatography (SiO$_2$, 80 g column, eluting with 5-20% EtOAc in hexanes) to provide 2.172 g (82%) of the product as granular white solid. MS: (ES) m/z calculated for C$_{10}$H$_{11}$IN$_3$O$_2$ [M+H]$^+$ 332.0, found 332.0.

b) Methyl fluorosulfonyldifluoroacetate (MFSDA, 1.25 mL, 10.5 mmol) was added dropwise to a slurry of ethyl 2-(3-iodo-1H-pyrazolo[3,4-b]pyridin-1-yl)acetate (994 mg, 3 mmol), CuI (571 mg, 3 mmol), and DMF (30 mL). The mixture was heated to 100° C. for 1 hour and diluted in 50 mL of EtOAc. The reaction mixture was filtered through a pad of Celite, washing with additional EtOAc. The filtrate was concentrated to half volume and an equal volume of brine was added resulting in the formation of a precipitate. The solid was collected and washed with H$_2$O and dried at 60° C. to provide the title compound as a voluminous crystalline solid (1.366 g, 87%).

c) The ester obtained above (546 mg, 2 mmol) was slurried in 6 mL THF and 1.5 mL of 2 M LiOH (aq) at 50° C. After completion, the volatiles were evaporated and 3 mL of 1 M NaHSO$_4$ (aq) was added. The resulting precipitate was collected, washed with 3×H$_2$O, and dried to afford the title compound as a white powder (415 mg, 85%). MS: (ES) m/z calculated for C$_9$H$_7$F$_3$N$_3$O$_2$ [M+H]$^+$ 246.0, found 246.0.

d) The title compound was prepared from 2-(3-(trifluoromethyl)-1H-pyrazolo[3,4-b]pyridin-1-yl)acetic acid and 1-(4-fluorophenyl)-4,5,6,7-tetrahydro-1H-pyrazolo[4,3-b]pyridine using General Method B. The reaction slurry was purified by flash chromatography (SiO2, 24 g column, eluting with 5-70% EtOAc in hexanes) to provide 58 mg of the title compound as a white solid. $^1$H NMR (400 MHz, CDCl$_3$, mixture of rotamers) δ 8.65 (dd, J=2.6, 4.7 Hz, 1H), 8.32 (s, 0.8H), 8.24 (d, J=8.2 Hz, 1H), 7.72 (s, 0.2H), 7.44-7.52 (m, 2H), 7.33 (dd, J=4.3, 8.2 Hz, 1H), 7.13-7.23 (m, 2H), 5.76 (s, 0.4H), 5.65 (s, 1.6H), 3.93 (m, 2H), 2.89 (t, J=6.3 Hz, 2H), 2.17 (m, 1.6H), 2.06 (m, 0.4H); MS: (ES) m/z calculated for C$_{21}$H$_{17}$F$_4$N$_6$O [M+H]$^+$ 445.1, found 445.1.

Example 27

Synthesis of 1-[1-(4-fluorophenyl)-6,7-dihydro-5H-pyrazolo[4,3-b]pyridin-4-yl]-2-[3-(trifluoromethyl)-4,5,6,7-tetrahydropyrazolo[3,4-b]pyridin-1-yl]ethanone

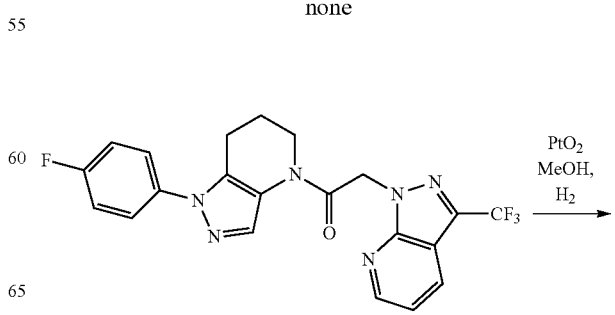

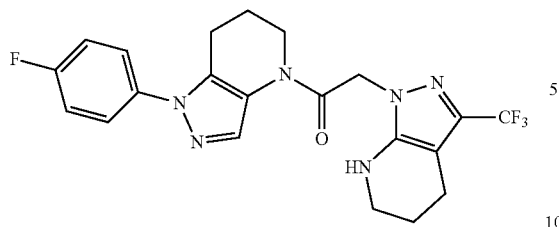
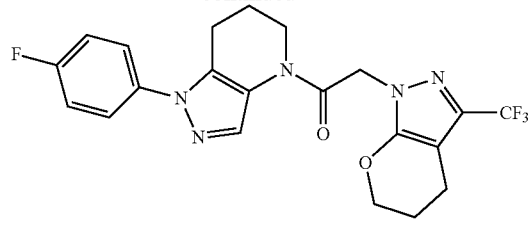

1-[1-(4-Fluorophenyl)-6,7-dihydro-5H-pyrazolo[4,3-b]pyridin-4-yl]-2-[3-(trifluoromethyl)pyrazolo[3,4-b]pyridin-1-yl]ethanone (22.2 mg, 0.05 mmol) prepared above was dissolved in 1 mL of methanol and treated with ~20 mg of $PtO_2$ in a septum-capped vial. The vial was purged and filled with hydrogen gas twice and then placed under a hydrogen atmosphere (balloon) and stirred overnight. The slurry was filtered and the filtrate purified by reverse phase HPLC (C18 column, acetonitrile-$H_2O$ with 0.1% TFA as eluent) to provide the title compound (solution was neutralized and extracted to provide the free base) as a white solid (13 mg, 60%). $^1$H NMR (400 MHz, $CDCl_3$, mixture of rotamers) δ 8.36 (s, 0.85H), 7.71 (s, 0.15H), 7.43-7.49 (m, 2H), 7.14-7.19 (m, 2H), 5.15 (s, 0.3H), 5.00 (s, 1.7H), 4.29 (br s, 1H), 3.88-3.93 (m, 2H), 3.29 (m, 2H), 2.85 (t, J=6.3 Hz, 2H), 2.63 (t, J=6.2 Hz, 2H), 2.09 (m, 2H), 1.85 (m, 2H); MS: (ES) m/z calculated for $C_{21}H_{21}F_4N_6O$ [M+H]$^+$ 449.1, found 449.1.

Example 28

Synthesis of 1-[1-(4-fluorophenyl)-6,7-dihydro-5H-pyrazolo[4,3-b]pyridin-4-yl]-2-[3-(trifluoromethyl)-5,6-dihydro-4H-pyrano[2,3-c]pyrazol-1-yl]ethanone

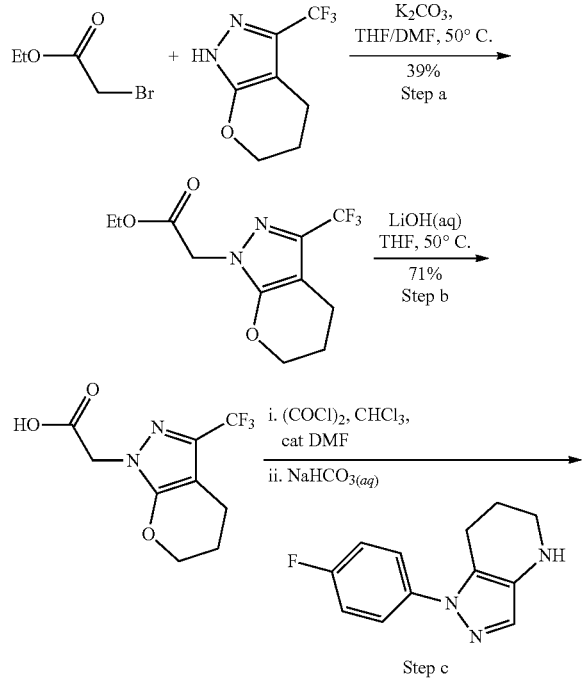

a) 3-(Trifluoromethyl)-1,4,5,6-tetrahydropyrano[2,3-c]pyrazole (96 mg, 0.5 mmol), $K_2CO_3$ (885 mg, 6.4 mmol), and 8 mL of 3:1 THF:DMF were combined and treated with 71 μL (0.64 mmol) of ethyl bromoacetate. The slurry was stirred at 50° C. overnight and the volatiles evaporated. The residue was diluted in EtOAc and $H_2O$ and the layers separated. The organic layer was washed with brine and concentrated. The residue was purified by flash chromatography (SiO2, 40 g column, eluting with 5-20% EtOAc in hexanes) to provide 70 mg (39%) of the compound as a clear oil. $^1$H NMR (400 MHz, $CDCl_3$) δ 4.73 (s, 2H), 4.31 (dd, J=5.1, 6.1 Hz, 2H), 4.23 (q, J=7.0 Hz, 2H), 2.65 (t, J=6.7 Hz, 2H), 2.00 (m, 2H), 1.28 (t, J=7.0 Hz, 3H); MS: (ES) m/z calculated for $C_{11}H_{14}F_3N_2O_3$ [M+H]$^+$ 279.1, found 279.1.

b) The ester obtained above (70 mg, 0.25 mmol) was slurried in 1 mL THF and 0.5 mL of 2 M LiOH (aq) at 50° C. After 90 minutes, the volatiles were evaporated and 2 mL of 1 M $NaHSO_4$ (aq) was added. The mixture was extracted with 2×EtOAc. The organic layer was dried on $Na_2SO_4$, filtered, and concentrated to a foamy white solid (45 mg, 71%). MS: (ES) m/z calculated for $C_9H_{10}F_3N_2O_3$ [M+H]$^+$ 251.1, found 251.1.

c) The title compound was prepared from 2-(3-(trifluoromethyl)-5,6-dihydropyrano[2,3-e]pyrazol-1(4H)-yl)acetic acid and 1-(4-fluorophenyl)-4,5,6,7-tetrahydro-1H-pyrazolo[4,3-b]pyridine using General Method B. The reaction slurry was purified by reverse phase HPLC (C18 column, acetonitrile-$H_2O$ with 0.1% TFA as eluent) to provide 32 mg (70%) of the title compound as a white foam. $^1$H NMR (400 MHz, $CDCl_3$, mixture of rotamers) δ 8.40 (s, 0.8H), 7.56 (s, 0.2H), 7.43-7.48 (m, 2H), 7.13-7.21 (m, 2H), 5.12 (s, 0.4H), 5.00 (s, 1.6H), 4.34 (dd, J=5.1, 5.1 Hz, 2H), 3.91 (m, 0.4H), 3.80 (m, 1.6H), 2.86 (t, J=6.2 Hz, 1.6H), 2.83 (t, J=6.2 Hz, 0.4H), 2.67 (t, J=6.2 Hz, 2H), 2.09 (m, 1.6H), 2.00-2.05 (m, 2.4H); MS: (ES) m/z calculated for $C_{21}H_{20}F_4N_5O_2$ [M+H]$^+$ 450.1, found 450.1.

Example 29

Synthesis of 2-[4-chloro-5-methyl-3-(trifluoromethyl)pyrazol-1-yl]-1-[1-(2,4-difluorophenyl)-6,7-dihydro-5H-pyrazolo[4,3-b]pyridin-4-yl]ethanone

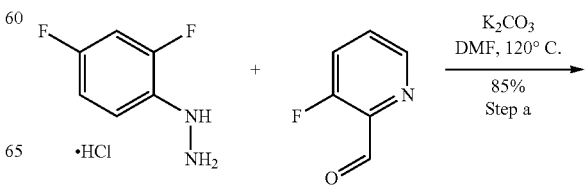

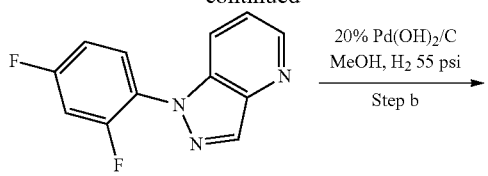

(m, 2H), 2.33 (s, 2.4H), 2.32 (s, 0.6H), 2.11 (m, 1.6H), 2.03 (m, 0.4H); MS: (ES) m/z calculated for $C_{19}H_{16}ClF_5N_5O$ [M+H]⁺ 460.1, found 460.1.

Examples 30 and 31

Synthesis of (2R)- and (2S)-2-[4-chloro-5-methyl-3-(trifluoromethyl)pyrazol-1-yl]-1-[1-(4-fluorophenyl)-6,7-dihydro-5H-pyrazolo[4,3-b]pyridin-4-yl]butan-1-one

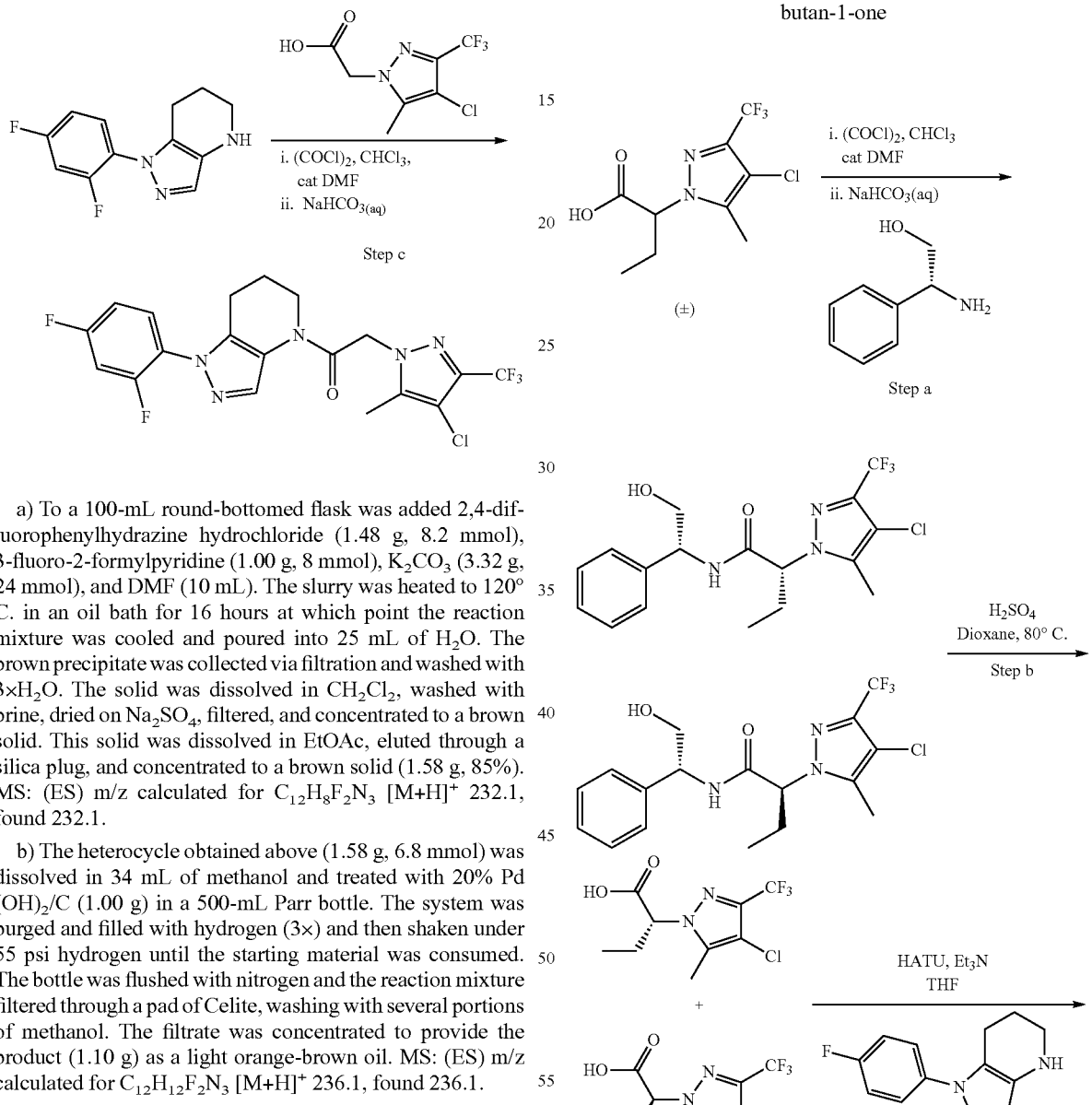

a) To a 100-mL round-bottomed flask was added 2,4-difluorophenylhydrazine hydrochloride (1.48 g, 8.2 mmol), 3-fluoro-2-formylpyridine (1.00 g, 8 mmol), $K_2CO_3$ (3.32 g, 24 mmol), and DMF (10 mL). The slurry was heated to 120° C. in an oil bath for 16 hours at which point the reaction mixture was cooled and poured into 25 mL of $H_2O$. The brown precipitate was collected via filtration and washed with 3×$H_2O$. The solid was dissolved in $CH_2Cl_2$, washed with brine, dried on $Na_2SO_4$, filtered, and concentrated to a brown solid. This solid was dissolved in EtOAc, eluted through a silica plug, and concentrated to a brown solid (1.58 g, 85%). MS: (ES) m/z calculated for $C_{12}H_8F_2N_3$ [M+H]⁺ 232.1, found 232.1.

b) The heterocycle obtained above (1.58 g, 6.8 mmol) was dissolved in 34 mL of methanol and treated with 20% Pd(OH)₂/C (1.00 g) in a 500-mL Parr bottle. The system was purged and filled with hydrogen (3×) and then shaken under 55 psi hydrogen until the starting material was consumed. The bottle was flushed with nitrogen and the reaction mixture filtered through a pad of Celite, washing with several portions of methanol. The filtrate was concentrated to provide the product (1.10 g) as a light orange-brown oil. MS: (ES) m/z calculated for $C_{12}H_{12}F_2N_3$ [M+H]⁺ 236.1, found 236.1.

c) The compound was prepared 2-(4-chloro-5-methyl-3-(trifluoromethyl)-1H-pyrazol-1-yl)acetic acid and 1-(2,4-difluorophenyl)-4,5,6,7-tetrahydro-1H-pyrazolo[4,3-b]pyridine using General Method B. The product mixture was washed with 2×1 M $NaHSO_4$. The organic layer was concentrated and the residue was purified by reverse phase HPLC (C18 column, acetonitrile-$H_2O$ with 0.1% TFA as eluent) to provide the title compound as a white foamy solid (47 mg, 70%). ¹H NMR (400 MHz, CDCl₃, mixture of rotamers) δ 8.39 (s, 0.8H), 7.64 (s, 0.2H), 7.48 (m, 2H), 7.00 (m, 2H), 5.25 (s, 0.4H), 5.14 (s, 1.6H), 3.92 (m, 0.4H), 3.85 (m, 1.6H), 2.70

-continued

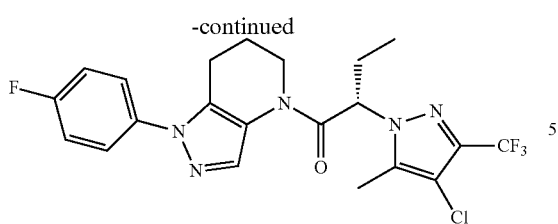

a) 2-(4-Chloro-5-methyl-3-(trifluoromethyl)-1H-pyrazol-1-yl)butanoic acid (677 mg, 2.5 mmol) was dissolved in 10 mL of $CHCl_3$ and 3 drops of DMF. Oxalyl chloride (262 µL, 3 mmol) was added dropwise, causing gas evolution. After 30 minutes, (R)-phenylglycinol (377 mg, 2.75 mmol) was added followed by 8 mL of saturated $NaHCO_3$. After 45 minutes, the reaction mixture was washed with brine and purified by flash chromatography ($SiO_2$, 40 g column, eluting with 10-70% EtOAc in hexanes). First eluting diastereomer: $^1H$ NMR (400 MHz, $CDCl_3$) δ 7.62 (d, J=7.8 Hz, 1H), 7.23-7.39 (m, 3H), 7.08-7.11 (m, 2H), 5.00-5.04 (m, 1H), 4.66 (t, J=7.4 Hz, 1H), 3.84 (m, 2H), 2.31 (t, J=7.4 Hz, 3H), 2.26 (s, 3H), 0.91 (t, J=7.0 Hz, 3H); MS: (ES) m/z calculated for $C_{17}H_{20}ClF_3N_3O_2$ $[M+H]^+$ 390.1, found 390.1. Second eluting diasteromer: $^1H$ NMR (400 MHz, $CDCl_3$) δ 7.58 (d, J=7.0 Hz, 1H), 7.38 (m, 2H), 7.32 (m, 1H), 7.23-7.25 (m, 2H), 5.00 (dt, J=5.1, 7.0 Hz, 1H), 4.69 (t, J=7.8 Hz, 1H), 3.75 (t, J=5.5 Hz, 2H), 2.32 (s, 3H), 2.10-2.27 (m, 3H), 0.84 (t, J=7.4 Hz, 3H); MS: (ES) m/z calculated for $C_{17}H_{20}ClF_3N_3O_2$ $[M+H]^+$ 390.1, found 390.1.

b) The diastereomers obtained above were independently heated to 80° C. in 0.25 M dioxane with 15 equiv of 6 M $H_2SO_4$. The reaction slurries were concentrated to approx half volume and extracted with 3×EtOAc. The organic layer was dried on $Na_2SO_4$, filtered, and concentrated to provide the desired acid products in 82-89% yield.

c) (2R)-2-[4-Chloro-5-methyl-3-(trifluoromethyl)pyrazol-1-yl]-1-[1-(4-fluorophenyl)-6,7-dihydro-5H-pyrazolo[4,3-b]pyridin-4-yl]butan-1-one and (2S)-2-[4-Chloro-5-methyl-3-(trifluoromethyl)pyrazol-1-yl]-1-[1-(4-fluorophenyl)-6,7-dihydro-5H-pyrazolo[4,3-b]pyridin-4-yl]butan-1-one: The acid obtained from the first eluting diastereomer in step a was coupled with 1-(4-fluorophenyl)-4,5,6,7-tetrahydro-1H-pyrazolo[4,3-b]pyridine using General Method A. The reaction slurry was purified by reverse phase HPLC (C18 column, acetonitrile-$H_2O$ with 0.1% TFA as eluent) to provide 73 mg (62%) of the title compound as a white solid. $^1H$ NMR (400 MHz, $CDCl_3$) δ 8.43 (s, 1H), 7.44 (m, 2H), 7.16 (m, 2H), 5.29 (dd, J=6.7, 8.6 Hz, 1H), 3.81 (ddd, J=2.7, 7.4, 10.6 Hz, 1H), 3.50 (ddd, J=2.8, 8.6, 11.8 Hz, 1H), 2.79 (dt, J=2.7, 6.3 Hz, 2H), 2.33 (m, 1H), 2.30 (s, 3H), 2.22 (m, 1H), 1.96 (m, 1H), 1.86 (m, 1H), 0.98 (t, J=7.0 Hz, 3H); MS: (ES) m/z calculated for $C_{21}H_{21}ClF_4N_5O$ $[M+H]^+$ 470.1, found 470.1. The acid obtained from the second eluting diastereomer in step a was coupled with 1-(4-fluorophenyl)-4,5,6,7-tetrahydro-1'-1-pyrazolo[4,3-b]pyridine using General Method A. The reaction slurry was purified by reverse phase HPLC (C18 column, acetonitrile-$H_2O$ with 0.1% TFA as eluent) to provide 71 mg (60%) of the title compound as a white solid. $^1H$ NMR (400 MHz, $CDCl_3$) δ 8.43 (s, 1H), 7.44 (m, 2H), 7.16 (m, 2H), 5.29 (dd, J=6.7, 8.6 Hz, 1H), 3.81 (ddd, J=2.7, 7.4, 10.6 Hz, 1H), 3.50 (ddd, J=2.8, 8.6, 11.8 Hz, 1H), 2.79 (dt, J=2.7, 6.3 Hz, 2H), 2.33 (m, 1H), 2.30 (s, 3H), 2.22 (m, 1H), 1.96 (m, 1H), 1.86 (m, 1H), 0.98 (t, J=7.0 Hz, 3H); MS: (ES) m/z calculated for $C_{21}H_{21}ClF_4N_5O$ $[M+H]^+$ 470.1, found 470.1.

Example 32

Synthesis of 1-[1-(4-fluorophenyl)-6,7-dihydro-5H-pyrazolo[4,3-b]pyridin-4-yl]-2-[1-(trifluoromethyl)imidazo[1,5-a]pyridin-3-yl]ethanone

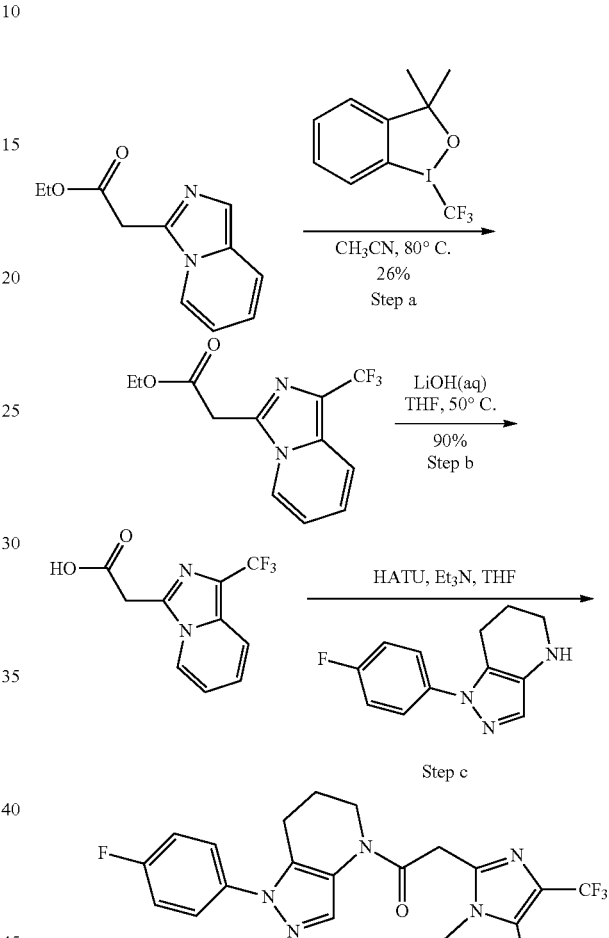

a) To ethyl 2-(imidazo[1,5-a]pyridin-3-yl)acetate (131 mg, 0.64 mmol) in $CH_3CN$ was added 3,3-dimethyl-1-(trifluoromethyl)-1,2-benziodoxole (212 mg, 0.64 mmol). The slurry was heated to 80° C. for 95 minutes then cooled to room temperature. The reaction mixture was purified by flash chromatography (SiO2, 40 g column, eluting with 15-75% EtOAc in hexanes) to provide the product (46 mg, 26%) as an orange oil that solidifies on standing. MS: (ES) m/z calculated for $C_{12}H_{12}F_3N_2O_2$ $[M+H]^+$ 273.1, found 273.0.

b) The ester obtained above (36 mg, 0.13 mmol) was slurried in 1 mL THF and 0.125 mL of 2 M LiOH (aq) at 50° C. Upon completion, the volatiles were evaporated and 500 µL of 1 M $NaHSO_4$ (aq) and 4 mL of EtOAc were added. The layers were separated and the organic phase washed with brine. The organic layer was dried on $Na_2SO_4$, filtered, and concentrated to a tan solid (29 mg, 90%). MS: (ES) m/z calculated for $C_{10}H_8F_3N_2O_2$ $[M+H]^+$ 245.1, found 245.0.

c) The title compound was prepared from 2-(1-(trifluoromethyl)imidazo[1,5-a]pyridin-3-yl)acetic acid and 1-(4-fluorophenyl)-4,5,6,7-tetrahydro-1H-pyrazolo[4,3-b]pyridine using General Method A. The reaction slurry was purified by reverse phase HPLC (C18 column, acetonitrile-H₂O with 0.1% TFA as eluent) to provide 32 mg (72%) of the title compound as a white solid. ¹H NMR (400 MHz, CDCl₃, mixture of rotamers) δ 8.36 (d, J=6.6 Hz, 1H), 8.35 (s, 0.9H), 8.06 (s, 0.1H), 7.63 (d, J=9.0 Hz, 1H), 7.50 (m, 0.3H), 7.42 (m, 1.7H), 7.12-7.22 (m, 2H), 7.01 (m, 1H), 6.79 (t, J=6.6 Hz, 1H), 4.51 (s, 0.2H), 4.38 (s, 1.8H), 4.08 (m, 1.7H), 3.90 (m, 0.3H), 2.86 (t, J=6.6 Hz, 0.3H), 2.80 (t, J=6.6 Hz, 1.7H), 2.02 (m, 2H); MS: (ES) m/z calculated for C₂₂H₁₈F₄N₅O [M+H]⁺ 444.1, found 444.1.

Example 33

Synthesis of 1-[1-(4-fluorophenyl)-5-methyl-6,7-dihydro-5H-pyrazolo[4,3-b]pyridin-4-yl]-2-[5-methyl-3-(trifluoromethyl)pyrazol-1-yl]butan-1-one

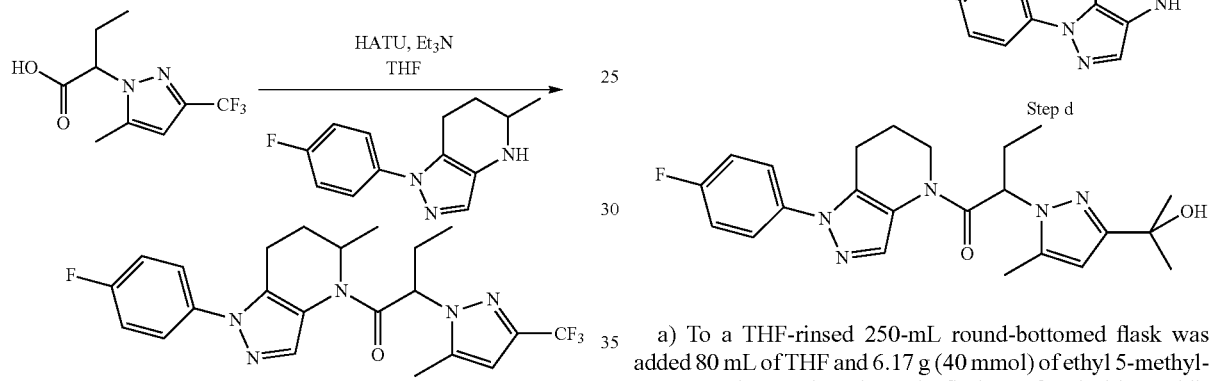

The title compound was prepared from 2-(5-methyl-3-(trifluoromethyl)-1H-pyrazol-1-yl)butanoic acid and 1-(4-fluorophenyl)-5-methyl-4,5,6,7-tetrahydro-1H-pyrazolo[4,3-b]pyridine using General Method A. The reaction slurry was purified by reverse phase HPLC (C18 column, acetonitrile-H₂O with 0.1% TFA as eluent) to provide 13 mg (46%) of the title compound as a white solid. ¹H NMR (400 MHz, CDCl₃) δ 8.40 (s, 1H), 7.47 (m, 2H), 7.16 (m, 2H), 6.35 (s, 1H), 5.37 (dd, J=6.7, 8.6 Hz, 1H), 4.63 (m, 1H), 2.86 (m, 1H), 2.73 (ddd, J=1.9, 5.1, 11.3 Hz, 1H), 2.37 (s, 3H), 2.27 (m, 2H), 1.92-1.97 (m, 2H), 0.93 (t, J=6.5 Hz, 3H), 0.57 (t, J=6.7 Hz, 3H); MS: (ES) m/z calculated for C₂₂H₂₄F₄N₅O [M+H]⁺ 450.2, found 450.2.

Example 34

Synthesis of 1-[1-(4-fluorophenyl)-6,7-dihydro-5H-pyrazolo[4,3-b]pyridin-4-yl]-2-[3-(1-hydroxy-1-methyl-ethyl)-5-methyl-pyrazol-1-yl]butan-1-one

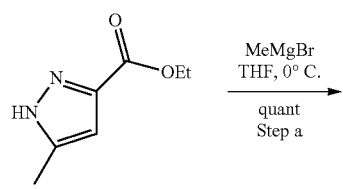

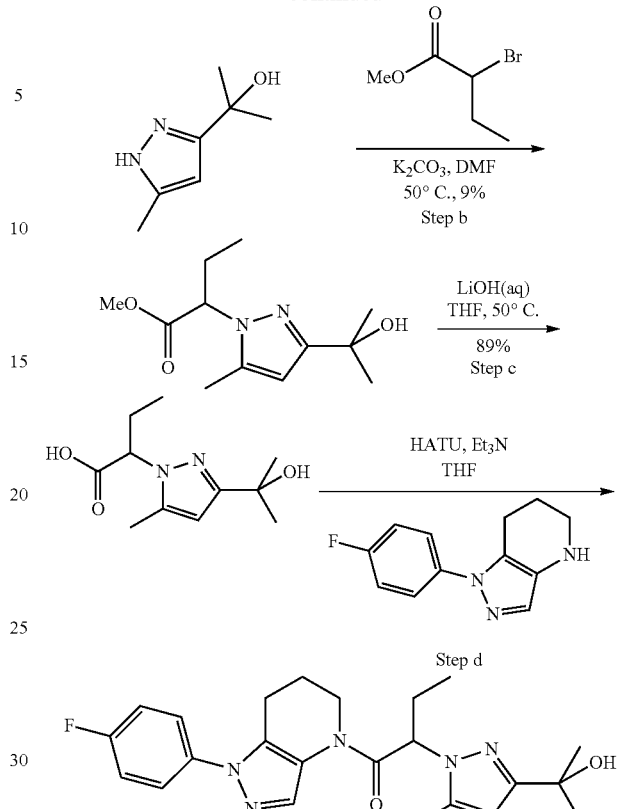

a) To a THF-rinsed 250-mL round-bottomed flask was added 80 mL of THF and 6.17 g (40 mmol) of ethyl 5-methyl-1H-pyrazole-3-carboxylate. The flask was fitted with an addition funnel and cooled in an ice bath under N₂. Methyl magnesium bromide (3 M in Et₂O, 41 mL, 124 mmol) was added dropwise. After 70 minutes, an additional 4 mL of Grignard reagent was added. At 2 hours, the reaction was quenched by the slow addition of 2 mL of 1 M NaHSO₄. The reaction slurry was acidified by the slow addition of 6 M HCl (aq). The volatiles were evaporated and the mixture extracted with 3×EtOAc. The organic layer was dried on MgSO₄, filtered, and concentrated to provide a viscous yellow-orange oil (6.0 g, quant) that solidified on standing. MS: (ES) m/z calculated for C₇H₁₃N₂O [M+H]⁺ 141.1, found 141.1.

b) Methyl bromobutyrate (1.068 g, 5.9 mmol), 2-(5-methyl-1H-pyrazol-3-yl)propan-2-ol (752 mg, 5.36 mmol), and K₂CO₃ (1.520 g, 11 mmol) were combined in 16 mL of 2:1 THF:DMF at 70° C. overnight. The reaction mixture was cooled and the solids were filtered off washing with EtOAc. The filtrate was washed with 2×H₂O and brine. The organic layer was concentrated and the residue purified by flash chromatography (SiO₂, 80 g column, eluting with 10-65% EtOAc in hexanes) to provide 114 mg (9%) of the title compound as a colorless oil. ¹H NMR (400 MHz, CDCl₃) δ 5.93 (s, 1H), 4.62 (dd, J=5.8, 9.8 Hz, 1H), 3.72 (s, 3H), 2.95 (br s, 1H), 2.29 (m, 2H), 2.24 (s, 3H), 1.52 (s, 6H), 0.85 (t, J=7.4, 3H); MS: (ES) m/z calculated for C₁₂H₂₁N₂O₃ [M+H]⁺ 241.2, found 241.2.

c) The ester obtained above (113 mg, 0.47 mmol) was slurried in 1 mL THF and 310 μL of 2 M LiOH at 50° C. After 30 minutes, the volatiles were evaporated and 1 mL of 1 M NaHSO₄ was added. The slurry was extracted with 3×EtOAc and the organic layer dried on $Na_2SO_4$, filtered, and concentrated to give a clear oil (95 mg, 89%).

d) The title compound was prepared from 2-(3-(2-hydroxypropan-2-yl)-5-methyl-1H-pyrazol-1-yl)butanoic acid and 1-(4-fluorophenyl)-4,5,6,7-tetrahydro-1H-pyrazolo[4,3-b]pyridine using General Method A. The reaction slurry was purified by reverse phase HPLC (C18 column, acetonitrile-$H_2O$ with 0.1% TFA as eluent) to provide 3.7 mg of the title compound as an off-white solid. $^1H$ NMR (400 MHz, $CDCl_3$) δ 8.46 (s, 1H), 7.44 (m, 2H), 7.15 (t, J=8.6 Hz, 2H), 5.92 (s, 1H), 5.17 (dd, J=7.4, 7.4 Hz, 1H), 3.73 (m, 1H), 3.48 (m, 1H), 2.75 (m, 2H), 2.33 (m, 1H), 2.23 (s, 3H), 2.17 (s, 1H), 2.14 (m, 1H), 1.87 (m, 1H), 1.73 (m, 1H), 1.52 (s, 6H), 0.96 (t, J=7.4 Hz, 3H); MS: (ES) m/z calculated for $C_{23}H_{29}FN_5O_2$ $[M+H]^+$ 426.2, found 426.2.

Example 35

Synthesis of 1-[1-(4-fluorophenyl)-6,7-dihydro-5H-pyrazolo[4,3-b]pyridin-4-yl]-2-(3-isopropenyl-5-methyl-pyrazol-1-yl)butan-1-one

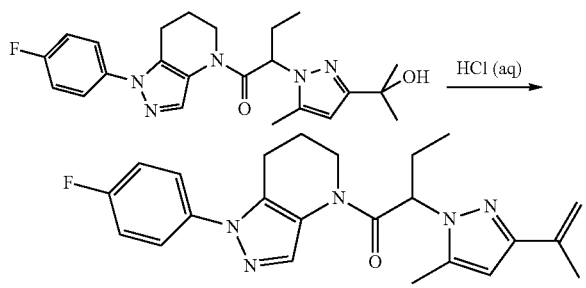

A portion of 1-[1-(4-fluorophenyl)-6,7-dihydro-5H-pyrazolo[4,3-b]pyridin-4-yl]-2-[3-(1-hydroxy-1-methyl-ethyl)-5-methyl-pyrazol-1-yl]butan-1-one was treated with 6 M HCl until complete. The reaction slurry was purified by reverse phase HPLC (C18 column, acetonitrile-$H_2O$ with 0.1% TFA as eluent) to provide 12 mg of the title compound as an off-white solid. $^1H$ NMR (400 MHz, $CDCl_3$) δ 8.47 (s, 1H), 7.44 (m, 2H), 7.14 (t, J=8.6 Hz, 2H), 6.14 (s, 1H), 5.42 (br s, 1H), 5.22 (dd, J=7.1, 8.2 Hz, 1H), 5.02 (br s, 1H), 3.80 (ddd, J=3.1, 7.8, 10.1 Hz, 1H), 3.47 (ddd, J=2.8, 9.0, 12.1 Hz, 1H), 2.74 (m, 2H), 2.33 (m, 1H), 2.23 (s, 3H), 2.15 (m, 1H), 2.10 (s, 3H) 1.87 (m, 1H), 1.78 (m, 1H), 0.98 (t, J=7.4 Hz, 3H); MS: (ES) m/z calculated for $C_{23}H_{27}FN_5O$ $[M+H]^+$ 408.2, found 408.2.

Example 36

Synthesis of 1-[1-(4-fluorophenyl)-6,7-dihydro-5H-pyrazolo[4,3-b]pyridin-4-yl]-2-[5-methyl-3-(trifluoromethyl)pyrazol-1-yl]propan-1-one

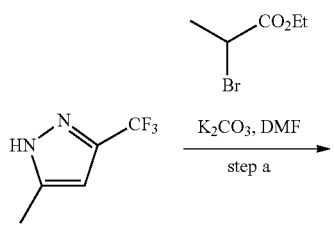

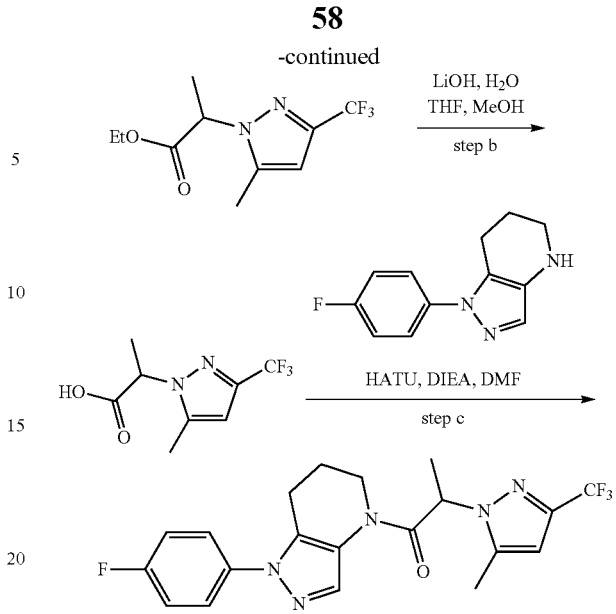

a) A mixture of potassium carbonate (922 mg, 6.67 mmol), 2-methyl-5-(trifluoromethyl)-1H-pyrazole (500 mg, 3.33 mmol) and ethyl 2-bromopropanoate (0.48 mL, 3.7 mmol) in dimethylformamide:tetrahydrofuran (3 mL:6 mL) was heated at 60° C. for 5 h with stirring. After cooling to room temperature, most of tetrahydrofuran was removed by gently blowing nitrogen over the reaction mixture. Ethyl acetate and water were added and the layers were separated. The aqueous layer was extracted twice more with ethyl acetate. The combined organic layers were dried ($Na_2SO_4$), filtered, and concentrated in vacuo. The crude residue was purified by flash chromatography ($SiO_2$, 10-20% ethyl acetate in hexanes) to afford the desired product (735 mg, 2.94 mmol, 88%).

b) Ethyl 2-[5-methyl-3-(trifluoromethyl)pyrazol-1-yl]propanoate (734 mg, 2.94 mmol) was dissolved in tetrahydrofuran (4 mL) at room temperature. Aqueous lithium hydroxide solution (1.5 N, 2 mL, 3.0 mmol) was added followed by methanol (~2 mL) to make a uniform solution. After 2 h, most of tetrahydrofuran and methanol was removed by gently blowing nitrogen over reaction mixture. Aqueous hydrochloric acid (5 N, 0.6 mL, 3.0 mmol) was added to the reaction mixture and the product was extracted with dichloromethane three times. The combined organic layers were dried over anhydrous sodium sulfate and concentrated under reduced pressure to give the crude product (625 mg, 2.82 mmol, 96%) as a white solid which was used without further purification.

c) Dimethylformamide (1 mL) was added to a mixture containing 2-[5-methyl-3-(trifluoromethyl)pyrazol-1-yl]propanoic acid (49.6 mg, 0.223 mmol) and HATU (89.1 mg, 0.234 mmol). Diisopropylethylamine (98 µL, 0.56 mmol) was added at room temperature and the reaction mixture was stirred for 1 minute. 1-(4-Fluorophenyl)-4,5,6,7-tetrahydropyrazolo[4,3-b]pyridine (49.5 mg, 0.228 mmol) was added all at once and the reaction mixture was stirred at room temperature overnight. Ethyl acetate and water were then added and the layers were separated. The aqueous layer was extracted twice more with ethyl acetate. The combined organic layers were dried ($Na_2SO_4$), filtered, and concentrated in vacuo. The crude residue was purified by flash chromatography ($SiO_2$, 20-38% ethyl acetate in hexanes) to afford the desired product as a white solid (83.5 mg, 0.198 mmol, 89%). $^1H$ NMR (400 MHz, $CDCl_3$) δ 8.45 (s, 1H), 7.44 (ddd, J=9.2, 5.2, 2.0 Hz, 2H), 7.15 (dt, J=8.8, 2.0 Hz, 2H), 6.31 (s, 1H), 5.55 (q, J=7.2 Hz, 1H), 3.73 (ddd, J=13, 7.6, 3.2 Hz, 1H), 3.37 (ddd, J=12, 8.8, 3.2 Hz, 1H), 2.72-2.79 (m, 2H), 2.29 (s, 3H), 1.86-1.97 (m, 1H), 1.76-1.85 (m, 1H), 1.80 (d, J=7.2 Hz, 3H); MS: (ES) m/z calculated for $C_{20}H_{19}N_5OF_4$ [M+H]$^+$ 422, found 422.

Example 37

Synthesis of 1-[1-(4-fluorophenyl)-6,7-dihydro-5H-pyrazolo[4,3-b]pyridin-4-yl]-2-[5-methyl-3-(trifluoromethyl)pyrazol-1-yl]butan-1-one

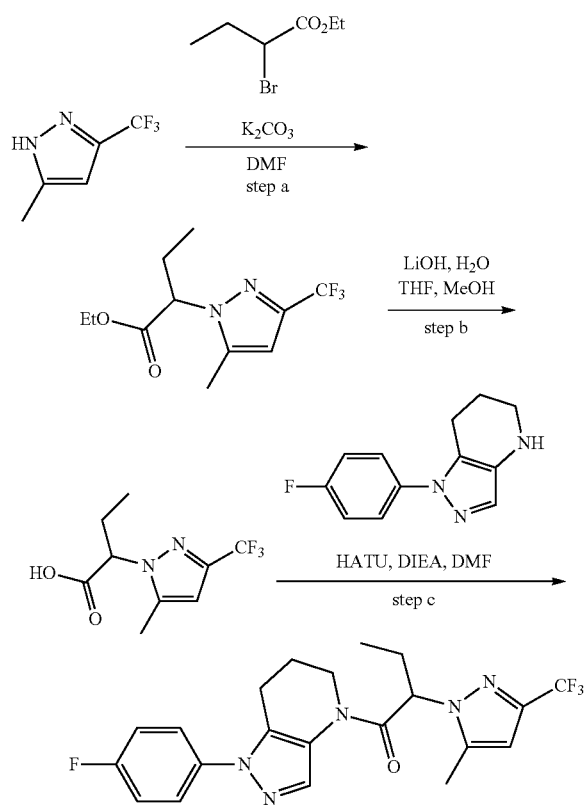

a) A mixture of potassium carbonate (924 mg, 6.69 mmol), 2-methyl-5-(trifluoromethyl)-1H-pyrazole (501 mg, 3.34 mmol) and methyl 2-bromobutyrate (0.42 mL, 3.7 mmol) in dimethylformamide:tetrahydrofuran (3 mL:6 mL) was heated at 60° C. for 5 h with stirring. After cooling to room temperature, most of tetrahydrofuran was removed by gently blowing nitrogen over the reaction mixture. Ethyl acetate and water were added and the layers were separated. The aqueous layer was extracted twice more with ethyl acetate. The combined organic layers were dried ($Na_2SO_4$), filtered, and concentrated in vacuo. The crude residue was purified by flash chromatography ($SiO_2$, 12-17% ethyl acetate in hexanes) to afford the desired product (704 mg, 2.81 mmol, 84%).

b) Methyl 2-[5-methyl-3-(trifluoromethyl)pyrazol-1-yl]butyrate (703 mg, 2.81 mmol) was dissolved in tetrahydrofuran (4 mL) at room temperature. Aqueous lithium hydroxide solution (1.5 N, 2 mL, 3.0 mmol) was added followed by methanol (~2 mL) to make a uniform solution. After 2 h, most of tetrahydrofuran and methanol was removed by gently blowing nitrogen over reaction mixture. Aqueous hydrochloric acid (5 N, 0.6 mL, 3.0 mmol) was added to the reaction mixture and the mixture was extracted with dichloromethane three times. The combined organic layers were dried over anhydrous sodium sulfate and concentrated under reduced pressure which yielded the crude product (661 mg, 2.80 mmol, 100%) as a white solid which was used without further purification.

c) Dimethylformamide (0.7 mL) was added to a mixture containing 2-[5-methyl-3-(trifluoromethyl)pyrazol-1-yl]butyric acid (50.5 mg, 0.214 mmol) and HATU (84.1 mg, 0.221 mmol). Diisopropylethylamine (92 µL, 0.53 mmol) was added at room temperature and the reaction mixture was stirred for 1 minute. 1-(4-Fluorophenyl)-4,5,6,7-tetrahydropyrazolo[4,3-b]pyridine (44.1 mg, 0.203 mmol) was then added all at once and the reaction mixture was stirred at room temperature overnight. Ethyl acetate and water were added and the layers were separated. The aqueous layer was extracted twice more with ethyl acetate. The combined organic layers were dried ($Na_2SO_4$), filtered, and concentrated in vacuo. The crude residue was purified by flash chromatography ($SiO_2$, 17-33% ethyl acetate in hexanes) to afford the desired product as a white solid (80.9 mg, 0.186 mmol, 92%). $^1$H NMR (400 MHz, $CDCl_3$) δ 8.44 (s, 1H), 7.44 (ddd, J=8.8, 5.2, 2.0 Hz, 2H), 7.15 (ddd, J=8.4, 8.4, 2.0 Hz, 2H), 6.30 (s, 1H), 5.32 (dd, J=8.4, 6.8 Hz, 1H), 3.78 (ddd, J=12, 7.2, 2.8 Hz, 1H), 3.47 (ddd, J=12, 8.8, 3.2 Hz, 1H), 2.69-2.81 (m, 2H), 2.31 (s, 3H), 2.18-2.38 (m, 2H), 1.88-1.97 (m, 1H), 1.74-1.83 (m, 1H), 0.98 (t, J=7.2 Hz, 3H); MS: (ES) m/z calculated for $C_{21}H_{21}N_5OF_4$ [M+H]$^+$ 436, found 436.

Example 38

Synthesis of 1-[1-(4-fluorophenyl)-6,7-dihydro-5H-pyrazolo[4,3-b]pyridin-4-yl]-2-[2-methyl-4-(trifluoromethyl)imidazol-1-yl]propan-1-one

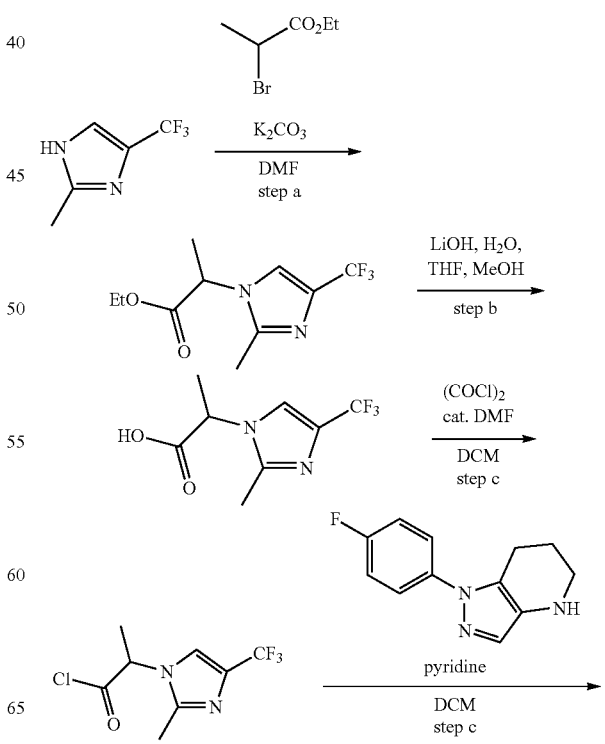

-continued

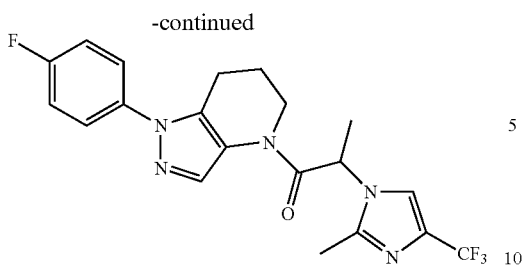

a) A mixture of potassium carbonate (832 mg, 6.02 mmol), 2-methyl-5-(trifluoromethyl)-1H-imidazole (450 mg, 3.00 mmol) and ethyl 2-bromopropanoate (0.43 mL, 3.3 mmol) in dimethylformamide:tetrahydrofuran (2 mL:4 mL) was heated at 50° C. for 7 h with stirring and then at room temperature overnight. Most of the tetrahydrofuran was removed by gently blowing nitrogen over the reaction mixture. Ethyl acetate and water were then added and the layers were separated. The aqueous layer was extracted twice more with ethyl acetate. The combined organic layers were dried ($Na_2SO_4$), filtered, and concentrated in vacuo. The crude residue was purified by flash chromatography ($SiO_2$, 17-50% ethyl acetate in hexanes) to afford the desired product (697 mg, 2.79 mmol, 93%).

b) Ethyl 2-[2-methyl-4-(trifluoromethyl)imidazol-1-yl]propanoate (697 mg, 2.79 mmol) was dissolved in tetrahydrofuran (5 mL) at room temperature. Aqueous lithium hydroxide solution (1.5 N, 2.5 mL, 3.8 mmol) was added followed by methanol (~2 mL) to make a uniform solution. After 2 h, most of tetrahydrofuran and methanol were removed by gently blowing nitrogen over reaction mixture. Aqueous hydrochloric acid (5 N, 0.75 mL, 3.8 mmol) was added to the reaction mixture and the product was extracted with dichloromethane three times. The combined organic layers were dried over anhydrous sodium sulfate and concentrated under reduced pressure which yielded the crude product (562 mg, 2.52 mmol, 91%) as white foam which was used without further purification.

c) 2-[2-Methyl-4-(trifluoromethyl)imidazol-1-yl]propanoic acid (151 mg, 0.679 mmol) was dissolved in dichloromethane (2 mL) at room temperature. Oxalyl chloride (120 µL, 1.38 mmol) and a catalytic amount of dimethylformamide (1 µL) was added and the reaction was stirred at room temperature for 2 h. Solvent was removed under reduced pressure and the acid chloride was dried under vacuum. The crude acid chloride was dissolved in dichloromethane (2.1 mL). To a portion of this solution (0.7 mL, 0.22 mmol) was added 1-(4-fluorophenyl)-4,5,6,7-tetrahydropyrazolo[4,3-b]pyridine (41.5 mg, 0.191 mmol) and pyridine (55 µL, 0.68 mmol) at room temperature and the reaction mixture was stirred for 2 h. Water was added and the layers were separated. The aqueous layer was extracted twice more with dichloromethane. The combined organic layers were dried ($Na_2SO_4$), filtered, and concentrated in vacuo. The crude residue was purified by flash chromatography ($SiO_2$, 40-100% ethyl acetate in hexanes with 0.1% aqueous ammonium hydroxide) to afford the desired product as a white solid (70.1 mg, 0.166 mmol, 87%). $^1$H NMR (400 MHz, $CDCl_3$) δ 8.44 (s, 1H), 7.45 (ddd, J=9.2, 4.8, 2.0 Hz, 2H), 7.17 (dt, J=9.2, 2.0 Hz, 2H), 5.21 (q, J=6.8 Hz, 1H), 3.75 (ddd, J=12, 7.2, 3.2 Hz, 1H), 3.51 (ddd, J=12, 8.0, 3.2 Hz, 1H), 2.84 (t, J=6.6 Hz, 2H), 2.47 (s, 3H), 1.96-2.09 (m, 2H), 1.72 (d, J=6.4 Hz, 3H); MS: (ES) m/z calculated for $C_{20}H_{19}N_5OF_4$ [M+H]$^+$ 422, found 422.

Example 39

Synthesis of 1-[1-(4-fluorophenyl)-6,7-dihydro-5H-pyrazolo[4,3-b]pyridin-4-yl]-2-[2-methyl-4-(trifluoromethyl)imidazol-1-yl]butan-1-one

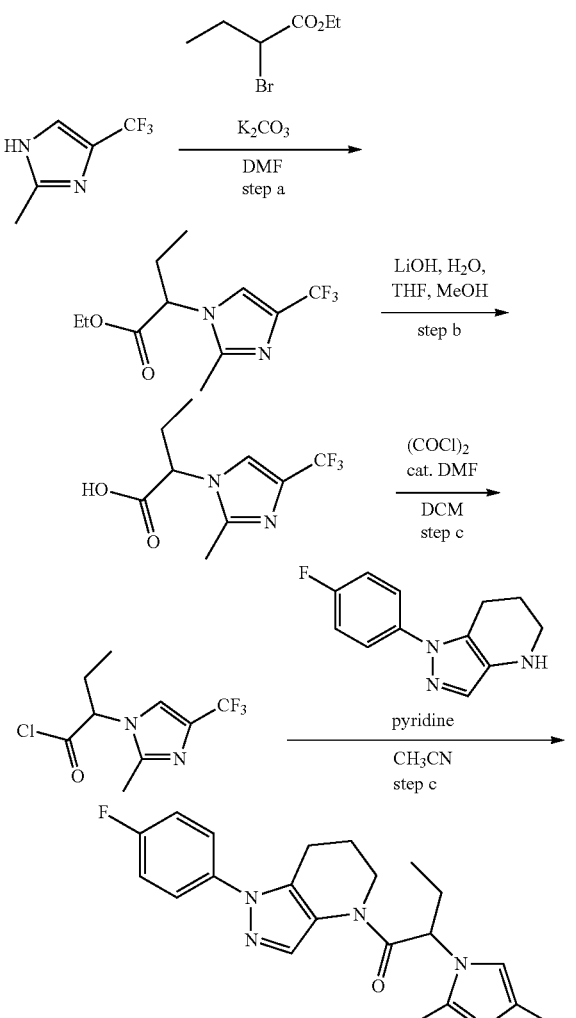

a) A mixture of potassium carbonate (834 mg, 6.04 mmol), 2-methyl-5-(trifluoromethyl)-1H-imidazole (449 mg, 2.99 mmol) and methyl 2-bromobutyrate (0.38 mL, 3.3 mmol) in dimethylformamide:tetrahydrofuran (2 mL:4 mL) was heated at 50° C. for 7 h with stirring and then at room temperature overnight. Most of the tetrahydrofuran was then removed by gently blowing nitrogen over the reaction mixture. Ethyl acetate and water were added and the layers were separated. The aqueous layer was extracted twice more with ethyl acetate. The combined organic layers were dried ($Na_2SO_4$), filtered, and concentrated in vacuo. The crude residue was purified by flash chromatography ($SiO_2$, 20-50% ethyl acetate in hexanes) to afford the desired product (641 mg, 2.56 mmol, 86%).

b) Methyl 2-[2-methyl-4-(trifluoromethyl)imidazol-1-yl]butyrate (641 mg, 2.56 mmol) was dissolved in tetrahydrofuran (5 mL) at room temperature. Aqueous lithium hydroxide solution (1.5 N, 2.2 mL, 3.3 mmol) was added followed by methanol (~2 mL) to make a uniform solution. After 2 h, most of tetrahydrofuran and methanol was removed by gently blowing nitrogen over the reaction mixture. Aqueous hydrochloric acid (5 N, 0.66 mL, 3.3 mmol) was added to the reaction mixture and the product was extracted with dichloromethane three times. The combined organic layers were dried over anhydrous sodium sulfate and concentrated under reduced pressure which yielded the crude product (497 mg, 2.11 mmol, 82%) as a white foam which was used without further purification.

c) 2-[2-Methyl-4-(trifluoromethyl)imidazol-1-yl]butyric acid (149 mg, 0.632 mmol) was dissolved in dichloromethane (2 mL) at room temperature. Oxalyl chloride (110 μL, 1.26 mmol) and a catalytic amount of dimethylformamide (1 μL) was added and the reaction was stirred at room temperature for 2 h. Solvent was removed under reduced pressure and the acid chloride was dried under vacuum. The crude acid chloride was dissolved in acetonitrile (1.5 mL). To a portion of this solution (0.5 mL, 0.21 mmol) was added 1-(4-fluorophenyl)-4,5,6,7-tetrahydropyrazolo[4,3-b]pyridine (38.7 mg, 0.178 mmol) and pyridine (55 μL, 0.68 mmol) at room temperature and the reaction mixture was stirred for 2 h. Water and ethyl acetate were then added and the layers were separated. The aqueous layer was extracted twice more with ethyl acetate. The combined organic layers were dried (Na$_2$SO$_4$), filtered, and concentrated in vacuo. The crude residue was purified by flash chromatography (SiO$_2$, 50~80% ethyl acetate in hexanes with 0.1% aqueous ammonium hydroxide) to afford the desired product contaminated with some 2-[2-methyl-4-(trifluoromethyl)imidazol-1-yl]butyric acid. The product was dissolved in ethyl acetate and washed once with 1N aqueous sodium hydroxide solution. Drying over anhydrous sodium sulfate followed by filtration and removal of solvent under reduced pressure and drying under vacuum afforded the desired product as a white solid (60.4 mg, 0.139 mmol, 78%). $^1$H NMR (400 MHz, CDCl$_3$) δ 8.20 (s, 1H), 7.84 (d, J=1.2 Hz, 1H), 7.58 (ddd, J=9.2, 5.2, 2.0 Hz, 2H), 7.35 (ddd, J=9.2, 8.4, 0.8 Hz, 2H), 5.47 (dd, J=9.2, 5.6 Hz, 1H), 3.81-3.98 (m, 2H), 2.84 (t, J=6.2 Hz, 2H), 2.34 (s, 3H), 2.03-2.11 (m, 2H), 1.96-2.01 (m, 2H), 0.85 (t, J=7.2 Hz, 3H); MS: (ES) m/z calculated for C$_{21}$H$_{21}$N$_5$OF$_4$ [M+H]$^+$ 436, found 436.

Example 40

Synthesis of 1-[1-(4-fluorophenyl)-6,7-dihydro-5H-pyrazolo[4,3-b]pyridin-4-yl]-2-[4-(trifluoromethoxy)phenyl]ethanone

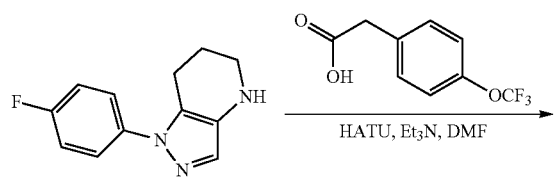

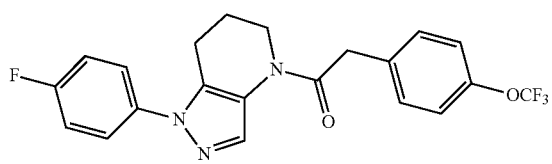

To a mixture of 1-(4-fluorophenyl)-4,5,6,7-tetrahydro-1H-pyrazolo[4,3-b]pyridine (0.023 g, 0.10 mmol), 4-(trifluoromethoxy)phenylacetic acid (0.025 g, 0.11 mmol) and Et$_3$N (0.060 mL, 0.43 mmol) in DMF (0.6 mL) was added HATU (0.060 g, 0.15 mmol). The mixture was stirred at rt for 30 min. It was then quenched with water. The mixture was partitioned between EtOAc (50 mL) and sat. NaHCO$_3$ (30 mL). The organic layer was separated, dried over Na$_2$SO$_4$, concentrated in vacuo, and purified by reverse phase HPLC to afford the desired product (0.040 g, 95%). $^1$H NMR (400 MHz, CDCl$_3$) δ 8.51 (s, 1H), 7.43 (m, 2H), 7.30 (m, 2H), 7.18 (m, 4H), 3.91 (s, 2H), 3.76 (m, 2H), 2.79 (t, J=6.4 Hz, 2H), 2.00 (m, 2H); MS: (ES) m/z calculated for C$_{21}$H$_{17}$F$_4$N$_3$O$_2$ [M+H]$^+$ 420.1, found 420.1.

Example 41

Synthesis of 2-[4-chloro-3-(trifluoromethoxy)phenyl]-1-[1-(4-fluorophenyl)-6,7-dihydro-5H-pyrazolo[4,3-b]pyridin-4-yl]ethanone

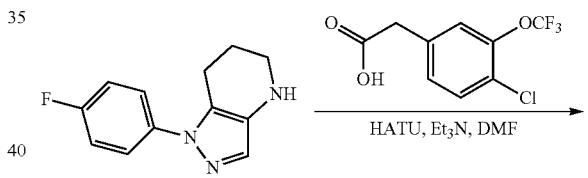

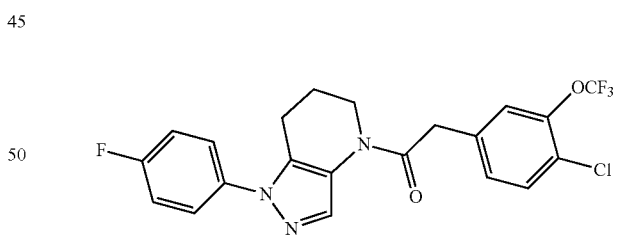

To a mixture of 1-(4-fluorophenyl)-4,5,6,7-tetrahydro-1H-pyrazolo[4,3-b]pyridine (0.023 g, 0.10 mmol), 4-chloro-3-(trifluoromethoxy)phenylacetic acid (0.025 g, 0.10 mmol) and Et$_3$N (0.060 mL, 0.43 mmol) in DMF (0.6 mL) was added HATU (0.060 g, 0.15 mmol). The mixture was stirred at rt for 30 min. It was then quenched with water and partitioned between EtOAc (50 mL) and sat. NaHCO$_3$ (30 mL). The organic layer was separated, dried over Na$_2$SO$_4$, concentrated in vacuo and purified by reverse phase HPLC to afford the desired product (0.039 g, 85%). $^1$H NMR (400 MHz, CDCl$_3$) δ 8.47 (s, 1H), 7.44 (m, 3H), 7.12-7.22 (m, 4H), 3.90 (s, 2H), 3.76 (m, 2H), 2.80 (t, J=6.2 Hz, 2H), 2.02 (m, 2H); MS: (ES) m/z calculated for $C_{21}H_{16}ClF_4N_3O_2$ [M+H]$^+$ 454.1, found 454.1.

Example 42

Synthesis of 2-[4-chloro-3-(trifluoromethyl)phenyl]-1-[1-(4-fluorophenyl)-6,7-dihydro-5H-pyrazolo[4,3-b]pyridin-4-yl]-2-methyl-propan-1-one

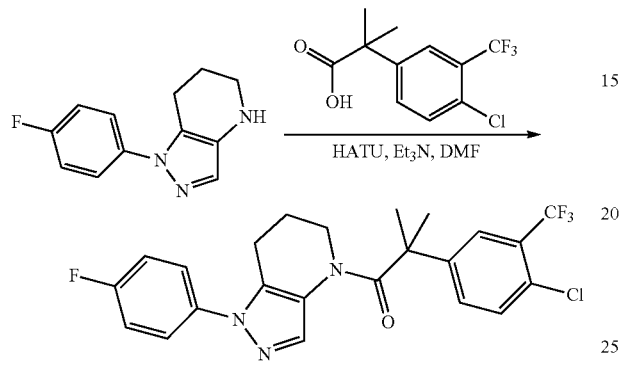

To a mixture of 1-(4-fluorophenyl)-4,5,6,7-tetrahydro-1H-pyrazolo[4,3-b]pyridine (0.030 g, 0.11 mmol), 2-[4-chloro-3-(trifluoromethyl)phenyl]-2-methyl-propanoic acid (0.030 g, 0.11 mmol) and NEt$_3$ (0.070 mL, 0.50 mmol) in DMF (0.6 mL) was added HATU (0.060 g, 0.15 mmol). The mixture was stirred at rt for 30 min. It was then quenched with water, and partitioned between EtOAc (50 mL) and sat. NaHCO$_3$ (30 mL). The organic layer was separated, dried over Na$_2$SO$_4$, concentrated in vacuo and purified by reverse phase HPLC to afford the desired product (0.005 g, 10%). $^1$H NMR (400 MHz, CDCl$_3$) δ 8.50 (s, 1H), 7.60 (d, J=2.0 Hz, 1H), 7.30-7.51 (m, 4H), 7.14 (dd, J=8.8, 8.4 Hz, 2H), 3.22 (m, 2H), 2.69 (t, J=6.4 Hz, 2H), 1.64 (s, 6H); 1.62 (m, 2H); MS: (ES) m/z calculated for $C_{23}H_{20}ClF_4N_3O$ [M+H]$^+$ 466.1, found 466.1.

Example 43

Synthesis of 2-(4-chloropyrazol-1-yl)-1-[1-(4-fluorophenyl)-6,7-dihydro-5H-pyrazolo[4,3-b]pyridin-4-yl]ethanone

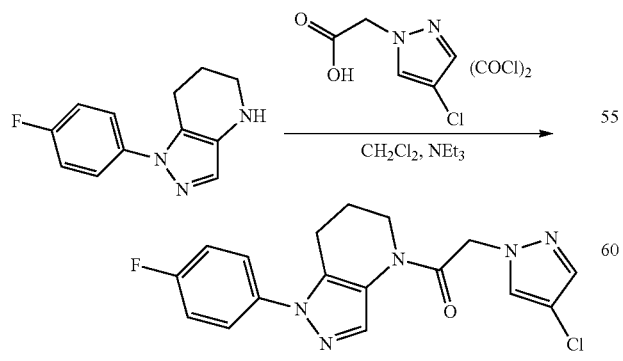

A mixture of 2-[(4-chloro-pyrazol-1-yl)]acetic acid (0.050 g, 0.31 mmol), (COCl)$_2$ (0.060 mL, 0.70 mmol) and DMF (1 drop) in CH$_2$Cl$_2$ (1 mL) was stirred for 30 min at rt. It was then evaporated to dryness on a high vacuum pump. The obtained oil was added to a mixture containing 1-(4-fluorophenyl)-4,5,6,7-tetrahydro-1H-pyrazolo[4,3-b]pyridine (0.020 g, 0.092 mmol) and NEt$_3$ (0.070 mL, 0.50 mmol) in CH$_2$Cl$_2$ (1 mL). The resulting mixture was then stirred at rt for 30 min. It was then quenched with water and partitioned between EtOAc (50 mL) and sat. NaHCO$_3$ (30 mL). The organic layer was separated, dried over Na$_2$SO$_4$, concentrated in vacuo, and purified by reverse phase HPLC to afford the desired product (0.012 g, 36%). $^1$H NMR (400 MHz, CDCl$_3$) δ 8.41 (s, 1H), 7.60 (s, 1H), 7.51 (s, 1H), 7.44 (dd, J=8.8, 4.6 Hz, 2H), 7.17 (dd, J=9.2, 8.8 Hz, 2H), 5.16 (s, 2H), 3.82 (m, 2H), 2.85 (t, J=6.2 Hz, 2H), 2.09 (m, 2H); MS: (ES) m/z calculated for $C_{17}H_{15}ClFN_5O$ [M+H]$^+$ 360.1, found 360.1.

Example 44

Synthesis of 2-[4-chloro-3-(difluoromethyl)-5-methyl-pyrazol-1-yl]-1-[1-(4-fluorophenyl)-6,7-dihydro-5H-pyrazolo[4,3-b]pyridin-4-yl]ethanone

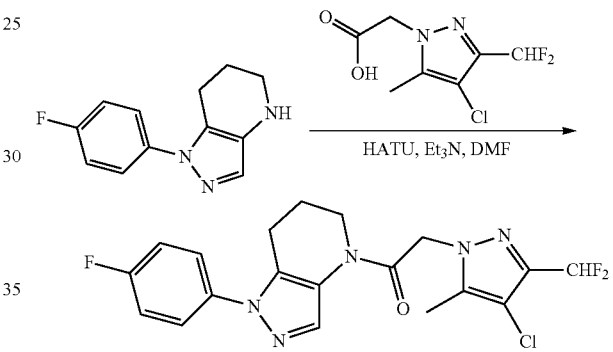

To a mixture of 1-(4-fluorophenyl)-4,5,6,7-tetrahydro-1H-pyrazolo[4,3-b]pyridine (0.023 g, 0.10 mmol), 2-(4-chloro-3-difluoromethyl-5-methyl-pyrazol-1-yl)acetic acid (0.023 g, 0.10 mmol) and NEt$_3$ (0.065 mL, 0.46 mmol) in DMF (0.6 mL) was added HATU (0.060 g, 0.15 mmol). The mixture was stirred at rt for 30 min. It was then quenched with water and partitioned between EtOAc (50 mL) and sat. NaHCO$_3$ (30 mL). The organic layer was separated, dried over Na$_2$SO$_4$, concentrated in vacuo and purified by reverse phase HPLC to afford the desired product (0.032 g, 75%). $^1$H NMR (400 MHz, CDCl$_3$) δ 8.36 (s, 1H), 7.44 (m, 2H), 7.16 (dd, J=8.8, 8.4 Hz, 2H), 6.67 (d, J=54 Hz, 1H), 5.11 (s, 2H), 3.83 (m, 2H), 2.85 (t, J=6.2 Hz, 2H), 2.30 (s, 3H), 2.10 (m, 2H); MS: (ES) m/z calculated for $C_{19}H_{17}ClF_3N_5O$ [M+H]$^+$ 424.1, found 424.1.

Example 45

Synthesis of 2-[4-chloro-3-(trifluoromethyl)pyrazol-1-yl]-1-[1-(4-fluorophenyl)-6,7-dihydro-5H-pyrazolo[4,3-b]pyridin-4-yl]ethanone

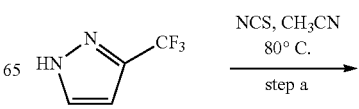

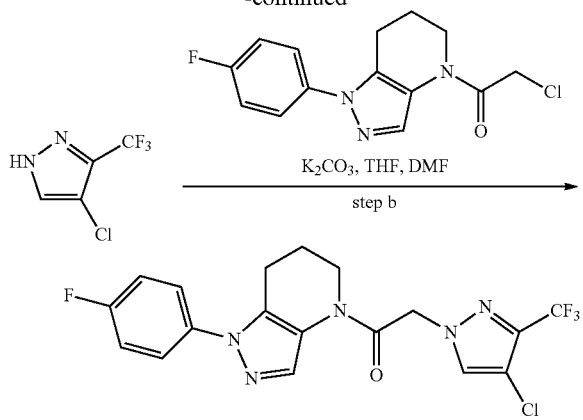

a) A mixture of 3-(trifluoromethyl)pyrazole (1.58 g, 11.6 mmol) and NCS (1.55 g, 11.6 mmol) in CH$_3$CN (20 mL) was heated at 80° C. for 3 hrs. It was then cooled to rt, evaporated in vacuo, and purified by flash chromatography (SiO$_2$) with a gradient elution of 0 to 15% EtOAc/CH$_2$Cl$_2$ to afford 4-chloro-3-(trifluoromethyl)pyrazole (1.52 g, 77%).

b) A mixture of 4-chloro-3-(trifluoromethyl)pyrazole (0.026 g, 0.15 mmol), 2-chloro-1-[1-(4-fluorophenyl)-6,7-dihydro-5H-pyrazolo[4,3-b]pyridine-4-yl]ethanone (0.045 g, 0.15 mmol) and K$_2$CO$_3$ (0.043 g, 0.31 mmol) in THF (0.6 mL) and DMF (0.3 mL) was heated at 60° C. for 1 hr. It was then cooled to rt. The mixture was partitioned between EtOAc (50 mL) and sat. NaHCO$_3$ (30 mL). The organic layer was separated, dried over Na$_2$SO$_4$, concentrated in vacuo and purified by flash chromatography on SiO$_2$ with a gradient elution of 0-60% EtOAc/hexanes to afford the desired product (0.056 g, 87%). $^1$H NMR (400 MHz, CDCl$_3$) δ 8.37 (s, 1H), 7.70 (s, 1H), 7.45 (m, 2H), 7.16 (dd, J=8.4, 8.4 Hz, 2H), 5.17 (s, 2H), 3.81 (m, 2H), 2.87 (t, J=6.2 Hz, 2H), 2.12 (m, 2H); MS: (ES) m/z calculated for C$_{18}$H$_{14}$ClF$_4$N$_5$O [M+H]$^+$ 428.1, found 428.1.

Example 46

Synthesis of 1-[1-(4-fluorophenyl)-6,7-dihydro-5H-pyrazolo[4,3-b]pyridin-4-yl]-2-[3-(trifluoromethyl)pyrazol-1-yl]ethanone

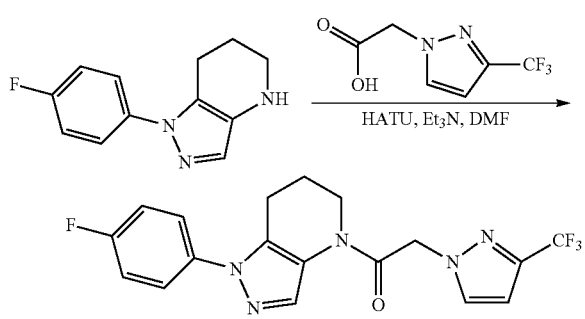

To a mixture of 1-(4-fluorophenyl)-4,5,6,7-tetrahydro-1H-pyrazolo[4,3-b]pyridine (0.026 g, 0.12 mmol), 2-(3-(trifluoromethyl)-pyrazol-1-yl)acetic acid (0.024 g, 0.12 mmol) and NEt$_3$ (0.060 mL, 0.43 mmol) in DMF (0.5 mL) was added HATU (0.060 g, 0.15 mmol). The mixture was stirred at rt for 30 min. It was then quenched with water. The mixture was partitioned between EtOAc (50 mL) and sat. NaHCO$_3$ (30 mL). The organic layer was separated, dried over Na$_2$SO$_4$, concentrated in vacuo and purified by reverse phase HPLC to afford the desired product (0.035 g, 74%). $^1$H NMR (400 MHz, CDCl$_3$) δ 8.38 (s, 1H), 7.64 (m, 1H), 7.43 (m, 2H), 7.15 (dd, J=8.8, 8.4 Hz, 2H), 6.62 (d, J=2.4 Hz, 1H), 5.23 (s, 2H), 3.82 (m, 2H), 2.84 (t, J=6.4 Hz, 2H), 2.08 (m, 2H); MS: (ES) m/z calculated for C$_{18}$H$_{15}$F$_4$N$_5$O [M+H]$^+$ 394.1, found 394.1.

Example 47

Synthesis of 2-(4-chloro-5-methyl-pyrazol-1-yl)-1-[1-(4-fluorophenyl)-6,7-dihydro-5H-pyrazolo[4,3-b]pyridin-4-yl]ethanone

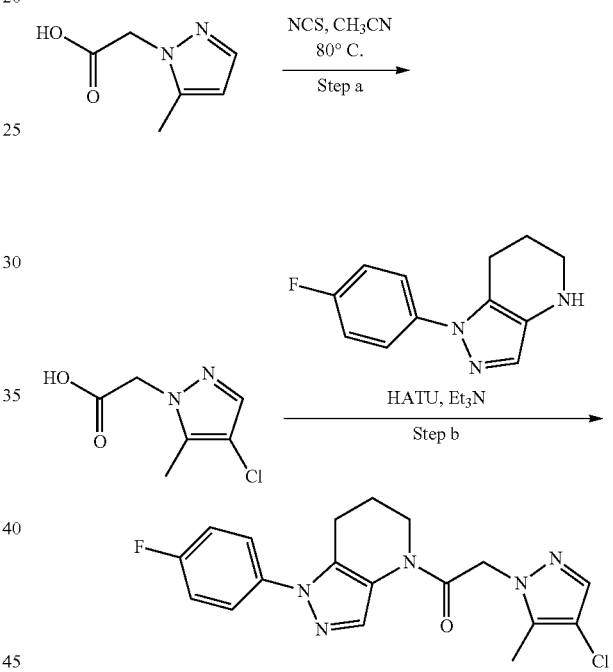

a) A mixture of 2-(5-methylpyrazol-1-yl)acetic acid (0.700 g, 5 mmol) and NCS (0.668 g, 5 mmol) in CH$_3$CN (10 mL) was heated at 80° C. for 1.5 hrs. It was then cooled to rt, evaporated in vacuo, and purified by flash chromatography (SiO$_2$, with a gradient elution of 0-20% MeOH/CH$_2$Cl$_2$) to afford 2-(4-chloro-5-methylpyrazol-1-yl)acetic acid (0.870 g, 100%).

b) To a mixture of 1-(4-fluorophenyl)-4,5,6,7-tetrahydro-1H-pyrazolo[4,3-b]pyridine (0.026 g, 0.12 mmol), 3-(trifluoromethyl)-pyrazol-1-yl)acetic acid (0.024 g, 0.12 mmol) and NEt$_3$ (0.060 mL, 0.43 mmol) in DMF (0.5 mL) was added HATU (0.060 g, 0.15 mmol). The mixture was stirred at rt for 30 min. It was then quenched with water. The mixture was partitioned between EtOAc (50 mL) and sat. NaHCO$_3$ (30 mL). The organic layer was separated, dried over Na$_2$SO$_4$, concentrated in vacuo and purified by reverse phase HPLC to afford the desired product (0.025 g, 55%). $^1$H NMR (400 MHz, CDCl$_3$) δ 8.40 (s, 1H), 7.48 (s, 1H), 7.44 (dd, J=8.8, 4.6 Hz, 2H), 7.16 (dd, J=8.4, 8.4 Hz, 2H), 5.16 (s, 2H), 3.84 (m, 2H), 2.84 (t, J=6.4 Hz, 2H), 2.29 (s, 3H), 2.10 (m, 2H); MS: (ES) m/z calculated for $C_{18}H_{17}ClFN_5O$ [M+H]$^+$ 374.1, found 374.1.

Example 48

Synthesis of 1-[1-(4-fluorophenyl)-6,7-dihydro-5H-pyrazolo[4,3-b]pyridin-4-yl]-2-[4-(trifluoromethyl) pyrazol-1-yl]ethanone

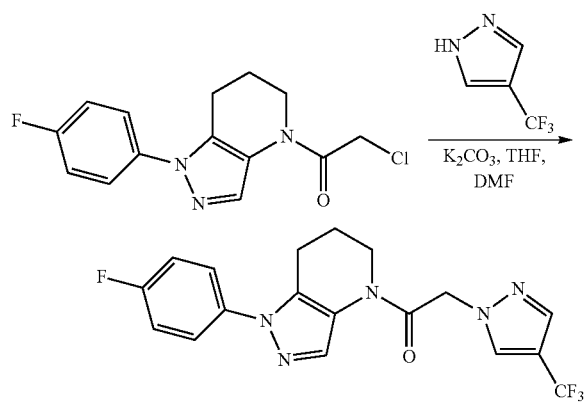

A mixture of 4-(trifluoromethyl)-1H-pyrazole (0.030 g, 0.22 mmol), 2-chloro-1-[1-(4-fluorophenyl)-6,7-dihydro-5H-pyrazolo[4,3-b]pyridine-4-yl]ethanone (0.025 g, 0.085 mmol) and K$_2$CO$_3$ (0.060 g, 0.43 mmol) in THF (0.8 mL) and DMF (0.4 mL) was heated at 65° C. for 1 hr. It was then cooled to rt. The mixture was partitioned between EtOAc (50 mL) and sat. NaHCO$_3$ (30 mL). The organic layer was separated, dried over Na$_2$SO$_4$, concentrated in vacuo and purified by reverse phase HPLC to afford the desired product (0.038 g, 100%). $^1$H NMR (400 MHz, CDCl$_3$) δ 8.40 (s, 1H), 7.89 (s, 1H), 7.77 (s, 1H), 7.44 (dd, J=8.8, 4.6 Hz, 2H), 7.16 (dd, J=8.8, 8.4 Hz, 2H), 5.20 (s, 2H), 3.83 (m, 2H), 2.85 (t, J=6.2 Hz, 2H), 2.10 (m, 2H); MS: (ES) m/z calculated for $C_{18}H_{15}F_4N_5O$ [M+H]$^+$ 394.1, found 394.1.

Example 49

Synthesis of 1-[1-(4-fluorophenyl)-6,7-dihydro-5H-pyrazolo[4,3-b]pyridin-4-yl]-2-[3-(trifluoromethyl)-6,7-dihydro-4H-pyrano[4,3-c]pyrazol-1-yl]ethanone

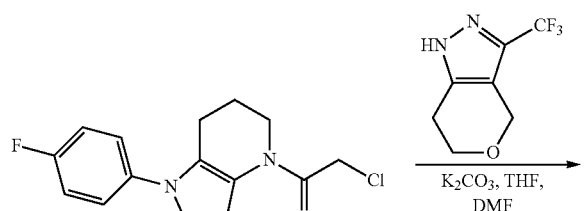

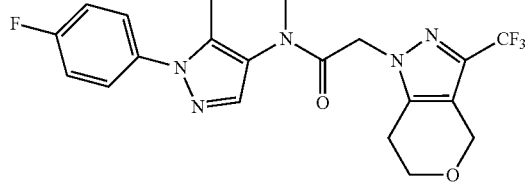

A mixture of 3-(trifluoromethyl)-1,4,6,7-tetrahydropyrano[4,3-c]pyrazole (0.050 g, 0.26 mmol), 2-chloro-1-[1-(4-fluorophenyl)-6,7-dihydro-5H-pyrazolo[4,3-b]pyridine-4-yl]ethanone (0.050 g, 0.17 mmol) and K$_2$CO$_3$ (0.130 g, 0.94 mmol) in THF (0.8 mL) and DMF (0.4 mL) was heated at 55° C. for 1 hr. It was then cooled to rt. The mixture was partitioned between EtOAc (50 mL) and sat. NaHCO$_3$ (30 mL). The organic layer was separated, dried over Na$_2$SO$_4$, concentrated in vacuo, and purified by reverse phase HPLC to afford the desired product (0.035 g, 55%). $^1$H NMR (400 MHz, CDCl$_3$) δ 8.38 (s, 1H), 7.44 (dd, J=8.8, 4.6 Hz, 2H), 7.17 (dd, J=8.8, 8.0 Hz, 2H), 5.13 (s, 2H), 4.75 (s, 2H), 3.98 (t, J=5.4 Hz, 2H), 3.87 (m, 2H), 2.85 (t, J=6.2 Hz, 2H), 2.79 (t, J=5.6 Hz, 2H), 2.10 (m, 2H); MS: (ES) m/z calculated for $C_{21}H_{19}F_4N_5O_2$ [M+H]$^+$ 450.1, found 450.1.

Example 50

Synthesis of 1-[1-(4-fluorophenyl)-6,7-dihydro-5H-pyrazolo[4,3-b]pyridin-4-yl]-2-[4-(1,2,4-oxadiazol-3-yl)pyrazol-1-yl]ethanone

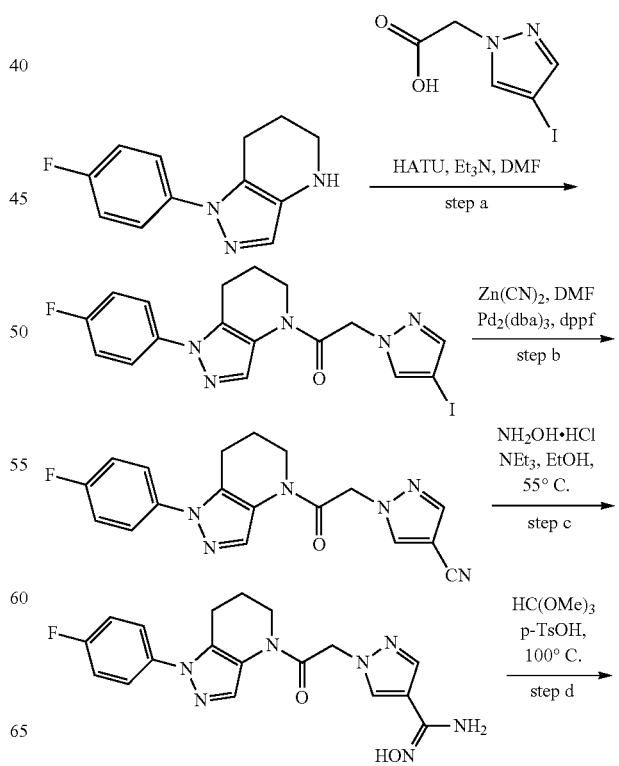

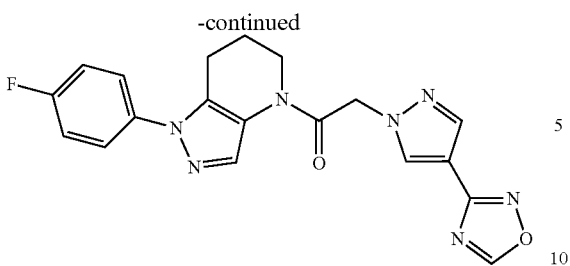

2H), 5.27 (m, 2H), 3.85 (m, 2H), 2.85 (m, 2H), 2.14 (m, 2H); MS: (ES) m/z calculated for $C_{19}H_{16}FN_7O_2$ [M+H]$^+$ 394.1, found 394.1.

Example 51

Synthesis of 1-[1-(4-fluorophenyl)-6,7-dihydro-5H-pyrazolo[4,3-b]pyridin-4-yl]-2-[3-(1H-imidazol-2-yl)pyrazolo[3,4-b]pyridin-1-yl]ethanone a) To a mixture of 1-(4-fluorophenyl)-4,5,6,7-tetrahydro-1H-pyrazolo[4,3-b]pyridine (0.400 g, 1.83 mmol), 2-(4-iodopyrazol-1-yl)acetic acid (0.554 g, 2.2 mmol) and NEt$_3$ (0.642 mL, 4.59 mmol) in DMF (5 mL) was added HATU (0.836 g, 2.2 mmol). The mixture was stirred at rt for 40 min. It was then quenched with water. The mixture was partitioned between EtOAc (100 mL) and sat. NaHCO$_3$ (50 mL). The organic layer was separated, dried over Na$_2$SO$_4$, concentrated in vacuo, and purified by flash chromatography (SiO$_2$, with a gradient elution of 0~30% EtOAc/CH$_2$Cl$_2$) to yield 1-[1-(4-fluorophenyl)-6,7-dihydro-5H-pyrazolo[4,3-b]pyridin-4-yl]-2-(4-iodopyrazol-1-yl)ethanone (0.82 g, 100%).

b) A mixture of 1-[1-(4-fluorophenyl)-6,7-dihydro-5H-pyrazolo[4,3-b]pyridin-4-yl]-2-(4-iodopyrazol-1-yl)ethanone (0.388 g, 0.86 mmol), Zn(CN)$_2$ (0.151 g, 1.29 mmol), Pd$_2$(dba)$_3$ (0.079 g, 0.086 mmol) and dppf (0.072 g, 0.13 mmol) in DMF (10 mL) was heated at 90° C. for 1 hr. It was then cooled to rt. The mixture was partitioned between EtOAc (10 mL) and sat. NaHCO$_3$ (50 mL). The organic layer was separated, dried over Na$_2$SO$_4$, concentrated in vacuo, and purified by flash chromatography with a gradient elution of 0-100% EtOAc/CH$_2$Cl$_2$ to afford 2-(4-cyanopyrazol-1-yl)-1-[1-(4-fluorophenyl)-6,7-dihydro-5H-pyrazolo[4,3-b]pyridin-4-yl]ethanone (0.205 g, 68%).

c) A mixture of 2-(4-cyanopyrazol-1-yl)-1-[1-(4-fluorophenyl)-6,7-dihydro-5H-pyrazolo[4,3-b]pyridin-4-yl]ethanone (0.175 g, 0.50 mmol), NH$_2$OH—HCl (0.500 g, 7.2 mmol) and NEt$_3$ (1.00 mL, 7.1 mmol) in EtOH (3 mL) was heated at 90° C. for 5 hrs. It was then cooled to rt. The mixture was partitioned between IPA/CHCl$_3$ (1:2, 50 mL) and sat. NaHCO$_3$ (30 mL). The organic layer was separated, dried over Na$_2$SO$_4$ and concentrated in vacuo to obtain 1-[2-[1-(4-fluorophenyl)-6,7-dihydro-5H-pyrazolo[4,3-b]pyridin-4-yl]-2-oxo-ethyl]-N'-hydroxy-pyrazole-4-carboxamidine (0.115 g, 60%).

d) A mixture of 1-[2-[1-(4-fluorophenyl)-6,7-dihydro-5H-pyrazolo[4,3-b]pyridin-4-yl]-2-oxo-ethyl]-N'-hydroxy-pyrazole-4-carboxamidine (0.115 g, 0.30 mmol) and p-TsOH.H$_2$O (0.030 g, 0.15 mmol) in HC(OMe)$_3$ (3 mL) was heated at 100° C. for 1.5 hrs. It was then cooled to rt. The mixture was partitioned between IPA/CHCl$_3$ (1:2, 50 mL) and sat. NaHCO$_3$ (30 mL). The organic layer was separated, dried over Na$_2$SO$_4$, concentrated in vacuo and purified by reverse phase HPLC to afford the desired product (0.055 g, 21%). $^1$H NMR (400 MHz, CDCl$_3$) δ 8.71 (s, 1H), 7.65-8.50 (m, 3H), 7.44 (dd, J=8.4, 4.6 Hz, 2H), 7.17 (dd, J=9.2, 7.6 Hz,

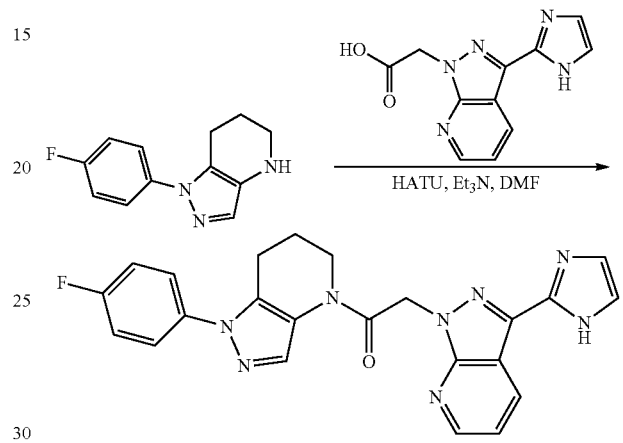

To a mixture of 1-(4-fluorophenyl)-4,5,6,7-tetrahydro-1H-pyrazolo[4,3-b]pyridine (0.050 g, 0.23 mmol), 2-[3-(1H-imidazol-2-yl)pyrazolo[3,4-b]pyridine-1-yl]acetic acid (0.050 g, 0.21 mmol) and Et$_3$N (0.15 mL, 1.07 mmol) in DMF (0.7 mL) was added HATU (0.130 g, 0.33 mmol). The mixture was stirred at rt for 30 min. It was then quenched with water. The mixture was partitioned between IPA/CHCl$_3$ (1:2, 100 mL) and sat. NaHCO$_3$ (40 ml). The organic layer was separated, dried over Na$_2$SO$_4$, concentrated in vacuo, and purified by reverse phase HPLC to afford the desired product (0.090 g, 96%). $^1$H NMR (TFA salt) (400 MHz, CD$_3$OD) δ 8.73 (dd, J=4.8, 1.6 Hz, 1H), 8.69 (dd, J=8.0, 1.6 Hz, 1H), 8.14 (s, 1H), 7.72 (s, 2H), 7.55 (m, 3H), 7.28 (dd, J=9.2, 8.4 Hz, 2H), 5.89 (s, 2H), 4.06 (m, 2H), 2.92 (t, J=6.2 Hz, 2H), 2.20 (m, 2H); MS: (ES) m/z calculated for $C_{23}H_{19}FN_8O$ [M+H]$^+$ 443.1, found 443.1.

Example 52

Synthesis of 1-[1-(4-fluorophenyl)-6,7-dihydro-5H-pyrazolo[4,3-b]pyridin-4-yl]-2-[3-(trifluoromethyl)-4,5,6,7-tetrahydroindazol-1-yl]ethanone

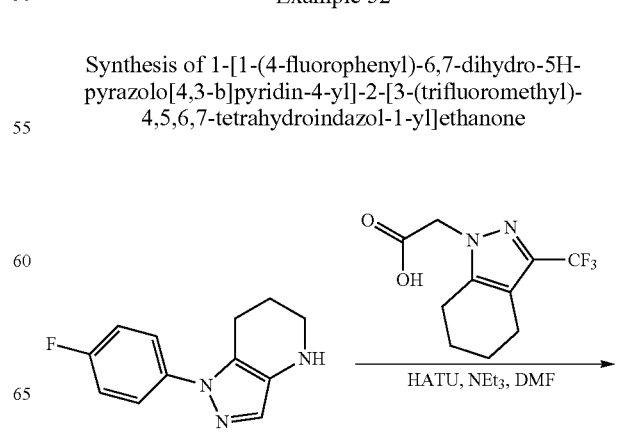

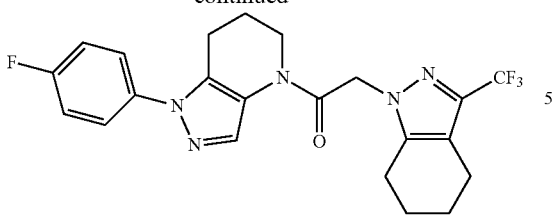

To a mixture of 1-(4-fluorophenyl)-4,5,6,7-tetrahydro-1H-pyrazolo[4,3-b]pyridine (0.023 g, 0.11 mmol), 2-[3-(trifluoromethyl)-4,5,6,7-tetrahydroindazol-1-yl]acetic acid (0.027 g, 0.11 mmol) and NEt$_3$ (0.050 mL, 0.36 mmol) in DMF (0.6 mL) was added HATU (0.050 g, 0.13 mmol). The mixture was stirred at rt for 30 min. It was then quenched with water. The mixture was partitioned between IPA/CHCl$_3$ (1:2, 50 mL) and sat. NaHCO$_3$ (30 mL). The organic layer was separated, dried over Na$_2$SO$_4$, concentrated in vacuo, and purified by reverse phase HPLC to afford the desired product (0.027 g, 55%). $^1$H NMR (400 MHz, CDCl$_3$) δ 8.43 (s, 1H), 7.42 (dd, J=8.8, 4.4 Hz, 2H), 7.17 (dd, J=9.2, 8.0 Hz, 2H), 5.15 (s, 2H), 3.87 (m, 2H), 2.82 (t, J=6.2 Hz, 2H), 2.61 (m, 4H), 2.11 (m, 2H), 1.87 (m, 2H), 1.79 (m, 2H); MS: (ES) m/z calculated for C$_{22}$H$_{21}$F$_4$N$_5$O [M+H]$^+$ 448.1, found 448.1.

Example 53

Synthesis of 2-(1,3-benzoxazol-2-yl)-1-[1-(4-fluorophenyl)-6,7-dihydro-5H-pyrazolo[4,3-b]pyridin-4-yl]ethanone

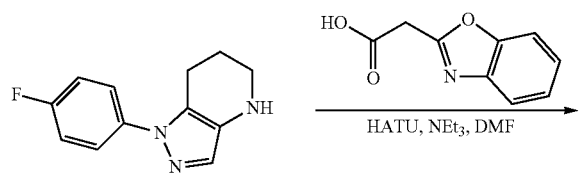

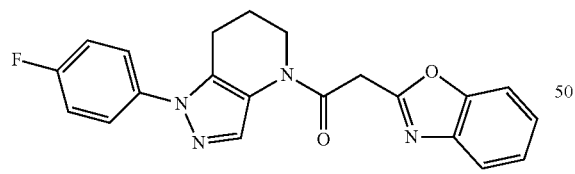

To a mixture of 1-(4-fluorophenyl)-4,5,6,7-tetrahydro-1H-pyrazolo[4,3-b]pyridine (0.023 g, 0.11 mmol), benzooxazol-2-yl-acetic acid (0.023 g, 0.13 mmol) and NEt$_3$ (0.060 mL, 0.43 mmol) in DMF (0.6 mL) was added HATU (0.050 g, 0.13 mmol). The mixture was stirred at rt for 30 min. It was then quenched with water. The mixture was partitioned between IPA/CHCl$_3$ (1:2, 50 mL) and sat. NaHCO$_3$ (30 mL). The organic layer was separated, dried over Na$_2$SO$_4$, concentrated in vacuo, and purified by reverse phase HPLC to afford the desired product (0.022 g, 53%). $^1$H NMR (400 MHz, CDCl$_3$) δ 8.46 (s, 1H), 7.71 (m, 1H), 7.53 (m, 1H), 7.45 (dd, J=8.8, 4.8 Hz, 2H), 7.34 (m, 2H), 7.15 (dd, J=8.8, 8.4 Hz, 2H), 4.25 (s, 2H), 3.88 (m, 2H), 2.83 (t, J=6.4 Hz, 2H), 2.08 (m, 2H); MS: (ES) m/z calculated for C$_{21}$H$_{17}$FN$_4$O$_2$ [M+H]$^+$ 377.1, found 377.1.

Example 54

Synthesis of 2-[4-chloro-5-methyl-3-(trifluoromethyl)pyrazol-1-yl]-1-[1-(4-fluorophenyl)-6,7-dihydro-5H-pyrazolo[4,3-b]pyridin-4-yl]-3-methoxypropan-1-one

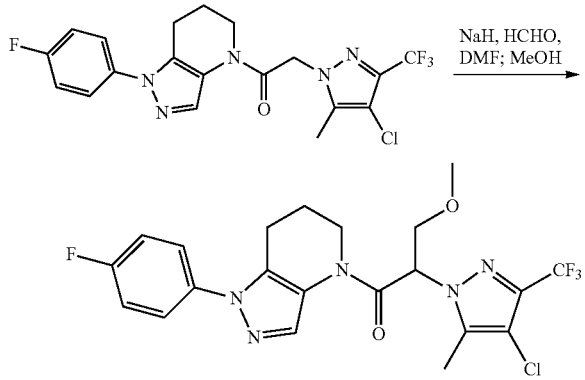

To a mixture of 2-[4-chloro-5-methyl-3-(trifluoromethyl)pyrazol-1-yl]-1-[1-(4-fluorophenyl)-6,7-dihydro-5H-pyrazolo[4,3-b]pyridin-4-yl]ethanone (0.045 g, 0.10 mmol) and NaH (0.030 g, 0.75 mmol, 60% in mineral oil) in DMF (0.8 mL) was added dry paraformaldehyde (0.015 g, 0.50 mmol). The mixture was stirred at rt for 30 min. It was then quenched with water. The mixture was partitioned between EtOAc (50 mL) and brine (30 mL). The organic layer was separated, dried over Na$_2$SO$_4$, concentrated in vacuo, and purified by reverse phase HPLC to afford the desired product (0.006 g, 12%). $^1$H NMR (400 MHz, CDCl$_3$) δ 8.44 (s, 1H), 7.44 (dd, J=8.8, 4.6 Hz, 2H), 7.16 (dd, J=8.4, 8.4 Hz, 2H), 5.51 (dd, J=8.0, 7.2 Hz, 1H), 4.18 (m, 1H), 4.08 (m, 1H), 3.75 (m, 1H), 3.37 (s, 3H), 3.35 (m, 1H), 2.78 (m, 2H), 2.33 (s, 3H), 2.09 (m, 2H); MS: (ES) m/z calculated for C$_{21}$H$_{20}$ClF$_4$N$_5$O$_2$ [M+H]$^+$ 486.1, found 486.1.

Example 55

Synthesis of 2-[4-chloro-5-methyl-3-(trifluoromethyl)pyrazol-1-yl]-1-[1-(4-fluorophenyl)-6,7-dihydro-5H-pyrazolo[4,3-b]pyridin-4-yl]-3-hydroxypropan-1-one

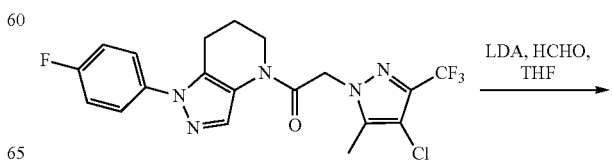

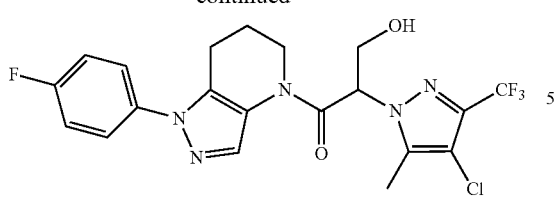

To a mixture of 2-[4-chloro-5-methyl-3-(trifluoromethyl)pyrazol-1-yl]-1-[1-(4-fluorophenyl)-6,7-dihydro-5H-pyrazolo[4,3-b]pyridin-4-yl]ethanone (0.100 g, 0.23 mmol) in THF (3 ml) at −78° C. was added LDA (0.15 mL, 0.3 mmol, 2 M in THF). After stirred for 10 min at −78° C., dry paraformaldehyde (0.020 g, 0.66 mmol, suspended in THF) was added. The mixture was then warmed to rt for 8 min, quenched with sat. NH$_4$Cl. The mixture was partitioned between EtOAc (50 mL) and brine (30 mL). The organic layer was separated, dried over Na$_2$SO$_4$, concentrated in vacuo, and purified by reverse phase HPLC to yield the desired product (0.060 g, 56%). $^1$H NMR (400 MHz, CDCl$_3$) δ 8.45 (s, 1H), 7.43 (dd, J=8.4, 4.6 Hz, 2H), 7.17 (dd, J=8.8, 8.4 Hz, 2H), 5.40 (t, J=5.4 Hz, 1H), 4.90 (s, 1H), 4.30 (m, 1H), 4.20 (m, 1H), 3.71 (m, 1H), 3.29 (m, 1H), 2.79 (m, 2H), 2.28 (s, 3H), 1.95 (m, 2H); MS: (ES) m/z calculated for C$_{20}$H$_{18}$ClF$_4$N$_5$O$_2$ [M+H]$^+$ 472.1, found 472.1.

Example 56

Synthesis of 1-[1-(4-fluorophenyl)-6,7-dihydro-5H-pyrazolo[4,3-b]pyridin-4-yl]-3-hydroxy-2-[5-methyl-3-(trifluoromethyl)pyrazol-1-yl]propan-1-one

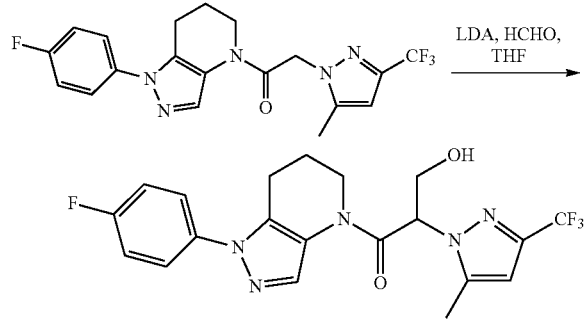

To a mixture of 1-[1-(4-fluorophenyl)-6,7-dihydro-5H-pyrazolo[4,3-b]pyridin-4-yl]-2-[5-methyl-3-(trifluoromethyl)pyrazol-1-yl]ethanone (0.100 g, 0.25 mmol) in THF (3 mL) at −78° C. was added LDA (0.15 mL, 0.3 mmol, 2 M in THF). After stirring for 10 min at −78° C., dry paraformaldehyde (0.025 g, 0.82 mmol, suspended in THF) was added. The mixture was then warmed to rt for 8 min, followed by the addition of sat. NH$_4$Cl. The mixture was partitioned between EtOAc (50 mL) and brine (30 mL). The organic layer was separated, dried over Na$_2$SO$_4$, concentrated in vacuo, and purified by reverse phase HPLC to yield the desired product (0.056 g, 55%). $^1$H NMR (400 MHz, CDCl$_3$) δ 8.50 (s, 1H), 7.42 (m, 2H), 7.18 (dd, J=8.4, 8.4 Hz, 2H), 6.36 (s, 1H), 5.41 (t, J=5.6 Hz, 1H), 4.36 (m, 1H), 4.20 (m, 1H), 3.69 (m, 1H), 3.26 (m, 1H), 2.76 (m, 2H), 2.31 (s, 3H), 1.92 (m, 2H); MS: (ES) m/z calculated for C$_{20}$H$_{19}$F$_4$N$_5$O$_2$ [M+H]$^+$ 438.1, found 438.1.

Example 57

Synthesis of 1-[1-(4-fluorophenyl)-6,7-dihydro-5H-pyrazolo[4,3-b]pyridin-4-yl]-4-hydroxy-4-methyl-2-[5-methyl-3-(trifluoromethyl)pyrazol-1-yl]pentan-1-one

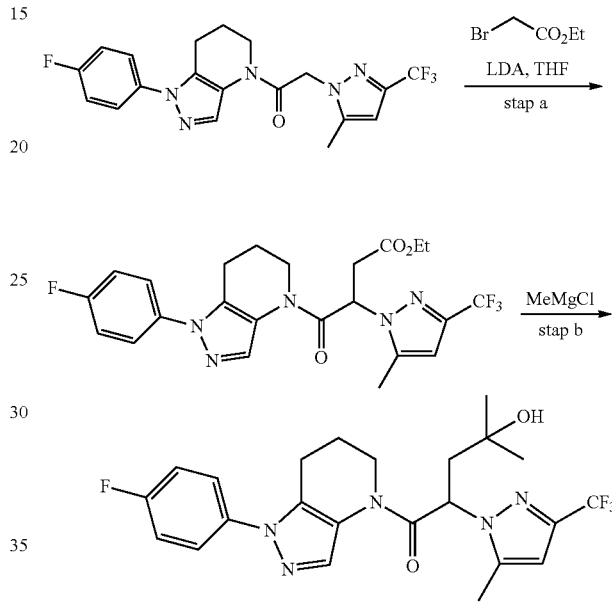

a) To a mixture of 1-[1-(4-fluorophenyl)-6,7-dihydro-5H-pyrazolo[4,3-b]pyridin-4-yl]-2-[5-methyl-3-(trifluoromethyl)pyrazol-1-yl]ethanone (0.150 g, 0.37 mmol) in THF (4 ml) at −78° C. was added LDA (0.247 mL, 0.50 mmol, 2 M in THF). After stirring for 10 min at −78° C., ethyl bromoacetate (0.061 mL, 0.55 mmol) was added. The mixture was then warmed to rt for 10 min and quenched with sat. NH$_4$Cl. The mixture was partitioned between EtOAc (50 mL) and brine (30 mL). The organic layer was separated, dried over Na$_2$SO$_4$, concentrated in vacuo and purified by flash chromatography (SiO$_2$ with a gradient elution of 0-60% EtOAc/hexanes) to afford ethyl 4-[1-(4-fluorophenyl)-6,7-dihydro-5H-pyrazolo[4,3-b]pyridin-4-yl]-3-[5-methyl-3-(trifluoromethyl)pyrazol-1-yl]-4-oxo-butanoate (0.120 g, 83%).

b) A mixture of ethyl 4-[1-(4-fluorophenyl)-6,7-dihydro-5H-pyrazolo[4,3-b]pyridin-4-yl]-3-[5-methyl-3-(trifluoromethyl)pyrazol-1-yl]-4-oxo-butanoate (0.028 g, 0.10 mmol) and MeMgCl (0.100 mL, 0.30 mmol, 3 M in THF) in THF (1 mL) was stirred at rt for 10 min. It was then quenched with sat. NH$_4$Cl and partitioned between EtOAc (50 mL) and brine (30 mL). The organic layer was separated, dried over Na$_2$SO$_4$, concentrated in vacuo and purified by reverse phase HPLC to yield the desired product (0.005 g, 17%). $^1$H NMR (400 MHz, CDCl$_3$) δ 8.45 (s, 1H), 7.43 (m, 2H), 7.16 (dd, J=8.8, 8.4 Hz, 2H), 6.31 (s, 1H), 5.72 (t, J=6.4 Hz, 1H), 3.88 (m, 1H), 3.52 (m, 1H), 2.75 (m, 3H), 2.32 (s, 3H), 2.25 (m, 2H), 1.96 (m, 1H), 1.85 (m, 1H), 1.34 (s, 3H), 1.18 (s, 3H); MS: (ES) m/z calculated for $C_{23}H_{25}F_4N_5O_2$ [M+H]$^+$ 480.1, found 480.1.

Example 58

Synthesis of 1-[1-(4-fluorophenyl)-6,7-dihydro-5H-pyrazolo[4,3-b]pyridin-4-yl]-2-[5-methyl-3-(trifluoromethyl)pyrazol-1-yl]-3-tetrahydropyran-4-yl-propan-1-one

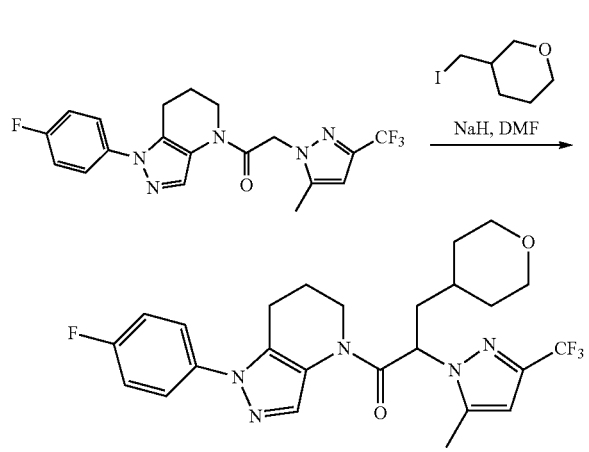

A mixture of 1-[1-(4-fluorophenyl)-6,7-dihydro-5H-pyrazolo[4,3-b]pyridin-4-yl]-2-[5-methyl-3-(trifluoromethyl)pyrazol-1-yl]ethanone (0.100 g, 0.25 mmol), 4-(iodomethyl)tetrahydro-2H-pyran (0.165 g, 0.75 mmol) and NaH (0.030 g, 0.75 mmol, 60% in mineral oil) in DMF (0.8 mL) was stirred at rt for 1.5 hrs. It was then quenched with sat. NH$_4$Cl. The mixture was partitioned between EtOAc (50 mL) and brine (30 mL). The organic layer was separated, dried over Na$_2$SO$_4$, concentrated in vacuo, and purified by reverse phase HPLC to afford the desired product (0.007 g, 6%). $^1$H NMR (400 MHz, CDCl$_3$) δ 8.44 (s, 1H), 7.43 (dd, J=8.8, 4.8 Hz, 2H), 7.16 (dd, J=8.8, 8.4 Hz, 2H), 6.31 (s, 1H), 5.54 (m, 1H), 3.95 (m, 2H), 3.78 (m, 1H), 3.47 (m, 1H), 3.34 (m, 2H), 2.75 (m, 2H), 2.30 (s, 3H), 2.20 (m, 3H), 1.88 (m, 3H), 1.40 (m, 3H); MS: (ES) m/z calculated for $C_{25}H_{27}F_4N_5O_2$ [M+H]$^+$ 506.2, found 506.2.

Example 59

Synthesis of 4-[1-(4-fluorophenyl)-6,7-dihydro-5H-pyrazolo[4,3-b]pyridin-4-yl]-3-[5-methyl-3-(trifluoromethyl)pyrazol-1-yl]-4-oxo-butanamide

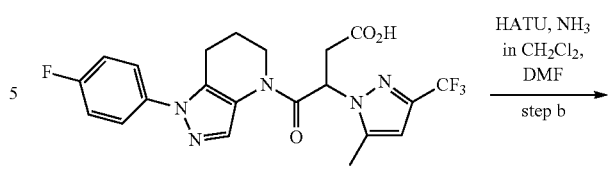

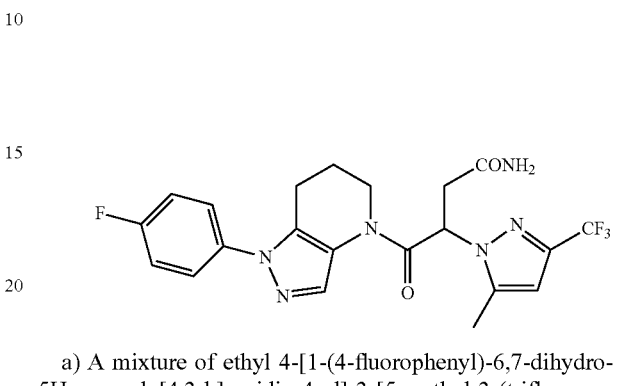

a) A mixture of ethyl 4-[1-(4-fluorophenyl)-6,7-dihydro-5H-pyrazolo[4,3-b]pyridin-4-yl]-3-[5-methyl-3-(trifluoromethyl)pyrazol-1-yl]-4-oxo-butanoate (0.030 g, 0.060 mmol), LiOH.H$_2$O (0.020 g, 0.47 mmol), THF (0.4 mL), MeOH (0.4 mL) and H$_2$O (0.2 mL) was stirred for 30 min at rt. It was then acidified with 1 M aq. HCl (2 mL) and extracted with IPA/CHCl$_3$ (1:2, 50 mL). The organic layer was separated, dried over Na$_2$SO$_4$, and concentrated in vacuo to yield 4-[1-(4-fluorophenyl)-6,7-dihydro-5H-pyrazolo[4,3-b]pyridin-4-yl]-3-[5-methyl-3-(trifluoromethyl)pyrazol-1-yl]-4-oxo-butanoic acid (0.029 g, 100%).

b) To a mixture of 4-[1-(4-fluorophenyl)-6,7-dihydro-5H-pyrazolo[4,3-b]pyridin-4-yl]-3-[5-methyl-3-(trifluoromethyl)pyrazol-1-yl]-4-oxo-butanoic acid (0.029 g, 0.08 mmol) and NH$_3$ (0.3 mL, sat. in CH$_2$Cl$_2$) in DMF (0.6 mL) was added HATU (0.040 g, 0.10 mmol). The mixture was stirred at rt for 30 min. It was then quenched with water. The mixture was partitioned between IPA/CHCl$_3$ (1:2, 50 mL) and sat. NaHCO$_3$ (30 mL). The organic layer was separated, dried over Na$_2$SO$_4$, concentrated in vacuo, and purified by reverse phase HPLC to afford the desired product (0.014 g, 37%). $^1$H NMR (400 MHz, CDCl$_3$) δ 8.44 (s, 1H), 7.42 (dd, J=9.2, 4.6 Hz, 2H), 7.16 (dd, J=8.4, 8.0 Hz, 2H), 6.53 (s, 1H), 6.34 (s, 1H), 6.32 (s, 1H), 5.92 (m, 1H), 3.80 (m, 1H), 3.41 (m, 1H), 3.33 (m, 1H), 3.00 (m, 1H), 2.76 (m, 2H), 2.37 (s, 3H), 1.98 (m, 1H), 1.88 (m, 1H); MS: (ES) m/z calculated for $C_{21}H_{20}F_4N_6O_2$ [M+H]$^+$ 465.1, found 465.1.

Example 60

Synthesis of methyl 4-[2-[4-chloro-5-methyl-3-(trifluoromethyl)pyrazol-1-yl]acetyl]-1-(4-fluorophenyl)-6,7-dihydro-5H-pyrazolo[4,3-b]pyridine-5-carboxylate

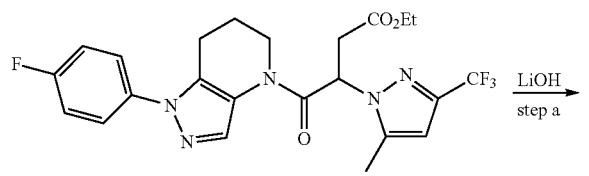

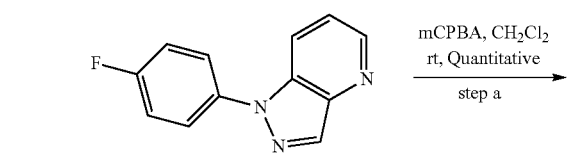

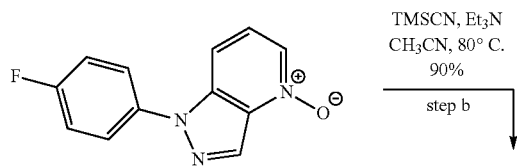

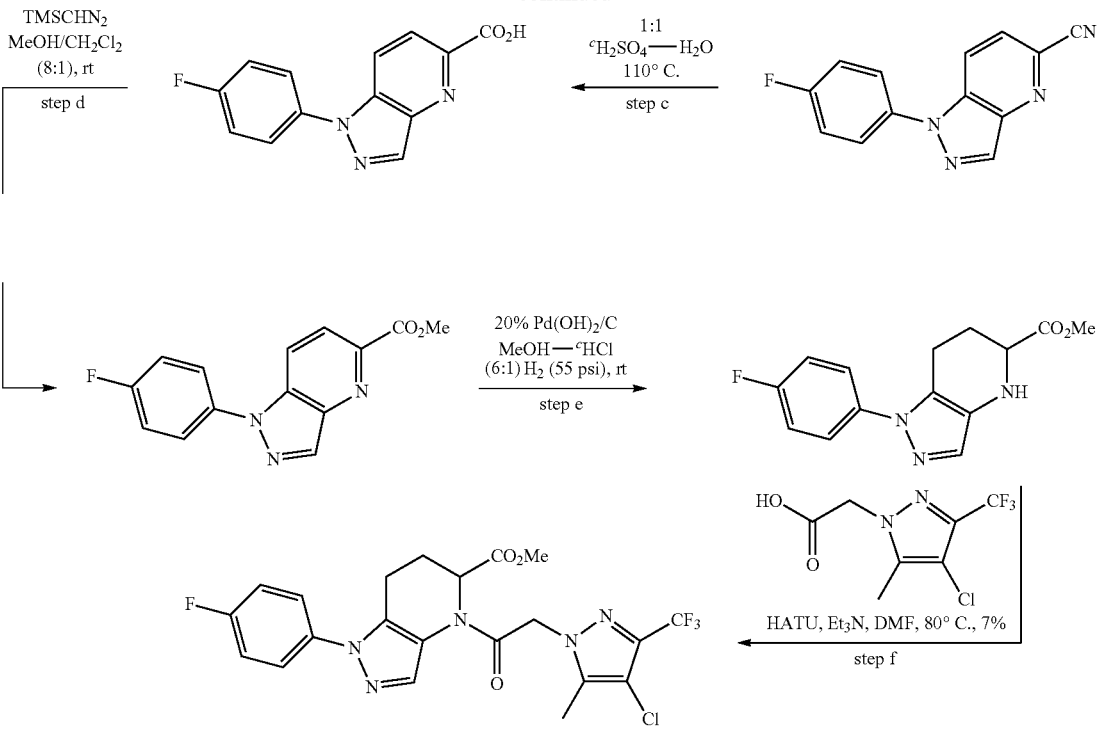

a) To a cooled solution of 1-(4-fluorophenyl)pyrazolo[4,3-b]pyridine (1 g, 4.67 mmol) in CH$_2$Cl$_2$ (50 mL) under nitrogen atmosphere was added mCPBA (75%, 1.2 g, 5.14 mmol) in one portion. The resulting solution was allowed to warm to room temperature and stirred for 12 h. The reaction mixture was then diluted with CH$_2$Cl$_2$ (100 mL) and washed with saturated NaHCO$_3$ solution (100 mL). The aqueous layer was extracted with CH$_2$Cl$_2$ (50 mL). The combined organic layers were dried (MgSO$_4$), filtered and concentrated in vacuo. The crude residue was purified by flash chromatography (SiO$_2$, 20% MeOH in CH$_2$Cl$_2$) to afford the desired product (1.1 g, 4.7 mmol, quantitative yield).

b) To a solution of 1-(4-fluorophenyl)-4-oxido-pyrazolo[4,3-b]pyridin-4-ium (916 mg, 4 mmol) in CH$_3$CN (10 mL) was added TMSCN (800 µL, 6 mmol) and Et$_3$N (556 µL, 4 mmol) and stirred at 80° C. overnight. The reaction mixture was then cooled to room temperature and concentrated in vacuo. The crude residue was purified by flash chromatography (SiO$_2$, 80% EtOAc in hexanes) to give the desired product (857 mg, 3.6 mmol, 90%).

c) Water (10 mL) was added to 1-(4-fluorophenyl)pyrazolo[4,3-b]pyridine-5-carbonitrile (600 mg, 2.52 mmol) and the mixture was cooled to 0° C. followed by the addition of concentrated H$_2$SO$_4$ (10 mL) slowly drop wise. The obtained yellowish clear solution was then stirred at 110° C. for 12 h. The reaction mixture was cooled to 0° C. followed by the slow addition of 10 N NaOH drop wise with stirring until reached pH 5-6. The resulting white solid was filtered and washed with water (30 mL) and heptanes (50 mL), and was then dried under high vacuum to obtain the desired crude product (700 mg) which was used in the next step without further purification.

d) To 1-(4-fluorophenyl)pyrazolo[4,3-b]pyridine-5-carboxylic acid (650 mg, 2.5 mmol) was added CH$_2$Cl$_2$ (40 mL) and MeOH (5 mL) followed by TMSCHN$_2$ (2 M in Et$_2$O, 10 mL, excess) drop wise. The resulting yellow suspension was stirred at room temperature for an hour. The reaction mixture was then diluted with CH$_2$Cl$_2$ (40 mL), washed with saturated NaHCO$_3$ solution (50 mL), dried (MgSO$_4$) and concentrated in vacuo to obtain the desired crude product (750 mg) which was used directly in the next step without further purification.

e) MeOH (6 mL) and 12 N HCl (1 mL) were added to methyl 1-(4-fluorophenyl)pyrazolo[4,3-b]pyridine-5-carboxylate (100 mg, 0.37 mmol) followed by 20% Pd(OH)$_2$ on carbon (100 mg, excess) and the resulting mixture was stirred under H$_2$ gas (55 psi) on a Parr shaker at room temperature for 36 h. The reaction mixture was then filtered through a small pad of celite, washed with MeOH (20 mL) and concentrated in vacuo. The obtained residue was dissolved in EtOAc (50 mL) and washed with saturated NaHCO$_3$ solution (20 mL), dried (MgSO$_4$) and concentrated in vacuo to obtain the desired crude product (30 mg) which was used as such in next step without further purification.

f) To a solution of 2-[4-chloro-5-methyl-3-(trifluoromethyl)pyrazol-1-yl]acetic acid (20 mg, 0.073 mmol) in DMF (2 mL) was added Et$_3$N (50 µL, 0.219 mmol), HATU (55 mg, 0.145 mmol) followed by methyl 1-(4-fluorophenyl)-4,5,6,7-tetrahydropyrazolo[4,3-b]pyridine-5-carboxylate (20 mg, 0.073 mmol) at room temperature. The resulting solution was then stirred at 80° C. for 5 h. The reaction mixture was then cooled to room temperature, H$_2$O (10 mL) was added and the mixture was extracted with EtOAc (2×15 mL). The combined EtOAc layers were dried (MgSO$_4$), filtered, concentrated in vacuo and the resulting crude product was purified by reverse phase HPLC (C18 column, acetonitrile-H$_2$O with 0.1% TFA as eluent) to give the desired product as white powder (0.004 g, 0.008 mmol, 7%). $^1$H NMR (400 MHz, CD$_3$OD) δ 8.28 (s, 1H), 7.52 (2H, dd, J=5, 9 Hz), 7.26 (2H, t, 8.6, J=17.2 Hz), 5.3 (2H, dd, J=17.2, 69.2 Hz), 3.83 (s, 3H), 2.80-2.82 (m, 2H), 2.29 (s, 3H), 2.15-2.17 (m, 2H); MS: (ES) m/z calculated for $C_{21}H_{18}ClF_4N_5O_3$ [M+H]$^+$ 500.1, found 500.1.

Example 61

Synthesis of 1-[1-(4-fluorophenyl)-6,7-dihydro-5H-pyrazolo[4,3-b]pyridin-4-yl]-2-[3-(trifluoromethyl)-5,6-dihydro-4H-cyclopenta[c]pyrazol-1-yl]ethanone

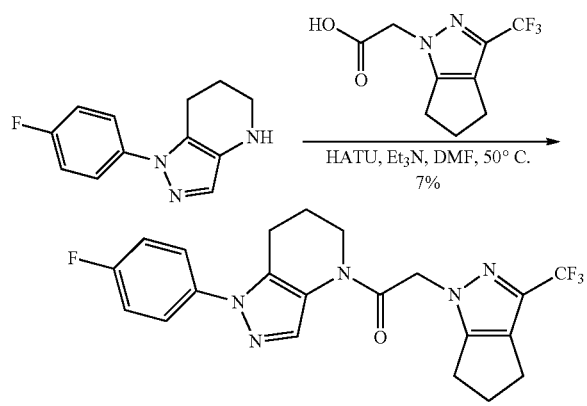

To a solution 2-[3-(trifluoromethyl)-5,6-dihydro-4H-cyclopenta[c]pyrazol-1-yl]acetic acid (83 mg, 0.35 mmol) in DMF (2 mL) was added Et$_3$N (75 µL, 0.525 mmol), HATU (160 mg, 0.42 mmol), followed by 1-(4-fluorophenyl)-4,5,6,7-tetrahydropyrazolo[4,3-b]pyridine (77 mg, 0.35 mmol) at room temperature. The resulting solution was then stirred at 50° C. for 30 min. The reaction mixture was then cooled to room temperature, H$_2$O (10 mL) was added and the mixture was extracted with EtOAc (2×20 mL). The combined EtOAc layers were dried (MgSO$_4$), filtered, and concentrated in vacuo. Purification by reverse phase HPLC (C18 column, acetonitrile-H$_2$O with 0.1% TFA as eluent) to give the desired product as a white powder (0.011 g, 0.025 mmol, 7%). $^1$H NMR (400 MHz, DMSO-d$_6$) δ 8.15 (s, 1H), 7.6 (m, 2H), 7.35 (t, 2H, J=8.6, 17.6 Hz), 5.38 (s, 2H), 3.77 (m, 2H), 2.85 (t, 2H, J=6.3, 12.5 Hz), 2.66 (m, 4H), 2.53 (m, 2H), 1.97 (m, 2H); MS: (ES) m/z calculated for $C_{21}H_{19}F_4N_5O$ [M+H]$^+$ 434.2, found 434.1.

Example 62

Synthesis of 2-[4-chloro-3-(trifluoromethyl)phenyl]-1-[1-(4-fluorophenyl)-6,7-dihydro-5H-pyrazolo[4,3-b]pyridin-4-yl]propan-1-one

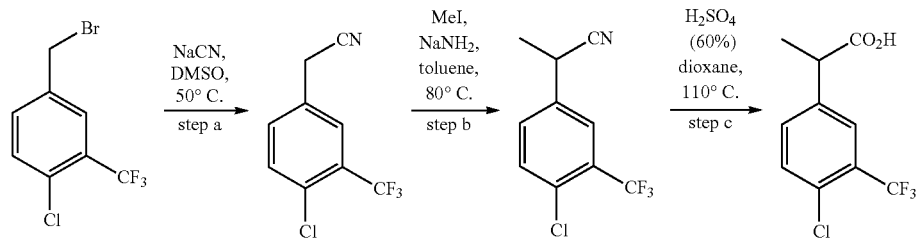

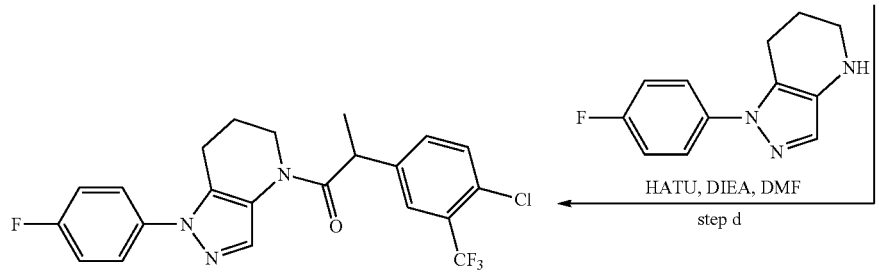

a) To a solution of 4-(bromomethyl)-1-chloro-2-(trifluoromethyl)benzene (3.94 g, 14.4 mmol) in DMSO (29 mL) was added NaCN (1.06 g, 21.6 mmol). The mixture was heated at 50° C. for 1 h with stirring. After cooling to room temperature, the reaction mixture was poured into a 100 mL beaker containing ice water (25 mL). The aqueous layer was extracted with dichloromethane (4×10 mL), and the combined organic layers were washed with brine and dried (Na$_2$SO$_4$), filtered, and concentrated in vacuo to give the desired product (2.5 g, 79%).

b) To a mixture of 2-[4-chloro-3-(trifluoromethyl)phenyl]acetonitrile (2.0 g, 9.1 mmol) and methyl iodide (1.29 g, 9.1 mmol) in toluene (20 mL) at 80° C. was slowly added NaNH$_2$ (428 mg, 11 mmol). The mixture was stirred at 80° C. for 1 hour. After cooling to room temperature, water (10 mL) was added. The mixture was extracted with ethyl acetate (2×15 mL). The combined organic layers were washed with brine and dried (Na$_2$SO$_4$), filtered, and concentrated in vacuo. The crude residue was purified by flash chromatography (SiO$_2$, 0-15% ethyl acetate in hexanes) to afford the desired product (500 mg, 24%).

c) To a solution of 2-[4-chloro-3-(trifluoromethyl)phenyl]propanenitrile (450 mg, 1.93 mmol) in dioxane (6 mL) was added sulfuric acid (60%, 6 mL). The mixture was heated at 110° C. for 14 hours. After cooling to room temperature, the reaction mixture was partitioned between water and dichloromethane. The aqueous layer was extracted with dichloromethane (2×10 mL), and the combined organic layers were washed with brine and dried (Na$_2$SO$_4$), filtered, and concentrated in vacuo to give the desired product (350 mg, 72%).

d) To a mixture of 2-[4-chloro-3-(trifluoromethyl)phenyl]propanoic acid (47 mg, 0.184 mmol) and 1-(4-fluorophenyl)-4,5,6,7-tetrahydro-1H-pyrazolo[4,3-b]pyridine (40 mg, 0.184 mmol) in DMF (1 mL) was added Hunig's base (59 mg, 0.46 mmol) and 2-(1H-7-azabenzotriazol-1-yl)-1,1,3,3-tetramethyl uranium hexafluorophosphate methanaminium (HATU) (77 mg, 0.2 mmol). The mixture was stirred at room temperature for 1 hour, and then was partitioned between water (4 mL) and ethyl acetate (6 mL). The organic layer was washed with brine and dried (Na$_2$SO$_4$), filtered, concentrated in vacuo, and purified by reverse phase HPLC (C18 column, acetonitrile-H$_2$O with 0.1% TFA as eluent) to give the desired product as a white solid (24 mg, 29%). $^1$H NMR (400 MHz, CDCl$_3$) δ 8.51 (s, 1H), 7.62 (d, J=2.0 Hz, 1H), 7.48-7.42 (m, 4H), 7.16-7.11 (m, 2H), 4.11 (m, 1H), 3.76 (m, 1H), 3.52 (m, 1H), 2.77 (m, 2H), 1.96 (m, 1H), 1.80 (m, 1H), 1.55 (d, J=7.2 Hz, 3H); MS: (ES) m/z calculated for C$_{22}$H$_{18}$ClF$_4$N$_3$O [M+H]$^+$ 452.1, found 452.1.

Example 63

Synthesis of 2-[2-chloro-4-(trifluoromethyl)phenyl]-1-[1-(4-fluorophenyl)-6,7-dihydro-5H-pyrazolo[4,3-b]pyridin-4-yl]ethanone

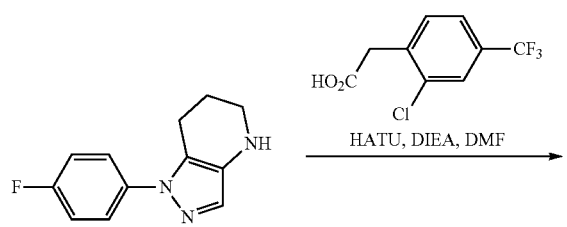

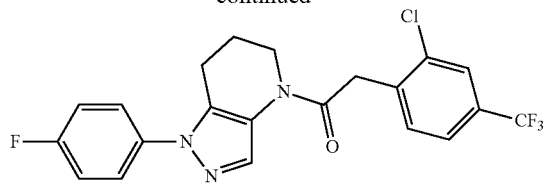

To a mixture of 2-[2-chloro-4-(trifluoromethyl)phenyl]acetic acid (59 mg, 0.23 mmol) and 1-(4-fluorophenyl)-4,5,6,7-tetrahydro-1H-pyrazolo[4,3-b]pyridine (50 mg, 0.23 mmol) in DMF (1 mL) was added Hunig's base (59 mg, 0.46 mmol) and 2-(1H-7-azabenzotriazol-1-yl)-1,1,3,3-tetramethyl uranium hexafluorophosphate methanaminium (HATU) (96 mg, 0.2 mmol). The mixture was stirred at room temperature for 1 hour, and then was partitioned between water (4 mL) and ethyl acetate (6 mL). The organic layer was washed with brine and dried (Na$_2$SO$_4$), filtered, concentrated in vacuo, and purified by reverse phase HPLC (C18 column, acetonitrile-H$_2$O with 0.1% TFA as eluent) to give the desired product as a white solid (25 mg, 25%). $^1$H NMR (400 MHz, CDCl$_3$) δ 8.44 (s, 0.8H), 7.70 (s, 1H), 7.56-7.44 (m, 4H), 7.38 (s, 0.2H), 7.18-7.14 (m, 2H), 4.14 (s, 2H), 3.82 (m, 2H), 2.85 (m, 2H), 2.08 (m, 2H); MS: (ES) m/z calculated for C$_{21}$H$_{16}$ClF$_4$N$_3$O [M+H]$^+$ 438.1, found 438.1.

Example 64

Synthesis of 2-[1H-benzimidazo-2-yl)-1-[1-(4-fluorophenyl)-6,7-dihydro-5H-pyrazolo[4,3-b]pyridin-4-yl]ethanone

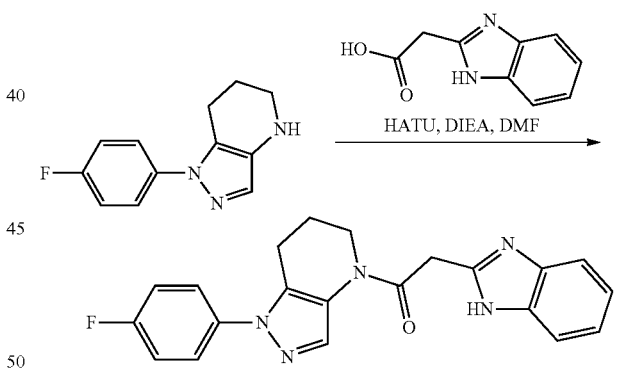

To a mixture of (1H-benzoimidazol-2yl)acetic acid (41 mg, 0.23 mmol) and 1-(4-fluorophenyl)-4,5,6,7-tetrahydro-1H-pyrazolo[4,3-b]pyridine (50 mg, 0.23 mmol) in DMF (1 mL) was added Hunig's base (59 mg, 0.46 mmol) and 2-(1H-7-azabenzotriazol-1-yl)-1,1,3,3-tetramethyl uranium hexafluorophosphate methanaminium (HATU, 96 mg, 0.2 mmol). The mixture was stirred at room temperature for 1 hour and then was partitioned between water (4 mL) and ethyl acetate (6 mL). The organic layer was washed with brine and dried (Na$_2$SO$_4$), filtered, concentrated in vacuo, and purified by reverse phase HPLC (C18 column, acetonitrile-H$_2$O with 0.1% TFA as eluent) to give the desired product as a white solid (0.020 g, 23%). $^1$H NMR (400 MHz, CDCl$_3$) δ 8.38 (s, 0.8H), 8.00 (s, 1H), 7.85 (m, 1H), 7.61 (s, 0.2H), 7.52-7.43 (m, 2H), 7.36-7.29 (m, 3H), 7.23-7.14 (m, 2H), 5.18 (s, 2H), 3.84 (m, 2H), 2.88 (m, 2H), 2.13 (m, 2H); MS: (ES) m/z calculated for $C_{21}H_{16}ClF_4N_3O$ [M+H]$^+$ 376.1, found 376.1.

Example 65

Synthesis of 1-[1-(4-fluorophenyl)-6,7-dihydro-5H-pyrazolo[4,3-b]pyridin-4-yl]-2-pyrrolo[2,3-b]pyridin-1-yl-ethanone

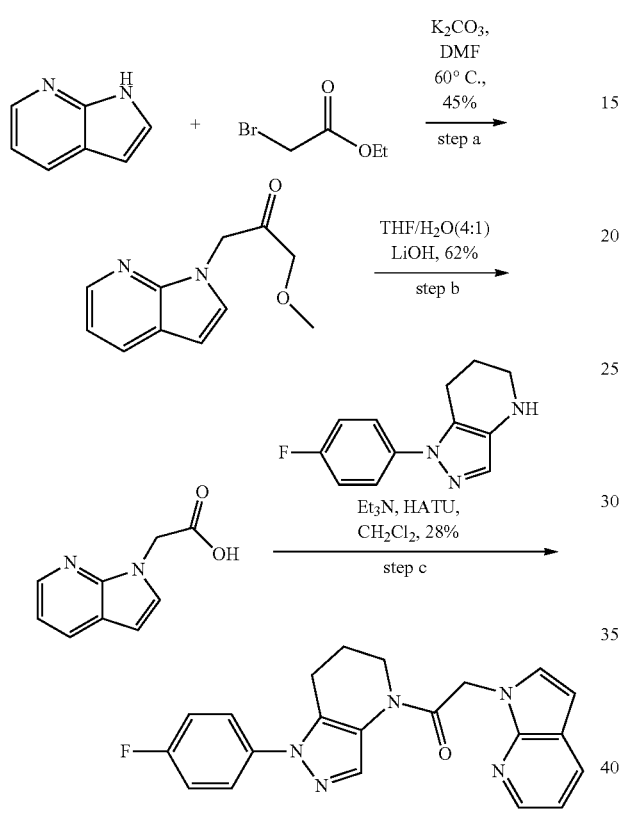

a) A mixture of 1H-pyrrolo[2,3-b]pyridine (471.2 mg, 4.0 mmol), ethyl 2-bromoacetate (530 µL, 4.8 mmol) and potassium carbonate (667.9 mg, 4.8 mmol) in DMF (5 mL) was heated at 60° C. for 2 hours with stirring. After cooling to room temperature, the reaction mixture was diluted with 20 ml of water, and extracted with EtOAc (2×30 mL). The combined organic layer was then washed with water (2×20 mL), dried (Na$_2$SO$_4$), filtered, and concentrated in vacuo. The crude residue was purified by flash chromatography (SiO$_2$, 40% ethyl acetate in hexanes) to afford the desired product (371.5 mg, 1.8 mmol, 45%).

b) A mixture of ethyl 2-pyrrolo[2,3-b]pyridin-1-ylacetate (371.5 mg, 1.8 mmol), and lithium hydroxide (87.9 mg, 3.6 mmol) in a mixture of THF (4 mL) and H$_2$O (1 mL) was stirred at room temperature overnight. The reaction mixture was concentrated in vacuo, and acidified to pH 5 with 3 N aqueous hydrochloric acid. The resulting solid was filtered, and washed with H$_2$O (2×10 mL), and dried in vacuo to afford the desired product (200.2 mg, 1.1 mmol, 62%).

c) A mixture of 2-pyrrolo[2,3-b]pyridin-1-ylacetic acid (51.2 mg, 0.24 mmol), 1-(4-fluorophenyl)-4,5,6,7-tetrahydropyrazolo[4,3-b]pyridine (50.3 mg, 0.29 mmol), triethyl amine (200 µL, 1.4 mmol), and HATU (110.7 mg, 0.29 mmol) in DMF (1 mL) was stirred at room temperature for 2 hours. The reaction mixture was then diluted with 10 mL of aqueous saturated sodium bicarbonate, and extracted with EtOAc (2×15 mL). The combined organic layers were then washed with water (2×20 mL), dried (Na$_2$SO$_4$), filtered, and concentrated in vacuo. The crude residue was purified by flash chromatography (SiO$_2$, 70% ethyl acetate in hexanes) to afford the desired product (25.9 mg, 0.07 mmol, 28%). $^1$H NMR (400 MHz, CDCl$_3$) δ 8.40 (s, 0.8H), 8.30 (dd, J=4.8, 1.6 Hz, 1H), 7.94 (dd, J=7.2, 1.6 Hz, 1H), 7.81 (s, 0.2H), 7.45 (m, 2H), 7.36 (d, J=3.6 Hz, 0.8H), 7.31 (d, J=3.6 Hz, 0.2H), 7.18 (m, 2H), 7.09 (dd, J=7.6, 4.8 Hz, 1H), 6.58 (d, J=3.6 Hz, 1H), 5.44 (s, 0.2H), 5.32 (s, 0.8H), 3.91 (m, 2H), 2.84 (m, 2H), 2.07 (m, 2H); MS: (ES) m/z calculated for $C_{21}H_{18}FN_5O$ [M+H]$^+$ 376.1, found 376.1.

Example 66

Synthesis of 1-[1-(4-fluorophenyl)-6,7-dihydro-5H-pyrazolo[4,3-b]pyridin-4-yl]-2-imidazo[4,5-b]pyridin-3-yl-ethanone

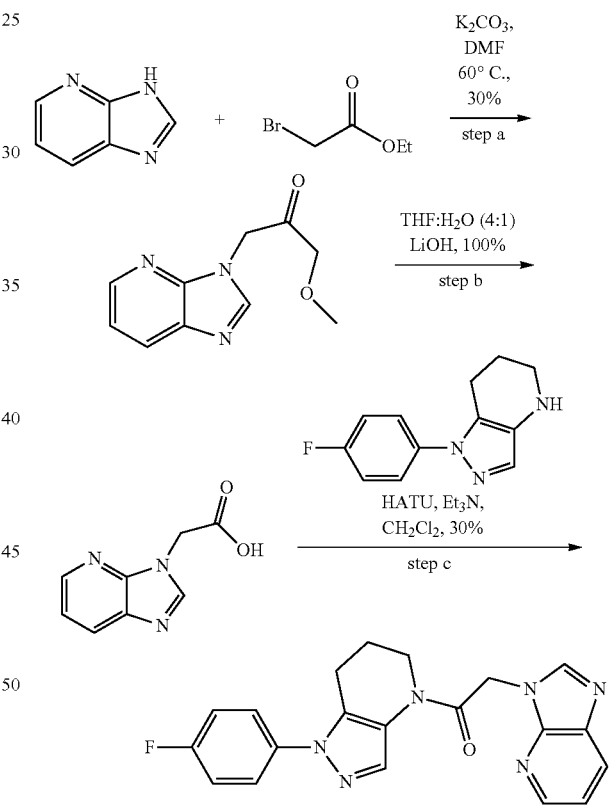

a) A mixture of 3H-imidazo[4,5-b]pyridine (952.7 mg, 8.0 mmol), ethyl 2-bromoacetate (1.0 mL, 9.6 mmol) and potassium carbonate (1.37 g, 9.6 mmol) in DMF (10 mL) was heated at 60° C. for 2 hours with stirring. After cooling to room temperature, the reaction mixture was diluted with 20 mL of water, and extracted with EtOAc (2×30 mL). The combined organic layers were then washed with water (2×20 mL), dried (Na$_2$SO$_4$), filtered, and concentrated in vacuo. The crude residue was purified by flash chromatography (SiO$_2$, 100% ethyl acetate to 10% MeOH in EtOAc) to afford the desired product (489.3 mg, 2.4 mmol, 30%).

b) A mixture of ethyl 2-imidazo[4,5-b]pyridin-3-ylacetate (400.3 mg, 1.9 mmol), and lithium hydroxide (96.7 mg, 4.0 mmol) in a mixture of THF (4 mL) and H$_2$O (1 ml) was stirred at room temperature overnight. The reaction mixture was concentrated in vacuo, and acidified to pH 5 with 3 N aqueous hydrochloric acid. The aqueous solution was then dried in vacuo to afford the crude product, which was used directly in the next step.

c) A mixture of 2-imidazo[4,5-b]pyridin-3-ylacetic acid (251.7 mg, excess), 1-(4-fluorophenyl)-4,5,6,7-tetrahydro-pyrazolo[4,3-b]pyridine (42.7 mg, 0.23 mmol), triethyl amine (200 μL, 1.4 mmol), and HATU (87.9 mg, 0.23 mmol) in DMF (1 mL) was stirred at room temperature for 2 hours. The reaction mixture was diluted with 10 mL of aqueous saturated sodium bicarbonate, and extracted with EtOAc (2×15 mL). The combined organic layers were then washed with water (2×20 mL), dried (Na$_2$SO$_4$), filtered, and concentrated in vacuo. The crude residue was purified by flash chromatography (SiO$_2$, 10% MeOH in EtOAc) to afford the desired product (26.1 mg, 0.07 mmol, 30%). $^1$H NMR (400 MHz, CDCl$_3$) δ 8.38 (d, J=7.2 Hz 1H), 8.50 (s, 0.8H), 8.25 (s, 0.2H), 8.12 (d, J=5.6 Hz, 1H), 7.45 (m, 2H), 7.28 (m, 1H), 7.15 (m, 2H), 5.46 (s, 0.2H), 5.33 (s, 0.8H), 3.95 (m, 2H), 2.88 (m, 2H), 2.15 (m, 2H); MS: (ES) m/z calculated for C$_{20}$H$_{17}$FN$_6$O [M+H]$^+$ 377.1, found 377.1.

Example 67

Synthesis of 2-[4-chloro-5-methyl-3-(methylsulfonyl)pyrazol-1-yl]-1-[1-(4-fluorophenyl)-6,7-dihydro-5H-pyrazolo[4,3-b]pyridin-4-yl]ethanone

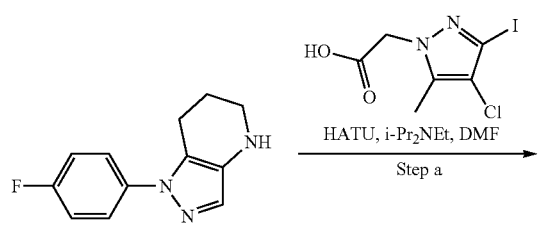

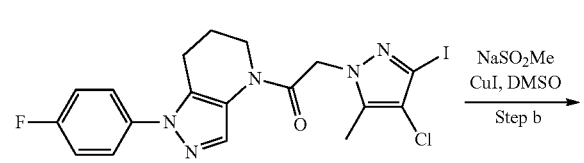

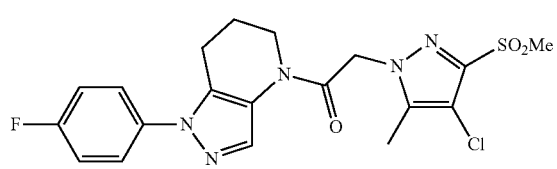

a) To a mixture of 1-(4-fluorophenyl)-4,5,6,7-tetrahydro-1H-pyrazolo[4,3-b]pyridine (303 mg, 1.40 mmol), 2-[4-chloro-5-methyl-3-(trifluoromethyl)pyrazol-1-yl]acetic acid (420 mg, 1.40 mmol), and i-Pr$_2$NEt (1 mL, 7.0 mmol) in DMF (5 mL) was added HATU (583 mg, 1.54 mmol). The resulting solution was then stirred at room temperature overnight. The reaction mixture was then diluted with EtOAc (50 mL) and washed with water (3×10 mL). The EtOAc layer was dried (Na$_2$SO$_4$), filtered, and concentrated in vacuo. The crude product (480 mg, 70%) was used directly in the next step.

b) A mixture of 2-(4-chloro-5-methyl-3-iodopyrazol-1-yl)-1-[1-(4-fluorophenyl)-6,7-dihydro-5H-pyrazolo[4,3-b] pyridin-4-yl]ethanone (85 mg, 0.17 mmol), NaSO$_2$Me (52 mg, 0.51 mmol), CuI (98 mg, 0.51 mmol) in DMSO (3 mL) was heated at 110° C. overnight. After cooling to room temperature, the reaction mixture was diluted with EtOAc (50 mL) and washed with water (3×10 mL). The EtOAc layer was dried (Na$_2$SO$_4$), filtered, concentrated in vacuo and purified by reverse phase HPLC (C18 column, acetonitrile-H$_2$O with 0.1% TFA as eluent) to give the desired product as white powder (42 mg, 55%). $^1$H NMR (400 MHz, DMSO-d$_6$) δ 8.15 (s, 1H), 7.60 (m, 2H), 7.38 (dd, J=8.9, 8.1 Hz, 2H), 5.58 (s, 2H), 3.80 (m, 2H), 3.28 (s, 3H), 2.83 (t, J=5.7 Hz, 2H), 2.22 (s, 3H), 2.00 (m, 2H); MS: (ES) m/z calculated for C$_{19}$H$_{20}$ClFN$_5$O$_3$S [M+H]$^+$ 452.1, found 452.0.

Example 68

Synthesis of 2-(4-chloro-5-methyl-3-cyanopyrazol-1-yl)-1-[1-(4-fluorophenyl)-6,7-dihydro-5H-pyrazolo[4,3-b]pyridin-4-yl]ethanone

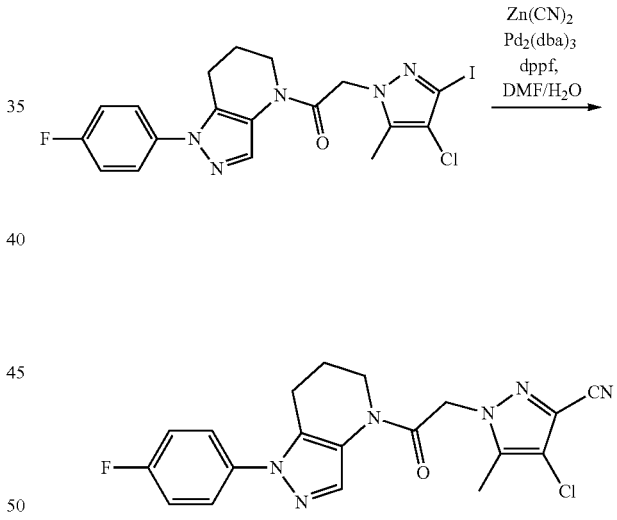

A mixture of 2-(4-chloro-5-methyl-3-iodopyrazol-1-yl)-1-[1-(4-fluorophenyl)-6,7-dihydro-5H-pyrazolo[4,3-b]pyridin-4-yl]ethanone (430 mg, 0.86 mmol), Zn(CN)$_2$ (151 mg, 1.3 mmol), dppf (72 mg, 0.14 mmol), and Pd$_2$(dba)$_3$ (79 mg, 0.09 mmol) in DMF (10 mL) and water (0.5 mL) was heated at 90° C. overnight. After cooling to room temperature, the reaction mixture was diluted with EtOAc (30 mL) and washed with water (3×5 mL). The EtOAc layer was dried (Na$_2$SO$_4$), filtered, and concentrated in vacuo. The residue was triturated with 1:1 CH$_2$Cl$_2$/MeOH (3×5 mL) to give the desired product as white powder (250 mg, 72%). $^1$H NMR (400 MHz, DMSO-d$_6$) δ 8.15 (s, 1H), 7.58 (m, 2H), 7.35 (dd, J=8.7, 8.1 Hz, 2H), 5.58 (s, 2H), 3.80 (m, 2H), 2.84 (t, J=5.4 Hz, 2H), 2.25 (s, 3H), 2.00 (m, 2H); MS: (ES) m/z calculated for C$_{19}$H$_{17}$ClF$_4$N$_5$O [M+H]$^+$ 399.1, found 399.1.

Example 69

Synthesis of 2-[4-chloro-3-(4,5-dihydro-1H-imidazol-2-yl)-5-methyl-pyrazol-1-yl]-1-[1-(4-fluorophenyl)-6,7-dihydro-5H-pyrazolo[4,3-b]pyridin-4-yl]ethanone trifluoroacetic acid salt

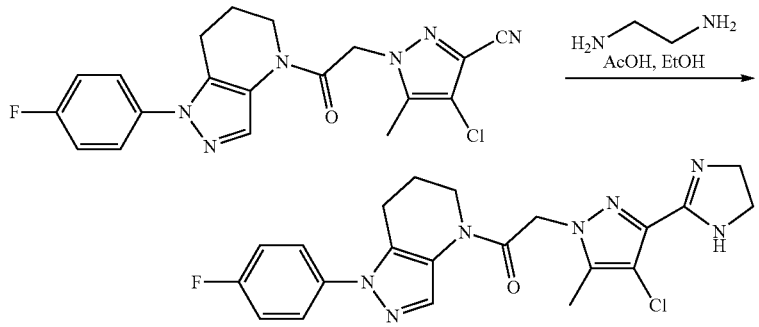

A mixture of 2-(4-chloro-5-methyl-3-cyanopyrazol-1-yl)-1-[1-(4-fluorophenyl)-6,7-dihydro-5H-pyrazolo[4,3-b]pyridin-4-yl]ethanone (150 mg, 0.38 mmol), ethylene diamine (2 mL) and acetic acid (0.3 mL) in ethanol (5 mL) was heated at 100° C. for 2 hours. After cooling to room temperature, the reaction mixture was diluted with $CH_2Cl_2$ (50 mL) and washed with water (3×10 mL). The organic layer was dried ($Na_2SO_4$), filtered, and concentrated in vacuo. Purification by reverse phase HPLC (C18 column, acetonitrile-$H_2O$ with 0.1% TFA as eluent) gave 2-[4-chloro-3-(4,5-dihydro-1H-imidazol-2-yl)-5-methyl-pyrazol-1-yl]-1-[1-(4-fluorophenyl)-6,7-dihydro-5H-pyrazolo[4,3-b]pyridin-4-yl]ethanone trifluoroacetic acid salt as white powder (84 mg, 51%). $^1$H NMR (400 MHz, DMSO-$d_6$) δ 10.21 (s, 2H), 8.15 (s, 1H), 7.58 (m, 2H), 7.37 (dd, J=8.7, 8.1 Hz, 2H), 5.60 (s, 2H), 3.92 (s, 4H), 3.82 (m, 2H), 2.89 (t, J=4.9 Hz, 2H), 2.29 (s, 3H), 2.01 (m, 2H); MS: (ES) m/z calculated for $C_{21}H_{22}ClFN_7O$ [M+H]$^+$ 442.2, found 442.1.

Example 70

Synthesis of 2-[4-chloro-3-(1H-imidazol-2-yl)-5-methyl-pyrazol-1-yl]-1-[1-(4-fluorophenyl)-6,7-dihydro-5H-pyrazolo[4,3-b]pyridin-4-yl]ethanone

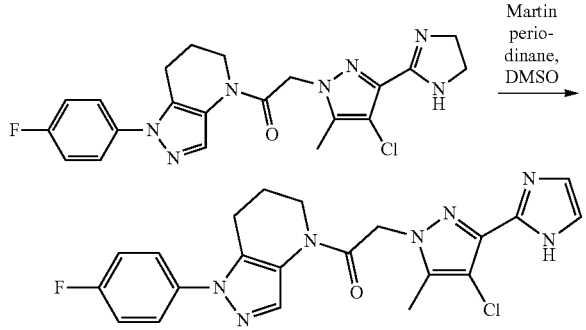

A mixture of 2-[4-chloro-3-(4,5-dihydro-1H-imidazol-2-yl)-5-methyl-pyrazol-1-yl]-1-[1-(4-fluorophenyl)-6,7-dihydro-5H-pyrazolo[4,3-b]pyridin-4-yl]ethanone (45 mg, 0.1 mmol), Dess-Martin periodinane (80 mg, 0.2 mmol) in DMSO (1 mL) was heated at 80° C. for 1 hour. After cooling to room temperature, the reaction mixture was diluted with $CH_2Cl_2$ (20 mL) and washed with water (3×5 mL). The organic layer was dried ($Na_2SO_4$), filtered, concentrated in vacuo and purified by reverse phase HPLC (C18 column, acetonitrile-$H_2O$ with 0.1% TFA as eluent) to give 2-[4-chloro-3-(1H-imidazol-2-yl)-5-methyl-pyrazol-1-yl]-1-[1-(4-fluorophenyl)-6,7-dihydro-5H-pyrazolo[4,3-b]pyridin-4-yl]ethanone as white powder (32 mg, 73%). $^1$H NMR (400 MHz, DMSO-$d_6$) δ 8.09 (s, 1H), 7.60 (s, 2H), 7.52 (m, 2H), 7.30 (dd, J=8.8, 8.3 Hz, 2H), 5.49 (s, 2H), 3.90 (m, 2H), 2.82 (t, J=5.1 Hz, 2H), 2.22 (s, 3H), 1.95 (m, 2H); MS: (ES) m/z calculated for $C_{21}H_{20}ClFN_7O$ [M+H]$^+$ 440.1, found 440.1.

Example 71

Synthesis of (2S)-1-[1-(4-fluorophenyl)-6,7-dihydro-5H-pyrazolo[4,3-b]pyridin-4-yl]-2-[2-methyl-4-(trifluoromethyl)imidazol-1-yl]propan-1-one

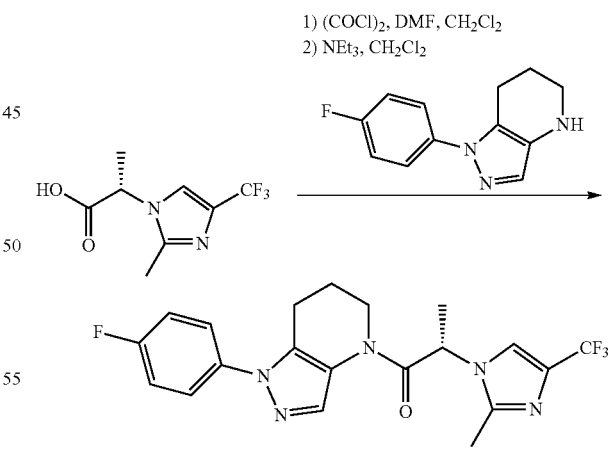

To a solution of (2S)-2-[2-methyl-4-(trifluoromethyl)imidazole-1-yl]propanoic acid (0.020 g, 0.09 mmol) in $CH_2Cl_2$ (3 mL) was added oxalyl chloride (0.040 mL, 0.46 mmol) and DMF (1 drop). After 20 min at room temperature, the mixture was concentrated in vacuo and the residue was added to another flask containing 1-(4-fluorophenyl)-4,5,6,7-tetrahydropyrazolo[4,3-b]pyridine (0.028 g, 0.13 mmol) and $NEt_3$ (0.060 mL, 0.43 mmol) in $CH_2Cl_2$ (3 mL). The resulting mixture was stirred at room temperature for 20 min, quenched with saturated aqueous NaHCO₃ solution (30 mL), and extracted with ethyl acetate (50 mL). The organic layer was dried over anhydrous sodium sulfate, concentrated in vacuo, and purified by flash chromatography (SiO₂, 0-8% MeOH/EtOAc) to afford the titled compound (0.030 g, 44%, TFA salt) as a white solid. $^1$H NMR (TFA salt) (400 MHz, CDCl₃) δ 9.70 (s, 1H), 8.43 (s, 1H), 7.78 (d, J=0.8 Hz, 1H), 7.42 (dd, J=9.2, 8.8 Hz, 2H), 7.20 (dd, J=8.8, 8.4 Hz, 2H), 5.61 (q, J=7.2 Hz, 1H), 3.89 (m, 2H), 2.84 (dd, J=6.2, 6.2 Hz, 2H), 2.65 (s, 3H), 2.15 (m, 2H), 1.84 (d, J=7.2 Hz, 3H); MS: (ES) m/z calculated for $C_{20}H_{19}F_4N_5O$ [M+H]⁺ (free form) 422.1, found 422.1; The titled compounds were analyzed by chiral normal phase chromatography (RegisPack, 25 cm×4.6 mm, 5 micron, cat#793104, 0.1% DEA/IPA, 0.7 mL/min). The (S)-enantiomer (major) had a retention time of 7.2 min and the (R)-enantiomer (minor) had a retention time of 6.2 min (isolated in 19:1 er).

Example 72

Synthesis of (2S)-1-[1-(4-chlorophenyl)-6,7-dihydro-5H-pyrazolo[4,3-b]pyridin-4-yl]-2-[2-methyl-4-(trifluoromethyl)imidazol-1-yl]propan-1-one

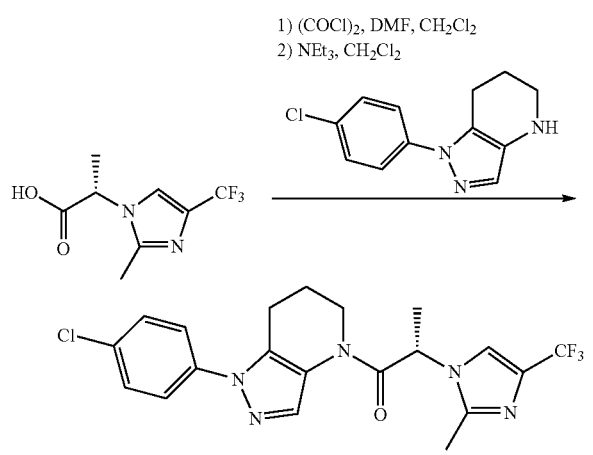

To a solution of (2S)-2-[2-methyl-4-(trifluoromethyl)imidazole-1-yl]propanoic acid (0.020 g, 0.09 mmol) in CH₂Cl₂ (1.5 mL) was added oxalyl chloride (0.050 mL, 0.58 mmol) and DMF (1 drop). After 20 min at room temperature, the mixture was concentrated in vacuo and the residue was added to another flask containing 1-(4-chlorophenyl)-4,5,6,7-tetrahydropyrazolo[4,3-b]pyridine (0.028 g, 0.13 mmol) and NEt₃ (0.050 mL, 0.35 mmol) in CH₂Cl₂ (1 mL). The resulting mixture was stirred at room temperature for 20 min, quenched with saturated aqueous NaHCO₃ solution (30 mL), and extracted with ethyl acetate (50 mL). The organic layer was dried over anhydrous sodium sulfate, concentrated in vacuo, and purified by flash chromatography (SiO₂, 0-6% MeOH/EtOAc) to afford the titled compound (0.022 g, 32%, TFA salt) as a white solid. $^1$H NMR (free form) (400 MHz, CDCl₃) δ 8.46 (s, 1H), 7.44 (m, 4H), 7.42 (dd, J=9.2, 8.8 Hz, 2H), 7.37 (d, J=1.2 Hz, 1H), 5.21 (q, J=7.2 Hz, 1H), 3.75 (m, 1H), 3.53 (m, 1H), 2.86 (dd, J=6.4, 6.4 Hz, 2H), 2.46 (s, 3H), 1.72 (d, J=6.8 Hz, 3H); MS: (ES) m/z calculated for $C_{20}H_{19}ClF_3N_5O$ [M+H]⁺ (free form) 438.1, found 438.1; The titled compounds were analyzed by chiral normal phase chromatography (RegisPack, 25 cm×4.6 mm, 5 micron, cat#793104, 0.1% DEA/IPA, 0.7 mL/min). The (S)-enantiomer (major) had a retention time of 8.4 min and the (R)-enantiomer (minor) had a retention time of 6.4 min (isolated in 18:1 er).

Example 73

Synthesis of 1-[1-(4-fluorophenyl)-6,7-dihydro-5H-pyrazolo[4,3-b]pyridin-4-yl]-2-[5-methyl-3-(trifluoromethyl)-1,2,4-triazol-1-yl]propan-1-one

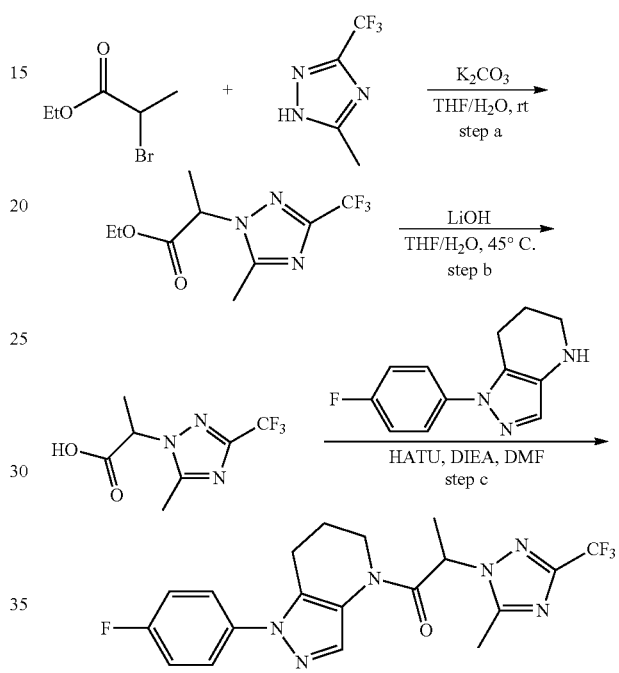

a) A solution of ethyl 2-bromopropionate (3.16 g, 17.5 mmol), 5-methyl-3-(trifluoromethyl)-1H-1,2,4-triazole (2.20 g, 14.6 mmol), and K₂CO₃ (4.00 g, 29.1 mmol) in THF/H₂O (2:1, 30 mL) was stirred at room temperature for 5 h. The mixture was diluted in EtOAc (50 mL). The organic layer was washed with water and brine, dried (MgSO₄), filtered, and concentrated in vacuo to give the desired product (4.0 g) as a colorless oil that was used in the next step without further purification.

b) The crude material from step a in THF (40 mL) was treated with 2 N LiOH (15 mL, 30 mmol) at 45° C. for 1 h and concentrated. The residue was diluted with water (20 mL), adjusted to pH 2 with 1 M H₂SO₄, and extracted with EtOAc (50 mL). The organic layer was dried (MgSO₄), filtered, and concentrated in vacuo to give the desired acid (2.56 g, 10.2 mmol, 70% over two steps) as a colorless solid.

c) To a mixture of 2-[5-methyl-3-(trifluoromethyl)-1,2,4-triazol-1-yl]propanoic acid (0.051 g, 0.23 mmol) and 1-(4-fluorophenyl)-4,5,6,7-tetrahydro-1H-pyrazolo[4,3-b]pyridine (0.050 g, 0.23 mmol) in DMF (1 mL) were added Hunig's base (0.059 g, 0.46 mmol) and 2-(1H-7-azabenzotriazol-1-yl)-1,1,3,3-tetramethyl uranium hexafluorophosphate methanaminium (HATU) (0.096 g, 0.25 mmol). The mixture was stirred at room temperature for 1 hour and then partitioned between water (4 mL) and ethyl acetate (6 mL). The organic layer was washed with brine, dried (Na₂SO₄), filtered, concentrated in vacuo, and purified by reverse phase HPLC (C18 column, acetonitrile-H₂O with 0.1% TFA as eluent) to give the desired product as a white solid (0.029 g, 0.069 mmol, 30%). $^1$H NMR (400 MHz, CDCl$_3$) δ 8.42 (s, 1H), 7.44 (ddd, J=10.4, 5.2, 2.8 Hz, 2H), 7.21-7.10 (m, 2H), 5.61 (q, J=7.1 Hz, 1H); 3.77 (ddd, J=12.6, 7.5, 3.0 Hz, 1H), 3.52 (ddd, J=12.5, 8.4, 3.0 Hz, 1H), 2.82 (td, J=6.4, 2.4 Hz, 2H), 2.52 (s, 3H), 2.10-1.80 (m, 5H); MS: (ES) m/z calculated for C$_{19}$H$_{18}$ClF$_3$N$_6$O [M+H]$^+$ 423.1, found 422.9.

Example 74

Synthesis of 1-[1-(4-chlorophenyl)-6,7-dihydro-5H-pyrazolo[4,3-b]pyridin-4-yl]-2-[5-methyl-3-(trifluoromethyl)-1,2,4-triazol-1-yl]propan-1-one

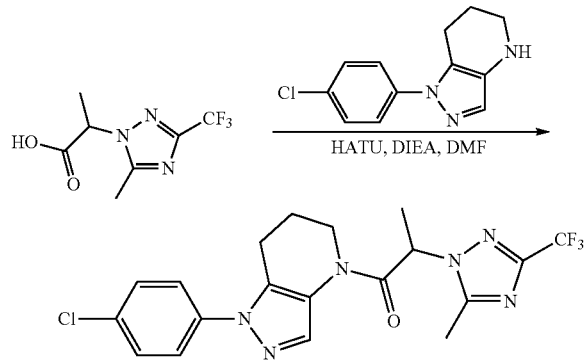

To a mixture of 2-[5-methyl-3-(trifluoromethyl)-1,2,4-triazol-1-yl]propanoic acid (0.048 g, 0.21 mmol) and 1-(4-chlorophenyl)-4,5,6,7-tetrahydro-1H-pyrazolo[4,3-b]pyridine (0.050 g, 0.21 mmol) in DMF (1 mL) were added Hunig's base (0.055 g, 0.42 mmol) and 2-(1H-7-azabenzotriazol-1-yl)-1,1,3,3-tetramethyl uranium hexafluorophosphate methanaminium (HATU) (0.090 g, 0.23 mmol). The mixture was stirred at room temperature for 1 hour, and then partitioned between water (4 mL) and ethyl acetate (6 mL). The organic layer was washed with brine, dried (Na$_2$SO$_4$), filtered, concentrated in vacuo, and purified by reverse phase HPLC (C18 column, acetonitrile-H$_2$O with 0.1% TFA as eluent) to give the desired product as a white solid (0.028 g, 0.063 mmol, 30%). $^1$H NMR (400 MHz, CDCl$_3$) δ 8.44 (s, 1H), 7.43 (s, 4H), 5.60 (q, J=7.1 Hz, 1H), 3.77 (ddd, J=12.6, 7.5, 3.0 Hz, 1H), 3.52 (ddd, J=12.3, 8.3, 3.0 Hz, 1H), 2.84 (tt, J=6.9, 3.3 Hz, 2H), 2.52 (s, 3H), 2.09-1.81 (m, 5H); MS: (ES) m/z calculated for C$_{19}$H$_{18}$ClF$_3$N$_6$O [M+H]$^+$ 439.1, found 438.9.

Example 75

This example illustrates the evaluation of the biological activity associated with compounds of interest (candidate compounds) of the invention.
Materials and Methods
  A. Cells
    1. CCR1 Expressing Cells
    a) THP-1 Cells
    THP-1 cells were obtained from ATCC (TIB-202) and cultured as a suspension in RPMI-1640 medium supplemented with 2 mM L-glutamine, 1.5 g/L sodium bicarbonate, 4.5 g/L glucose, 10 mM HEPES, 1 mM sodium pyruvate, 0.05% 2-mercaptoethanol and 10% FBS. Cells were grown under 5% CO$_2$/95% air, 100% humidity at 37° C. and subcultured twice weekly at 1:5 (cells were cultured at a density range of 2×10$^5$ to 2×10$^6$ cells/mL) and harvested at 1×10$^6$ cells/mL. THP-1 cells express CCR1 and can be used in CCR1 binding and functional assays.
    b) Isolated Human Monocytes
    Monocytes were isolated from human buffy coats using the Miltenyi bead isolation system (Miltenyi, Auburn, Calif.). Briefly, following a Ficoll gradient separation to isolate peripheral blood mononuclear cells, cells were washed with PBS and the red blood cells lysed using standard procedures. Remaining cells were labeled with anti-CD14 antibodies coupled to magnetic beads (Miltenyi Biotech, Auburn, Calif.). Labeled cells were passed through AutoMACS (Miltenyi, Auburn, Calif.) and positive fraction collected. Monocytes express CCR1 and can be used in CCR1 binding and functional assays.
  B. Assays
    1. Inhibition of CCR1 Ligand Binding
    CCR1 expressing cells were centrifuged and resuspended in assay buffer (20 mM HEPES pH 7.1, 140 mM NaCl, 1 mM CaCl$_2$, 5 mM MgCl$_2$, and with 0.2% bovine serum albumin) to a concentration of 5×10$^6$ cells/mL for THP-1 cells and 5×10$^5$ for monocytes. Binding assays were set up as follows. 0.1 mL of cells (5×10$^5$ THP-1 cells/well or 5×10$^4$ monocytes) was added to the assay plates containing the compounds, giving a final concentration of ~2-10 μM each compound for screening (or part of a dose response for compound IC$_{50}$ determinations). Then 0.1 mL of $^{125}$I labeled MIP-1α (obtained from Perkin Elmer Life Sciences, Boston, Mass.) or 0.1 mL of $^{125}$I labeled CCL15/leukotactin (obtained as a custom radiolabeling by Perkin Elmer Life Sciences, Boston, Mass.) diluted in assay buffer to a final concentration of ~50 pM, yielding ~30,000 cpm per well, was added (using $^{125}$I labeled MIP-1α with THP-1 cells and $^{125}$I labeled CCL15/leukotactin with monocytes), the plates sealed and incubated for approximately 3 hours at 4° C. on a shaker platform. Reactions were aspirated onto GF/B glass filters pre-soaked in 0.3% polyethyleneimine (PEI) solution, on a vacuum cell harvester (Packard Instruments; Meriden, Conn.). Scintillation fluid (40 μl; Microscint 20, Packard Instruments) was added to each well, the plates were sealed and radioactivity measured in a Topcount scintillation counter (Packard Instruments). Control wells containing either diluent only (for total counts) or excess MIP-1α or MIP-1β (1 μg/mL, for non-specific binding) were used to calculate the percent of total inhibition for compound. The computer program Prism from GraphPad, Inc. (San Diego, Calif.) was used to calculate IC$_{50}$ values. IC$_{50}$ values are those concentrations required to reduce the binding of labeled MIP-1α to the receptor by 50%. (For further descriptions of ligand binding and other functional assays, see Dairaghi, et al., J. Biol. Chem. 274:21569-21574 (1999), Penfold, et al., Proc. Natl. Acad. Sci. USA. 96:9839-9844 (1999), and Dairaghi, et al., J. Biol. Chem. 272:28206-28209 (1997)).
    2. Calcium Mobilization
    To detect the release of intracellular stores of calcium, cells (THP-1 or monocytes) were incubated with 3 μM of INDO-1AM dye (Molecular Probes; Eugene, Oreg.) in cell media for 45 minutes at room temperature and washed with phosphate buffered saline (PBS). After INDO-1AM loading, the cells were resuspended in flux buffer (Hank's balanced salt solution (HBSS) and 1% FBS). Calcium mobilization was measured using a Photon Technology International spectrophotometer (Photon Technology International; New Jersey) with excitation at 350 nm and dual simultaneous recording of fluorescence emission at 400 nm and 490 nm. Relative intracellular calcium levels were expressed as the 400 nm/490 nm emission ratio. Experiments were performed at 37° C. with constant mixing in cuvettes each containing $10^6$ cells in 2 mL of flux buffer. The chemokine ligands may be used over a range from 1 to 100 nM. The emission ratio was plotted over time (typically 2-3 minutes). Candidate ligand blocking compounds (up to 10 µM) were added at 10 seconds, followed by chemokines at 60 seconds (i.e., MIP-1α; R&D Systems; Minneapolis, Minn.) and control chemokine (i.e., SDF-1α; R&D Systems; Minneapolis, Minn.) at 150 seconds.

3. Chemotaxis Assays

Chemotaxis assays were performed using 5 µm pore polycarbonate, polyvinylpyrrolidone-coated filters in 96-well chemotaxis chambers (Neuroprobe; Gaithersburg, Md.) using chemotaxis buffer (Hank's balanced salt solution (HBSS) and 1% FBS). CCR1 chemokine ligands (i.e., MIP-1α, CCL15/Leukotactin; R&D Systems; Minneapolis, Minn.) are use to evaluate compound mediated inhibition of CCR1 mediated migration. Other chemokines (i.e., SDF-1α; R&D Systems; Minneapolis, Minn.) are used as specificity controls. The lower chamber was loaded with 29 µl of chemokine (i.e., 0.1 nM CCL15/Leukotactin) and varying amounts of compound; the top chamber contained 100,000 THP-1 or monocyte cells in 20 µl. The chambers were incubated 1-2 hours at 37° C., and the number of cells in the lower chamber quantified either by direct cell counts in five high powered fields per well or by the CyQuant assay (Molecular Probes), a fluorescent dye method that measures nucleic acid content, and by measuring with a Spectrafluor Plus (Tecan). The computer program Prism from GraphPad, Inc. (San Diego, Calif.) was used to calculate $IC_{50}$ values. $IC_{50}$ values are those compound concentrations required to inhibit the number of cells responding to a CCR1 agonist by 50%.

4. In Vivo Efficacy a) Rabbit Model of Destructive Joint Inflammation

A rabbit LPS study was conducted essentially as described in Podolin, et al. *J. Immunol.* 169(11):6435-6444 (2002). Female New Zealand rabbits (approximately 2 kilograms) were treated intra-articularly in both knees with LPS (10 ng). The compound of interest, for example 1.016, (formulated in 1% methocel) or vehicle (1% methocel) was dosed orally at a 5 ml/kg dose volume at two times (2 hours before the intra-articular LPS injection and 4 hours after the intra-articular LPS injection). Sixteen hours after the LPS injection, knees were lavaged and cells counts were performed. Beneficial effects of treatment were determined by reduction in the number of inflammatory cells recruited to the inflamed synovial fluid of the knee joints. Treatment with the compound of interest resulted in a significant reduction in recruited inflammatory cells.

b) Evaluation of a Compound of Interest in a Rat Model of Collagen Induced Arthritis A 17 day developing type II collagen arthritis study is conducted to evaluate the effects of a compound of interest on arthritis induced clinical ankle swelling. Rat collagen arthritis is an experimental model of polyarthritis that has been widely used for preclinical testing of numerous anti-arthritic agents (see Trentham, et al., *J. Exp. Med.* 146(3):857-868 (1977), Bendele, et al., *Toxicologic Pathol.* 27:134-142 (1999), Bendele, et al., *Arthritis Rheum.* 42:498-506 (1999)). The hallmarks of this model are reliable onset and progression of robust, easily measurable polyarticular inflammation, marked cartilage destruction in association with pannus formation and mild to moderate bone resorption and periosteal bone proliferation.

Female Lewis rats (approximately 0.2 kilograms) are anesthetized with isoflurane and injected with Freund's Incomplete Adjuvant containing 2 mg/mL bovine type II collagen at the base of the tail and two sites on the back on days 0 and 6 of this 17 day study. A compound of interest is dosed daily in a sub-cutaneous manner from day 0 till day 17 at a efficacious dose. Caliper measurements of the ankle joint diameter are taken, and reduced joint swelling is taken as a measure of efficacy.

Murine Model of Dermatological Disease

Compounds of the invention can be assessed in the murine model of dermal delayed type hypersensitivity induced by oxazolone. Briefly, 8-10 week old BALB/c mice are sensitized topically with a 1% solution of oxazolone dissolved in ethanol on their shaved abdomens on day 0. On day 6 post sensitization mice are dosed orally with either vehicle or increasing doses of a compound of the invention immediately prior to and 4 hours following a topical challenge with a 0.5% solution of oxazolone in ethanol on the right ear. The following day (day 7), ear thicknesses are measured using caliper measurements. Animals treated with compound have significantly reduced ear swelling compared to vehicle treated controls indicating a compound mediated decrease in oxazolone induced dermal hypersensitivity.

Murine Asthma Model

Compounds of the invention can be assessed in the murine model of allergic asthma. Asthma is induced in 8-10 week old BALB/c mice by sensitizing mice with OVA in Alum adjuvant on days 0 and 10. On day 20 mice are challenged with OVA in PBS intranasally to elicit airway inflammation. Groups of mice are either treated with vehicle, or increasing doses of a compound of the invention starting on day 20 and lasting until day 23. Animals are analyzed at day 23 after the intranasal OVA challenge for cellular infiltrates in bronchioalveolar lavage (BAL). A significant reduction in BAL leukocyte numbers relative to vehicle treated mice indicates the compound is effective in this model.

Murine Model of Cancer

This example describes a procedure to evaluate efficacy of CCR1 antagonists for treatment of malignancy. Normal mouse strains can be transplanted with a variety of well-characterized mouse tumor lines, including a mouse thymoma EL4 which has been transfected with OVA to allow easy evaluation of tumor specific antigen responses following vaccination with OVA. Three series of mouse groups from any of these tumor models are tested for CCR1 antagonist efficacy as follows: One series of mice additionally receives PBS and Tween 0.5% i.p. soon after tumor transplant, and thereafter at varying dosing schedules. A second series consists of groups of mice receiving different doses of the CCR1 antagonist given either intra-peritoneally, intra-venously, sub-cutaneously, intramuscularly, orally, or via any other mode of administration soon after tumor transplant, and thereafter at varying dosing schedules. A third series of mice, serving as positive control, consists of groups treated with either anti-IL4 antibodies, anti-IFNg antibodies, IL4, or TNF, given i.p. soon after tumor transplant, and thereafter at varying dosing schedules. Efficacy is monitored via tumor growth versus regression. In the case of the OVA-transfected EL4 thymoma model, cytolytic OVA-specific responses can be measured by stimulating draining lymph node cells with OVA in vitro, and measuring antigen-specific cytotoxicity at 72 hours.

Murine Model of Inflammatory Bowel Diseases

The MDR1a-knockout mice, which lack the P-glycoprotein gene, spontaneously develop colitis under specific pathogen-free condition. The pathology in these animals has been characterized as Th1-type T cell-mediated inflammation similar to ulcerative colitis in humans. Disease normally begins to develop at around 8-10 weeks after birth. However the ages at which disease emerges and the ultimate penetrance level often vary considerably among different animal facilities. In a study using the MDR1a-knockout mice, a CCR1 antagonist can be evaluated prophylacticly or therapeutically depending on time of administration. Female mice (n=34) are dosed with a compound of interest as appropriate to the compound eg daily in a sub-cutaneous manner at a efficacious dose. The study is evaluated for IBD associated growth retardation and scoring of anal discharge and irritation. A compound which reduces anal discharge and irritation or inhibits IBD associated growth retardation indicates efficacy of compound in this indication.

Murine Model of Solid Tumors

The mouse RENCA tumor model accurately mimics the progression of human adult renal cell carcinoma specifically with reference to spontaneous metastasis to lungs and serves as a model for solid tumors. Balb/c 6-8 week old female mice are inoculated with approximately 5e5 RENCA cells (mouse renal adenocarcinoma; ATCC cat# CRL-2947) under the kidney capsule and kidney tumor growth is observed over 22 days, with lung metastasis observed as early as day 15. Animals are dosed with either vehicle or a compound of the invention eg daily subcutaneously, from the time of tumor implantation to monitor effects on primary growth, or at a later time (eg day 7) to monitor the compound effect on metastasis. Primary tumor areas are measured twice a week using mechanical calipers. Tumor volumes are calculated by the formula v=pab2/6, where a is the longest diameter and b is the next longest diameter perpendicular to a. A reduction in tumor volume or incidence of metastasis indicates efficacy of compound in this indication.

Murine Model of Radiation-Induced Pulmonary Disease (RIPD)

Various models can be used to assess the efficacy of a compound of the invention in recovery from RIPD. For instance Tokuda et al describe a model of bleomycin induced lung fibrosis (Tokuda et al, J Immunol. 164(5):2745-51 (2000)). Alternatively Yang et al describe a model of direct radiation induced disease (Yang et al, Am J Respir Cell Mol Biol. 45(1):127-35 (2011)). Briefly, anesthetized compound treated or untreated mice aged 10-12 weeks are immobilized, all but the thoracic cavity lead shielded and animals irradiated with a single dose of 14.5 Gy from a cesium source at 1.65 Gy/min. At this dose, survival is sufficient to permit adequate numbers of animals for long-term analyses. Efficacy of compound can be assessed by many methods know in the art, including lung mechanical assessment, lung hydroxyproline levels and others.

In the table below, structures and activity are provided for representative compounds described herein. Activity is provided as follows for either the chemotaxis assay or binding assay as described above: +, $IC_{50}>12.5$ uM; ++, 2500 nM<$IC_{50}$<12.5 uM; +++, 1000 nM<$IC_{50}$<2500 nM; and ++++, $IC_{50}$<1000 nM.

TABLE 1

Specific Examples

| Example | CTX IC50 (nM) |
|---|---|
| 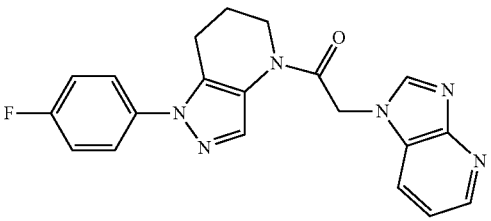<br>1.001 | ++ |
| 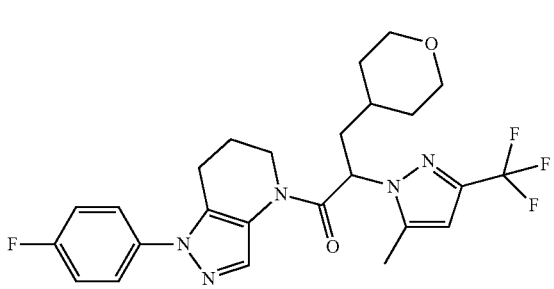<br>1.002 | ++++ |
| 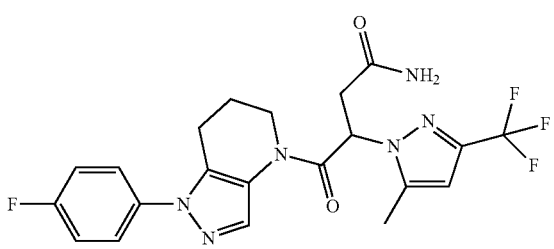<br>1.003 | ++++ |

TABLE 1-continued
Specific Examples
| Example | CTX IC50 (nM) |
|---|---|
| 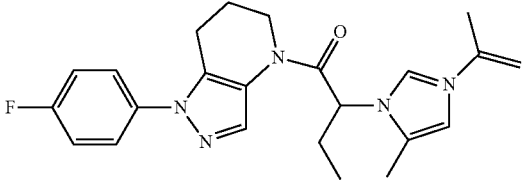<br>1.004 | ++++ |
| 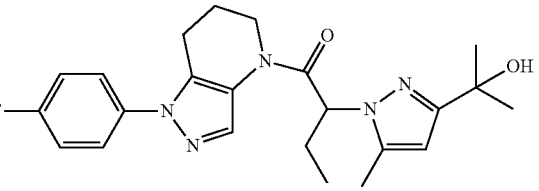<br>1.005 | ++++ |
| 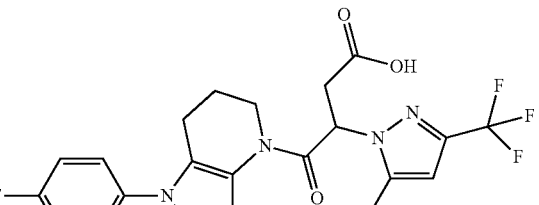<br>1.006 | ++ |
| 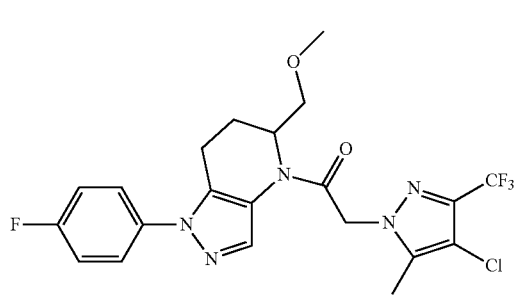<br>1.007 | ++++ |
| 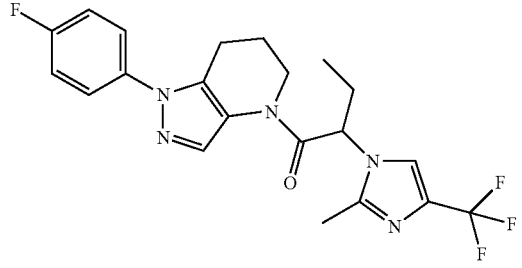<br>1.008 | ++++ |

TABLE 1-continued
| Example | CTX IC50 (nM) |
|---|---|
| 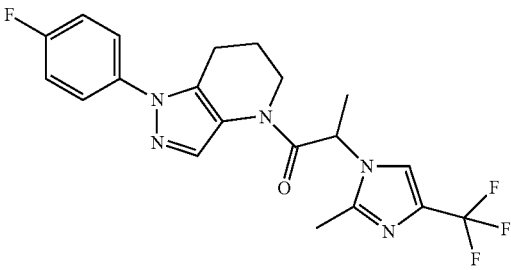<br>1.009 | ++++ |
| 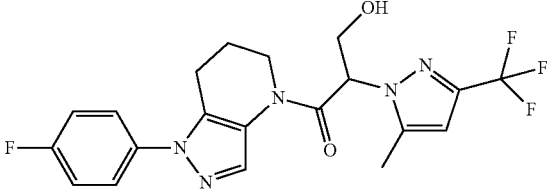<br>1.010 | ++++ |
| 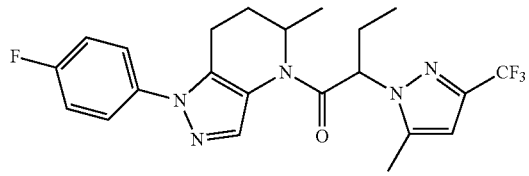<br>1.011 | ++++ |
| 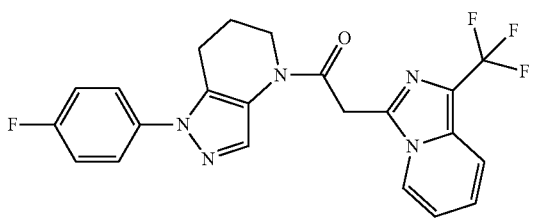<br>1.012 | ++++ |
| 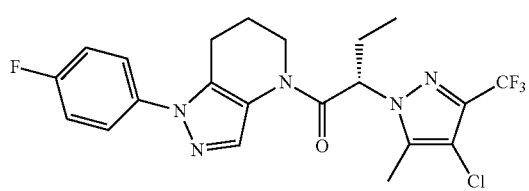<br>1.013 | ++++ |
| 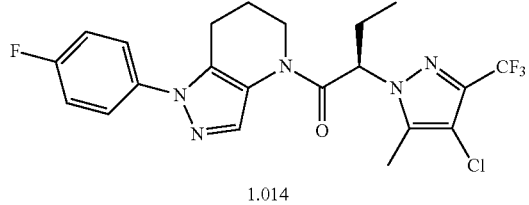 [SMILES: CC[C@H](C(=O)N1CCCc2c1cnn2-c1ccc(F)cc1)n1nc(C(F)(F)F)c(Cl)c1C]<br>1.014 | ++++ |

TABLE 1-continued
Specific Examples
| Example | CTX IC50 (nM) |
|---|---|
| 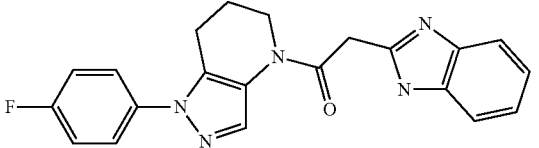<br>1.015 | ++++ |
| 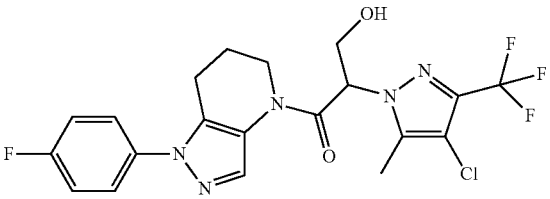<br>1.016 | ++++ |
| 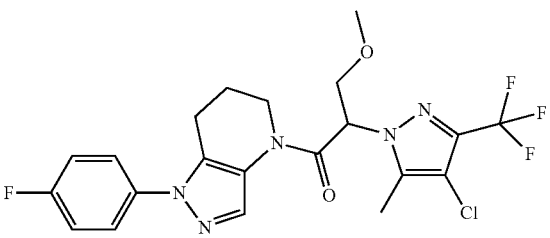<br>1.017 | ++++ |
| 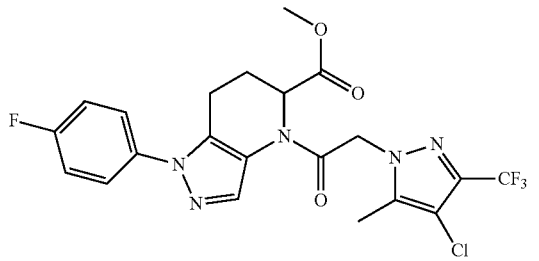<br>1.018 | ++++ |
| 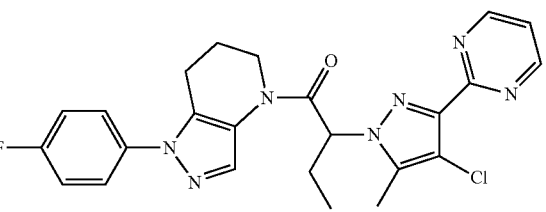<br>1.019 | ++++ |
| 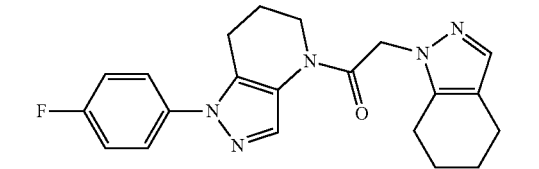<br>1.020 | ++++ |

TABLE 1-continued

Specific Examples

| Example | CTX IC50 (nM) |
|---|---|
| 1.021 | ++++ |
| 1.022 | ++++ |
| 1.023 | ++++ |
| 1.024 | ++++ |
| 1.025 | ++++ |
| 1.026 | ++++ |

TABLE 1-continued

Specific Examples

| Example | CTX IC50 (nM) |
|---|---|
| 1.027 | ++++ |
| 1.028 | ++++ |
| 1.029 | ++++ |
| 1.030 | ++++ |
| 1.031 | + |
| 1.032 | ++++ |

TABLE 1-continued
Specific Examples
| Example | CTX IC50 (nM) |
|---|---|
| 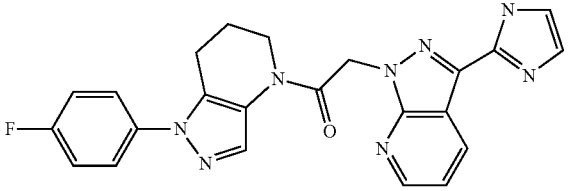 1.033 | ++++ |
| 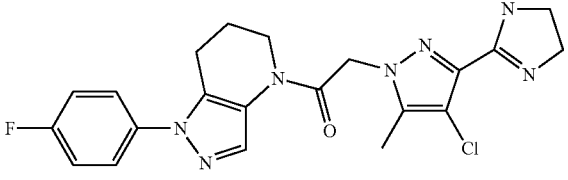 1.034 | ++++ |
| 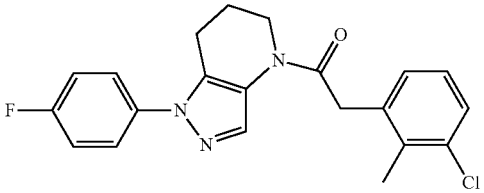 1.035 | + |
| 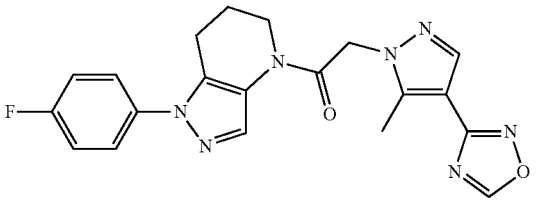 1.036 | ++++ |
| 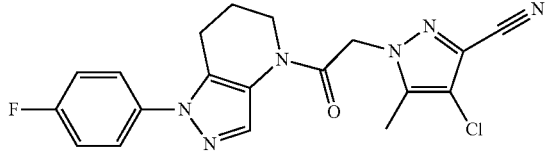 1.037 | ++++ |
| 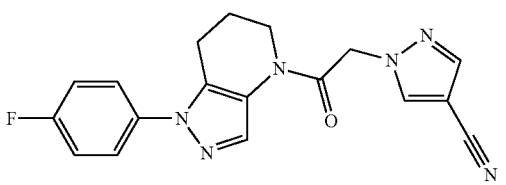 1.038 | ++ |

TABLE 1-continued
| Example | CTX IC50 (nM) |
|---|---|
| 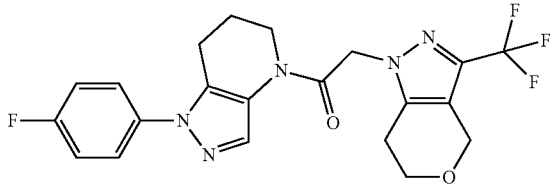 1.039 | ++++ |
| 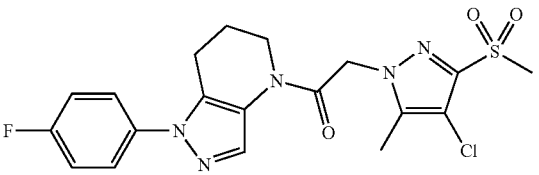 1.040 | ++++ |
| 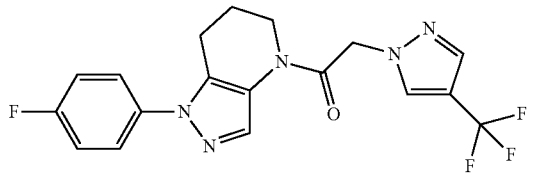 1.041 | ++++ |
| 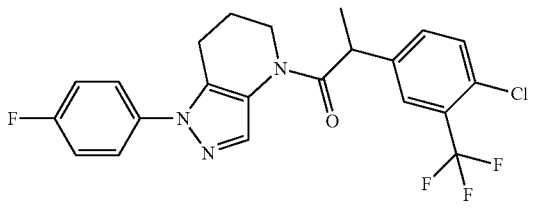 1.042 | ++++ |
| 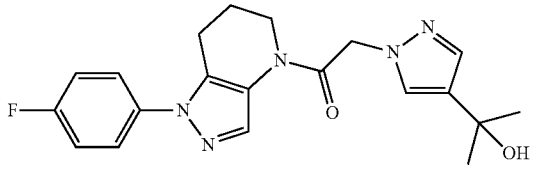 1.043 | ++ |
| 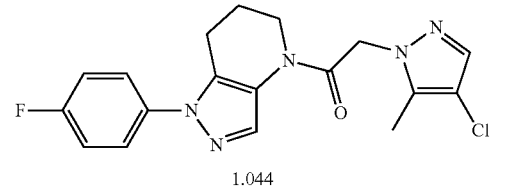 [SMILES: O=C(Cn1cc(Cl)cn1)N1CCCc2c1cnn2-c1ccc(F)cc1] 1.044 | ++++ |

TABLE 1-continued

Specific Examples

| Example | CTX IC50 (nM) |
|---|---|
| 1.045 | ++++ |
| 1.046 | ++++ |
| 1.047 | ++++ |
| 1.048 | ++++ |
| 1.049 | ++++ |
| 1.050 | ++++ |
| 1.051 | ++++ |

TABLE 1-continued
Specific Examples
| Example | CTX IC50 (nM) |
|---|---|
| 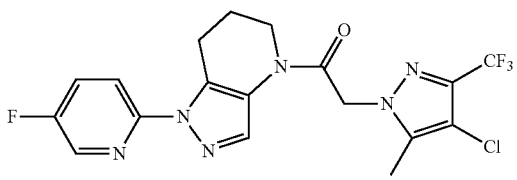<br>1.052 | ++++ |
| 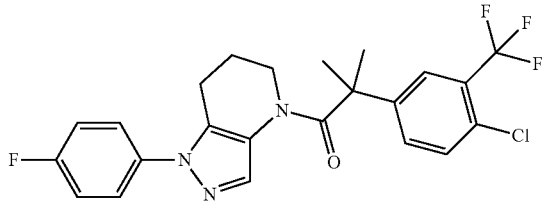<br>1.053 | ++++ |
| 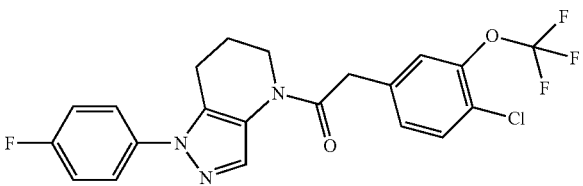<br>1.054 | ++++ |
| 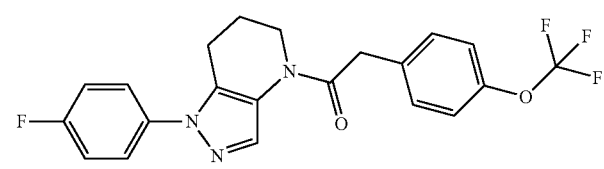<br>1.055 | ++++ |
| 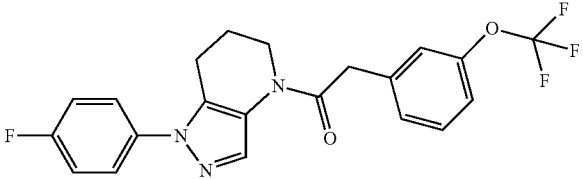<br>1.056 | +++ |
| 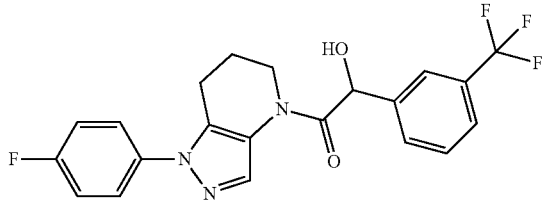<br>1.057 | +++ |

TABLE 1-continued
Specific Examples
| Example | CTX IC50 (nM) |
|---|---|
| 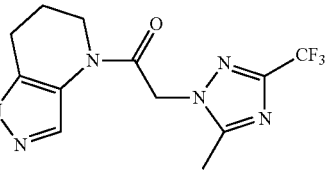<br>1.058 | ++++ |
| 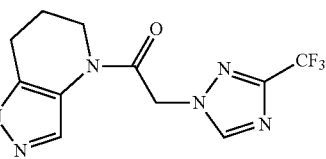<br>1.059 | ++++ |
| 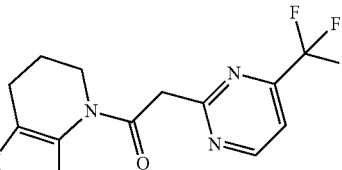<br>1.060 | ++ |
| 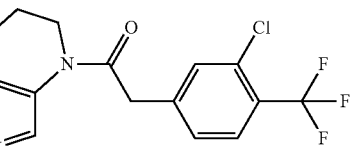<br>1.061 | ++++ |
| 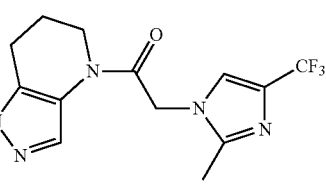<br>1.062 | ++++ |
| 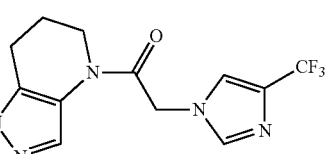<br>1.063 | ++++ |
| 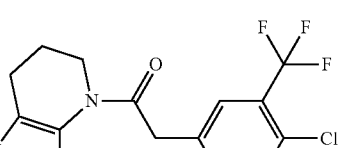<br>1.064 | ++++ |

TABLE 1-continued
Specific Examples
| Example | CTX IC50 (nM) |
|---|---|
| 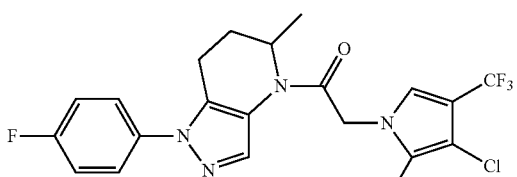<br>1.065 | ++++ |
| 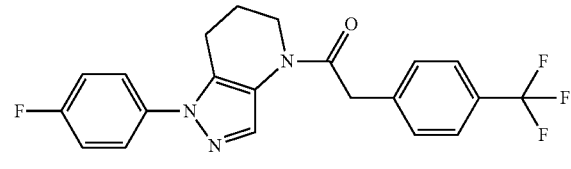<br>1.066 | ++++ |
| 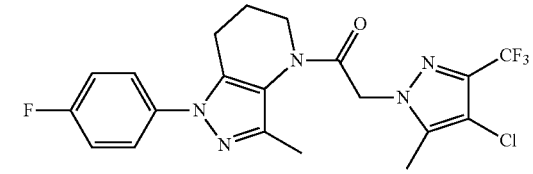<br>1.067 | ++++ |
| 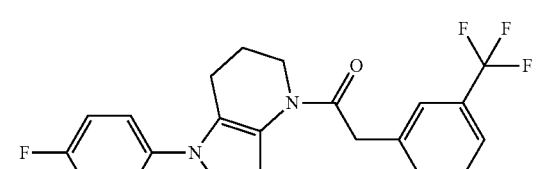<br>1.068 | ++++ |
| 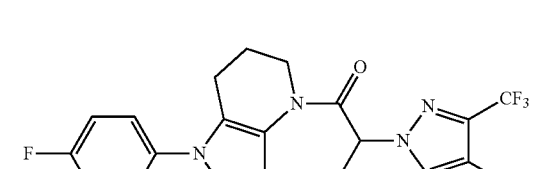<br>1.069 | ++++ |
| 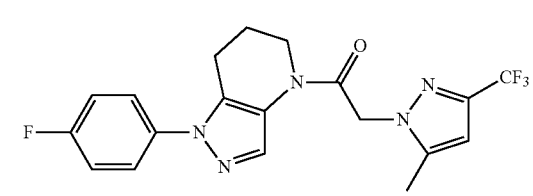<br>1.070 | ++++ |

TABLE 1-continued
Specific Examples
| Example | CTX IC50 (nM) |
|---|---|
| 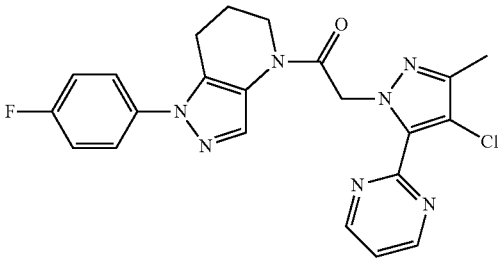<br>1.071 | ++++ |
| 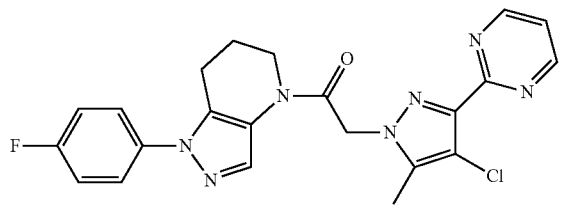<br>1.072 | ++++ |
| 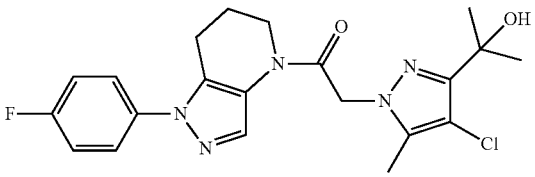<br>1.073 | ++++ |
| 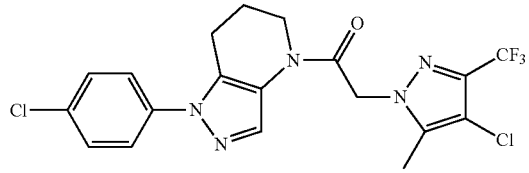<br>1.074 | ++++ |
| 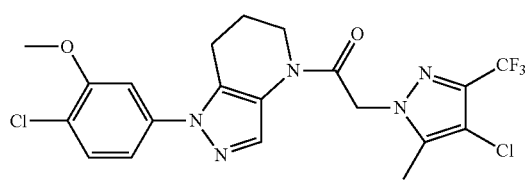<br>1.075 | ++++ |
| 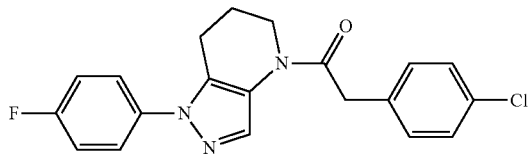<br>1.076 | ++++ |

TABLE 1-continued
Specific Examples
| Example | CTX IC50 (nM) |
|---|---|
| 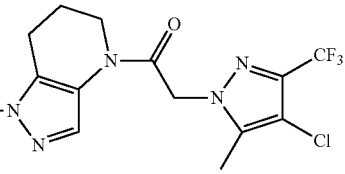 1.077 | ++++ |
| 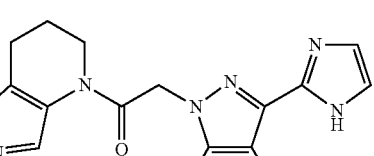 1.078 | ++++ |
| 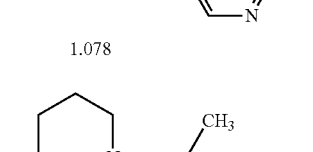 1.079 | ++++ |
| 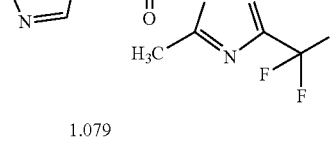 1.080 | ++++ |
| 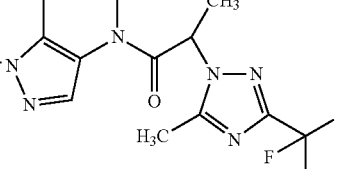 1.081 | ++++ |
| 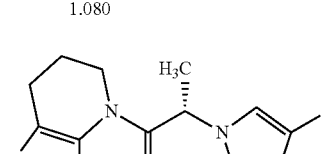 1.082 | ++++ |

What is claimed is:

1. A compound having a formula:

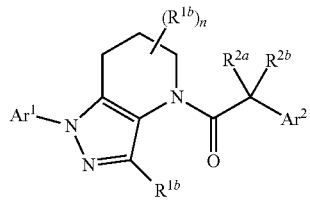

(I)

wherein the subscript n is an integer of from 0 to 3;

each $R^{1a}$ and $R^{1b}$ is a member independently selected from the group consisting of H, $C_{1-8}$ alkyl, $C_{1-8}$ haloalkyl, $C_{3-6}$ cycloalkyl, —$COR^a$, —$CO_2R^a$, —$CONR^aR^b$, —$NR^aR^b$, —$NR^aCOR^b$, —$OR^a$, —$X^1COR^a$, —$X^1CO_2R^a$, —$X^1CONR^aR^b$, —$X^1NR^aCOR^b$, —$X^1NR^aR^b$, and —$X^1OR^a$, wherein $X^1$ is a member selected from the group consisting of $C_{1-4}$ alkylene, and each $R^a$ and $R^b$ is independently selected from the group consisting of hydrogen, $C_{1-8}$ alkyl, $C_{1-8}$ haloalkyl, and $C_{3-6}$ cycloalkyl, and optionally two $R^{1a}$ groups on adjacent carbon atoms are joined to form a 5-, 6- or 7-membered carbocyclic or heterocyclic ring;

each of $R^{2a}$ and $R^{2b}$ is a member independently selected from the group consisting of H, hydroxyl, $C_{1-8}$ alkyl, $C_{1-8}$ haloalkyl, $C_{1-8}$ alkoxy, $C_{1-4}$ alkoxy-$C_{1-4}$ alkyl, $C_{1-8}$ hydroxyalkyl, $C_{1-4}$ alkoxy-$C_{1-4}$ alkoxy, $C_{3-6}$ cycloalkyl, $C_{3-6}$ cycloalkyl-$C_{1-4}$ alkyl, 3- to 7-membered heterocycloalkyl, 3- to 7-membered heterocycloalkyl-$C_{1-4}$ alkyl, —$X^1CO_2R^a$, —$X^1CONR^aR^b$, —$X^1NR^aCOR^b$, —$X^1NR^aR^b$, wherein $X^1$, $R^a$ and $R^b$ are defined above;

$Ar^1$ is a member selected from the group consisting of phenyl, naphthyl and pyridyl, each of which is substituted with from one to five substituents, $R^3$, $R^{3a}$, $R^{3b}$, $R^4$ and $R^{4a}$ which are independently selected from the group consisting of H, halogen, —$OR^c$, —$OC(O)R^c$, —$NR^cR^d$, —$SR^c$, —$R^e$, —$CN$, —$NO_2$, —$CO_2R^c$, —$CONR^cR^d$, —$C(O)R^c$, —$OC(O)NR^cR^d$, —$NR^dC(O)$ $R^c$, —$NR^dC(O)_2R^e$, —$NR^c$—$C(O)NR^cR^d$, —$NH$—$C(NH_2)$=$NH$, —$NR^eC(NH_2)$=$NH$, —$NH$—$C(NH_2)$=$NR^e$, —$NH$—$C(NHR^e)$=$NH$, —$S(O)R^e$, —$S(O)_2$ $R^e$, —$NR^cS(O)_2R^e$, —$S(O)_2NR^cR^d$, —$N_3$, —$X^2OR^c$, —$O$—$X^2OR^c$, —$X^2OC(O)R^c$, —$X^2NR^cR^d$, —$O$—$X^2NR^cR^d$, —$X^2SR^c$, —$X^2CN$, —$X^2NO_2$, —$X^2CO_2R^c$, —$O$—$X^2CO_2R^c$, —$X^2CONR^cR^d$, —$O$—$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)$ $NR^cR^d$, —$X^2NH$—$C(NH_2)$=$NH$, —$X^2NR^eC(NH_2)$=$NH$, —$X^2NH$—$C(NH_2)$=$NR^e$, —$X^2NH$—$C(NHR^e)$=$NH$, —$X^2S(O)R^e$, —$X^2S(O)_2R^e$, —$X^2NR^cS(O)_2R^e$, —$X^2S(O)_2NR^cR^d$, —$X^2N_3$, —$NR^d$—$X^2OR^c$, —$NR^d$—$X^2NR^cR^d$, —$NR^d$—$X^2CO_2R^c$, and —$NR^d$—$X^2CONR^cR^d$, wherein each $X^2$ is a member independently selected from the group consisting of $C_{1-4}$ alkylene, and each $R^c$ and $R^d$ is independently selected from hydrogen, $C_{1-8}$ alkyl, $C_{1-8}$ hydroxyalkyl, $C_{1-8}$ haloalkyl and $C_{3-6}$ cycloalkyl, or optionally $R^c$ and $R^d$ when attached to the same nitrogen atom can be combined with the nitrogen atom to form a five or six-membered ring having from 0 to 2 additional heteroatoms as ring members; and each $R^e$ is independently selected from the group consisting of $C_{1-8}$ alkyl, $C_{1-8}$ hydroxyalkyl, $C_{1-8}$ haloalkyl and $C_{3-6}$ cycloalkyl;

$Ar^2$ is a member selected from the group consisting of a six- or ten-membered monocyclic or fused bicyclic aryl ring, and a five- to ten-membered monocyclic or fused bicyclic heteroaryl ring; each of which is substituted with from one to five substituents, $R^5$, $R^6$, $R^7$, $R^8$ and $R^9$, independently selected from the group consisting of H, halogen, —$OR^f$, —$OC(O)R^f$, —$NR^fR^g$, —$SR^f$, —$R^h$, —$CN$, —$NO_2$, —$CO_2R^f$, —$CONR^fR^g$, —$C(O)R^f$, —$OC(O)NR^fR^g$, —$NR^gC(O)R^f$, —$NR^gC(O)_2R^h$, —$NR^f$—$C(O)NR^fR^g$, —$NH$—$C(NH_2)$=$NH$, —$NR^hC(NH_2)$=$NH$, —$NH$—$C(NH_2)$=$NR^h$, —$NH$—$C(NHR^h)$=$NH$, —$S(O)R^h$, —$S(O)_2R^h$, —$NR^fS(O)_2R^h$, —$S(O)_2NR^fR^g$, —$NR^fS(O)_2NR^fR^g$, —$N_3$, —$X^3OR^f$, —$X^3OC(O)R^f$, —$X^3NR^fR^g$, —$X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2$ $R^h$, —$X^3NR^f$—$C(O)NR^fR^g$, —$X^3NH$—$C(NH_2)$=$NH$, —$X^3NR^hC(NH_2)$=$NH$, —$X^3NH$—$C(NH_2)$=$NR^h$, —$X^3NH$—$C(NHR^h)$=$NH$, —$X^3S(O)R^h$, —$X^3S(O)_2$ $R^h$, —$X^3NR^fS(O)_2R^h$, —$X^3S(O)_2NR^fR^g$, —$Y$, —$X^3Y$, —$S(O)_2Y$, —$C(O)Y$, —$X^3N_3$, —$O$—$X^3OR^f$, —$O$—$X^3NR^fR^g$, —$O$—$X^3CO_2R^f$, —$O$—$X^3CONR^fR^g$, —$NR^g$—$X^3OR^f$, —$NR^g$—$X^3NR^fR^g$, —$NR^g$—$X^3CO_2R^f$, and —$NR^g$—$X^3CONR^fR^g$, wherein Y is a five or six-membered aryl, heteroaryl or heterocyclic ring, optionally substituted with from one to three substituents selected from the group consisting of halogen, —$OR^f$, —$OC(O)R^f$, —$NR^fR^g$, —$R^h$, —$SR^f$, —$CN$, —$NO_2$, —$CO_2R^f$, —$CONR^fR^g$, —$C(O)R^f$, —$NR^gC(O)$ $R^f$, —$NR^gC(O)_2$ $R^h$, —$S(O)R^h$, —$S(O)_2R^h$, —$NR^fS(O)_2$ $R^h$, —$S(O)_2$ $NR^fR^g$, —$X^3OR^f$, $X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2$ $R^h$, —$X^3NR^f$—$C(O)NR^fR^g$, —$X^3OC(O)R^f$, —$X^3S(O)$ $R^h$, —$X^3S(O)_2R^h$, —$X^3NR^fR^g$, —$X^3NR^fS(O)_2R^h$, —$X^3S(O)_2NR^fR^g$, —$O$—$X^3OR^f$, —$O$—$X^3NR^fR^g$, —$O$—$X^3CO_2R^f$, —$O$—$X^3CONR^fR^g$, —$NR^g$—$X^3OR^f$, —$NR^g$—$X^3NR^fR^g$, —$NR^g$—$X^3CO_2R^f$, and —$NR^g$—$X^3CONR^fR^g$ and wherein each $X^3$ is independently selected from the group consisting of $C_{1-4}$ alkylene, and each $R^f$ and $R^g$ is independently selected from hydrogen, $C_{1-8}$ alkyl, $C_{1-8}$ hydroxyalkyl, $C_{1-8}$ haloalkyl and $C_{3-6}$ cycloalkyl, or when attached to the same nitrogen atom can be combined with the nitrogen atom to form a five or six-membered ring having from 0 to 2 additional heteroatoms as ring members, and each $R^h$ is independently selected from the group consisting of $C_{1-8}$ alkyl, $C_{2-8}$ alkenyl, $C_{2-8}$ alkynyl, $C_{1-8}$ hydroxyalkyl, $C_{1-8}$ haloalkyl and $C_{3-6}$ cycloalkyl;

or when two of $R^5$, $R^6$, $R^7$, $R^8$ and $R^9$, are attached to adjacent ring vertices of $Ar^2$, are optionally combined to form a five or six membered ring having zero, one or two heteroatoms selected from 0 and N as ring members;

or a salt, rotamer or optical isomers thereof.

2. A compound of claim 1, wherein $Ar^2$ is selected from the group consisting of phenyl, pyrazolyl, imidazolyl, triazolyl, tetrazolyl, oxazolyl, isoxazolyl, oxadiazolyl, oxathiadiazolyl, pyrrolyl, thiazolyl, isothiazolyl, benzimidazolyl, benzoxazolyl, benzopyrazolyl, benzotriazolyl, pyrazolo[3,4-b]pyridine, pyrazolo[3,4-d]pyrimidine, imidazo[4,5-b]pyridine, imidazo[1,5-a]pyridine, and pyrrolo[2,3-b]pyridine, each of which is optionally substituted with $R^5$, $R^6$ and $R^7$.

3. A compound of claim 1, wherein $Ar^2$ is selected from the group consisting of pyrazolyl, imidazolyl and triazolyl, each of which is substituted with $R^5$, $R^6$ and $R^7$.

4. A compound of claim 1, wherein $Ar^1$ is selected from the group consisting of phenyl, naphthyl and pyridyl, each of which is substituted with from one to five substituents, $R^3$, $R^{3a}$, $R^{3b}$, $R^4$ and $R^{4a}$; and $Ar^2$ is selected from the group consisting of pyrazolyl, imidazolyl and triazolyl, each of which is substituted with $R^5$, $R^6$ and $R^7$.

5. A compound of claim 1, wherein $Ar^1$ is phenyl, which is substituted with from one to five substituents, $R^3$, $R^{3a}$, $R^{3b}$, $R^4$ and $R^{4a}$, and $Ar^2$ is selected from the group consisting of pyrazolyl, imidazolyl, benzimidazolyl, benzopyrazolyl, pyrazolo[3,4-b]pyridine, pyrazolo[3,4-d]pyrimidine, imidazo[4,5-b]pyridine, imidazo[1,5-a]pyridine, and pyrrolo[2,3-b]pyridine, each of which is optionally substituted with $R^5$, $R^6$ and $R^7$.

6. A compound of claim 1, wherein said compound has the formula:

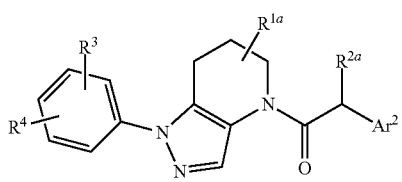

(Ia)

wherein $R^3$ and $R^4$ are independently selected from the group consisting of H, halogen, $-R^e$, $-CN$, and $-SO_2R^e$.

7. A compound of claim 6, wherein $Ar^2$ is a heteroaryl group.

8. A compound of claim 6, wherein $Ar^2$ is a heteroaryl group, optionally substituted and attached to the remainder of the molecule through a nitrogen atom ring vertex.

9. A compound of claim 8, wherein said $Ar^2$ has the formula:

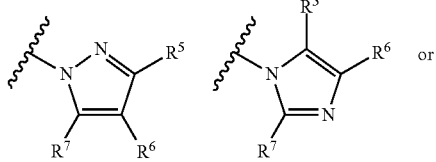

or

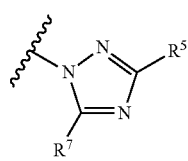

wherein $R^5$, $R^6$, and $R^7$ are independently selected from the group consisting of H, halogen, $-R^h$, $-CN$, $-SO_2R^h$, $-CO_2R^f$, $-CONR^fR^g$, and Y.

10. A compound of claim 9, having the formula:

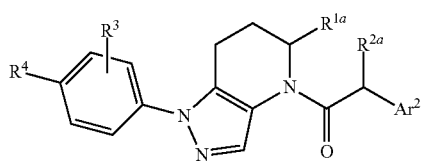

(Ia1)

wherein $R^4$ is selected from the group consisting of F and Cl.

11. A compound of claim 10, wherein Y is selected from the group consisting of pyridyl, pyrimidinyl, imidazolyl, oxazolyl, oxadiazolyl, triazolyl, thiazolyl, imidazolinyl and pyrazolyl.

12. A compound of claim 10, having the formula:

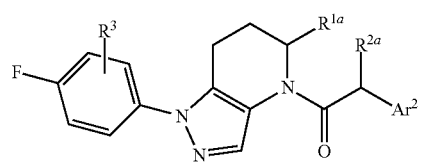

(Ia2)

wherein $R^3$ is selected from the group consisting of H, halogen, $C_{1-8}$ alkyl, $C_{1-8}$ haloalkyl and $C_{1-8}$ alkoxy; $R^{1a}$ and $R^{2a}$ are independently selected from the group consisting of H, $C_{1-8}$ alkyl, $C_{1-8}$ haloalkyl, $C_{1-8}$ alkoxy and $C_{1-8}$ hydroxyalkyl.

13. A compound of claim 1, having the formula:

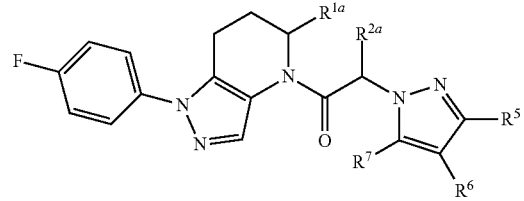

(II)

wherein $R^{1a}$ and $R^{2a}$ are independently selected from the group consisting of H, $C_{1-8}$ alkyl, $C_{1-8}$ haloalkyl, $C_{1-8}$ alkoxy and $C_{1-8}$ hydroxyalkyl; and $R^5$, $R^6$, and $R^7$ are independently selected from the group consisting of H, halogen, $-R^h$, $-CN$, $-SO_2R^h$, $-CO_2R^f$, $-CONR^fR^g$, and Y.

14. A compound of claim 1, having the formula:

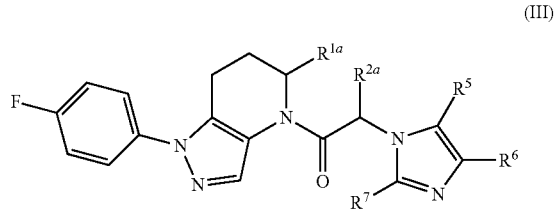

(III)

Where $R^{1a}$ and $R^{2a}$ are independently selected from the group consisting of H, $C_{1-8}$ alkyl, $C_{1-8}$ haloalkyl, $C_{1-8}$ alkoxy and $C_{1-8}$ hydroxyalkyl; and $R^5$, $R^6$, and $R^7$ are independently selected from the group consisting of H, halogen, $-R^h$, $-CN$, $-SO_2R^h$, $-CO_2R^f$, $-CONR^fR^g$, and Y.

15. A compound of claim 1, having the formula:

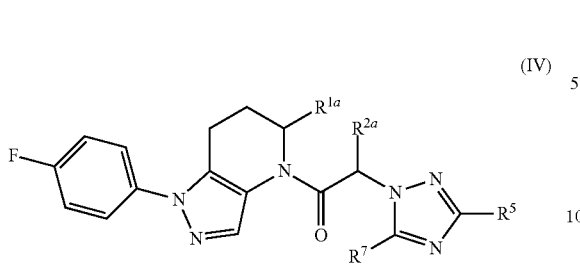

(IV)

wherein $R^{1a}$ and $R^{2a}$ are each independently selected from the group consisting of H, $C_{1-8}$ alkyl, $C_{1-8}$ haloalkyl, $C_{1-8}$ alkoxy, and $C_{1-8}$ hydroxyalkyl; and $R^5$ and $R^7$ are each independently selected from the group consisting of H, halogen, —$R^h$, —CN, —$SO_2R^h$, —$CO_2R^f$, —$CONR^fR^g$, and Y.

16. A compound of claim 1, selected from the group consisting of:

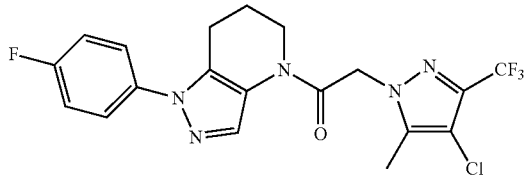

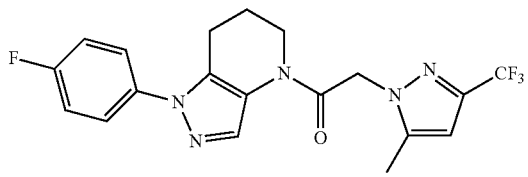

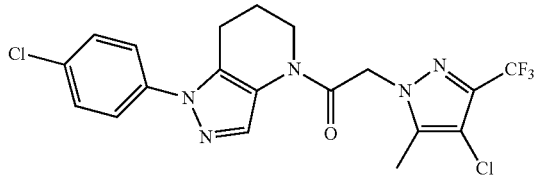

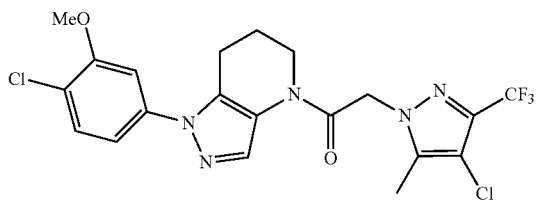

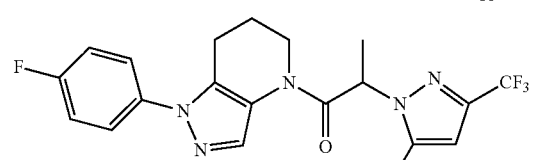

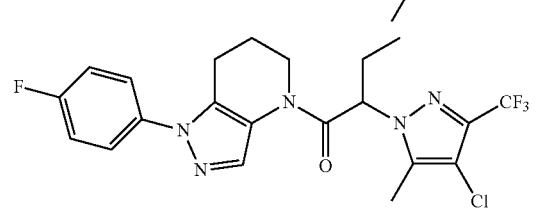

-continued

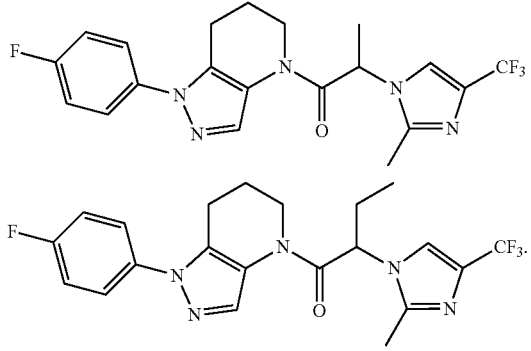

17. A compound of claim 1, wherein said compound is selected from the group consisting of

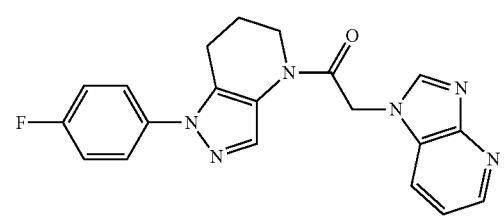

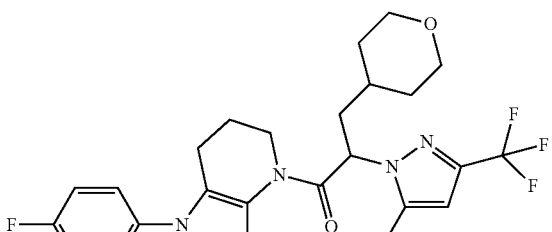

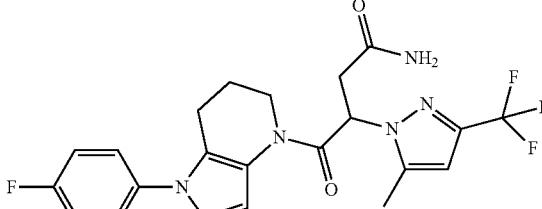

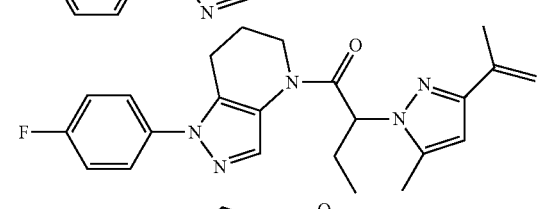

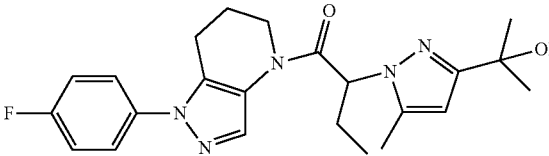

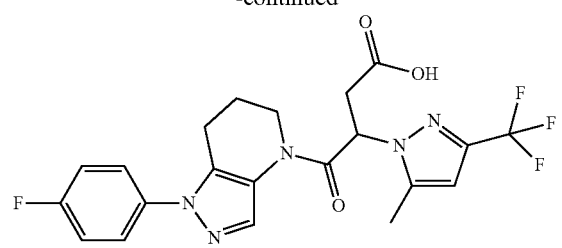
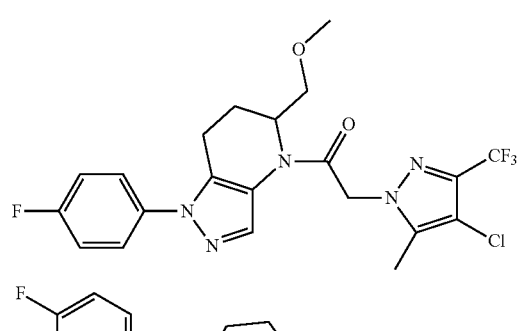
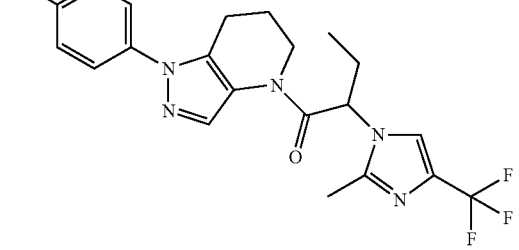
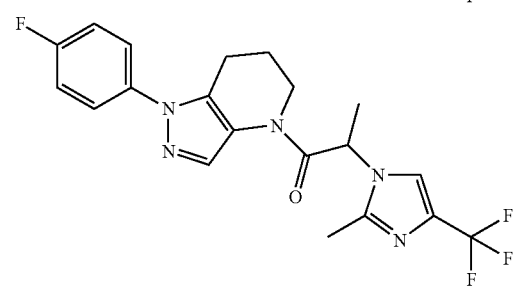
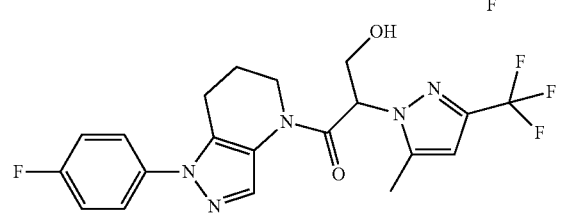
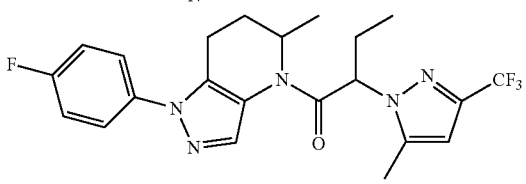
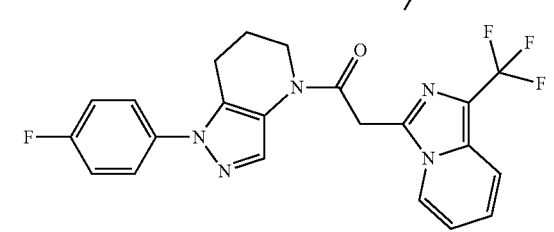
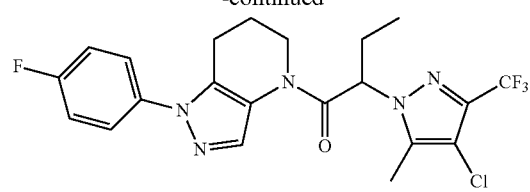
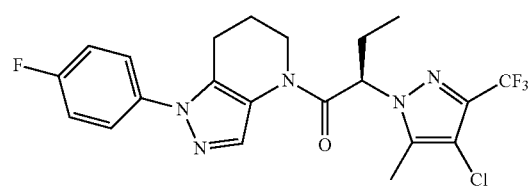
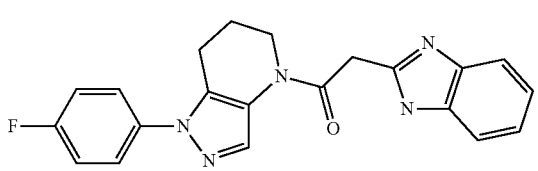
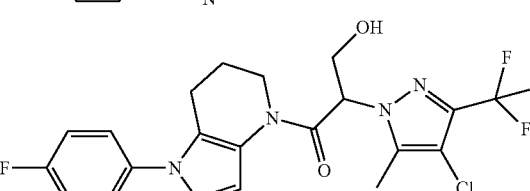
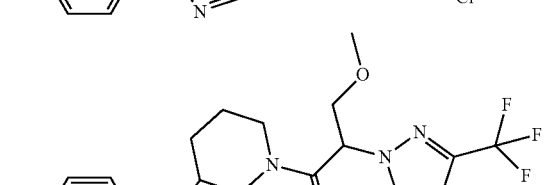
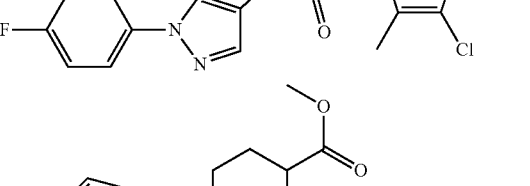
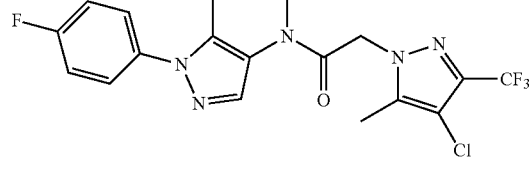
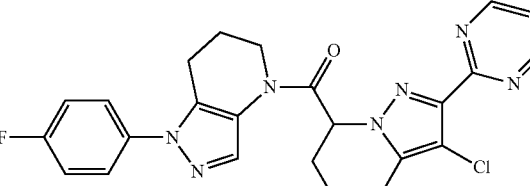
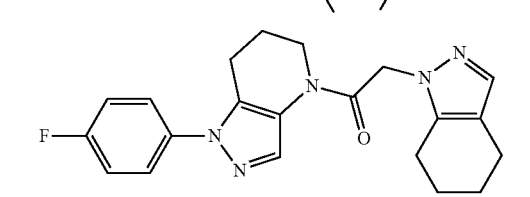

133
-continued
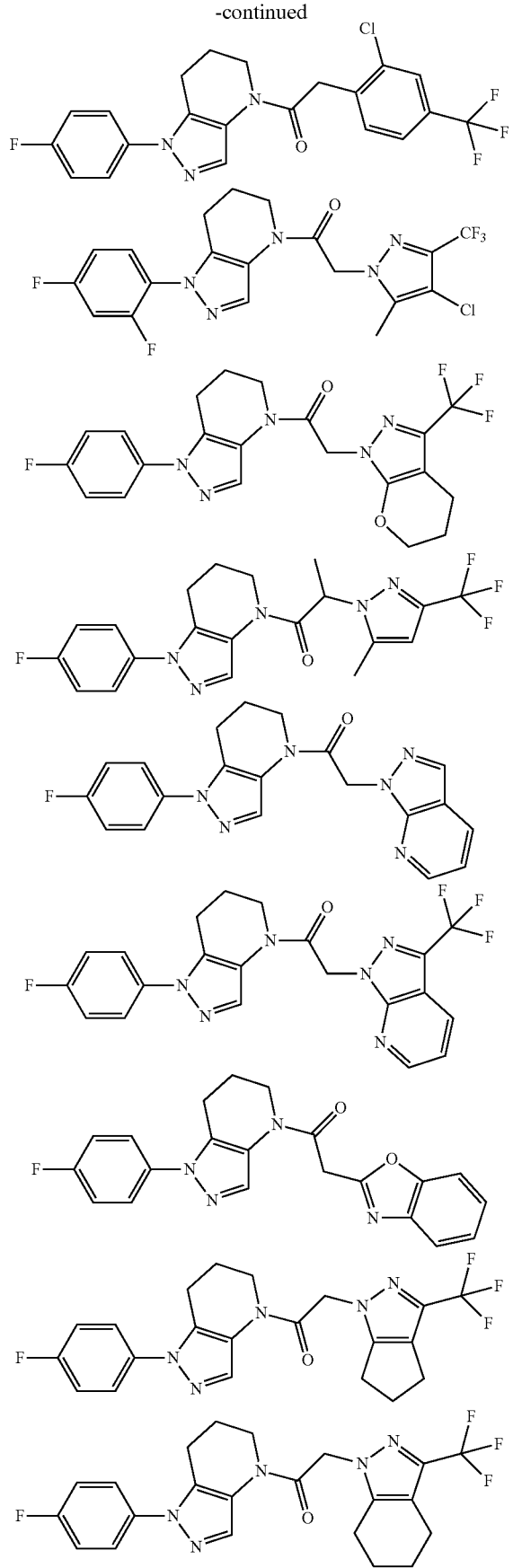
134
-continued
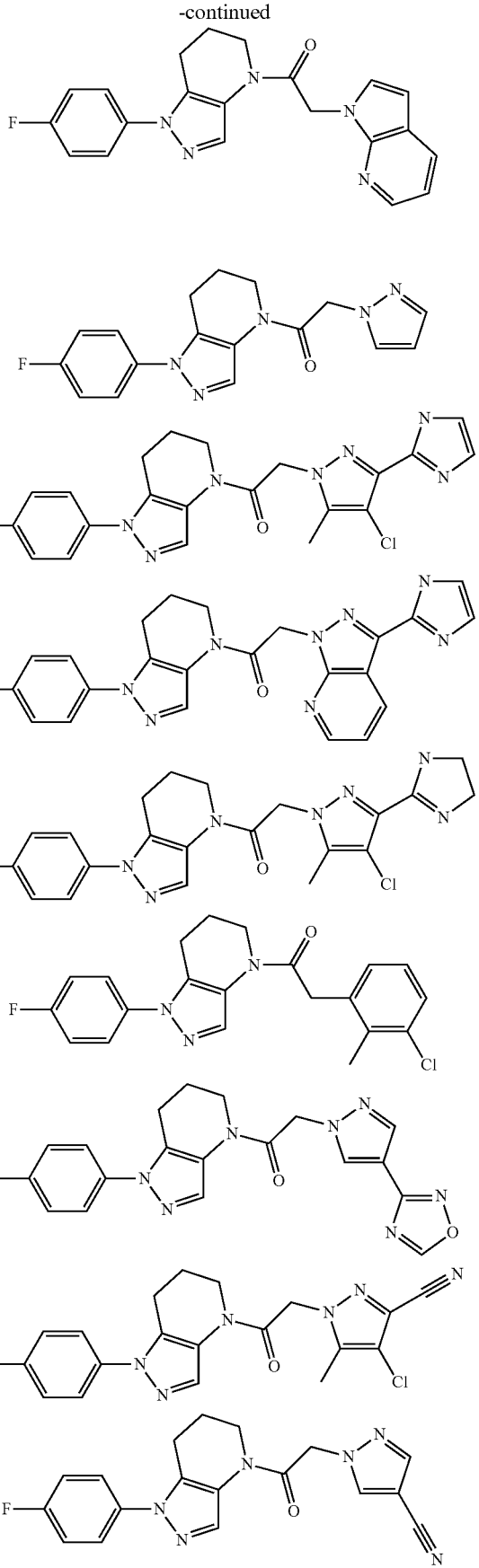

135
-continued
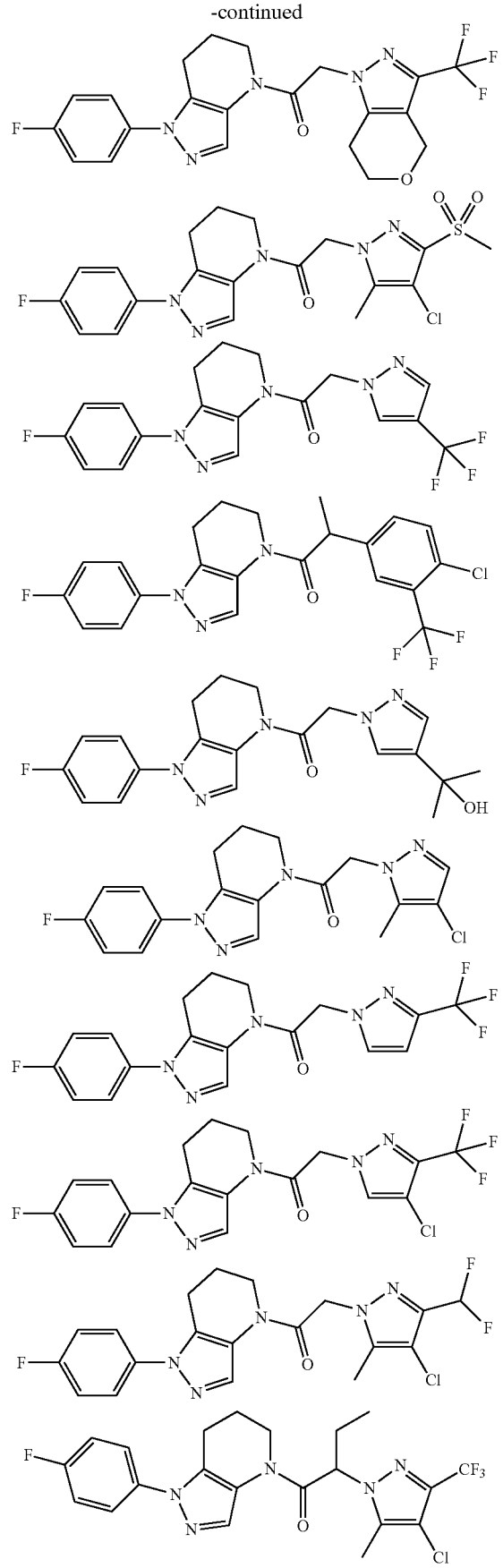
136
-continued
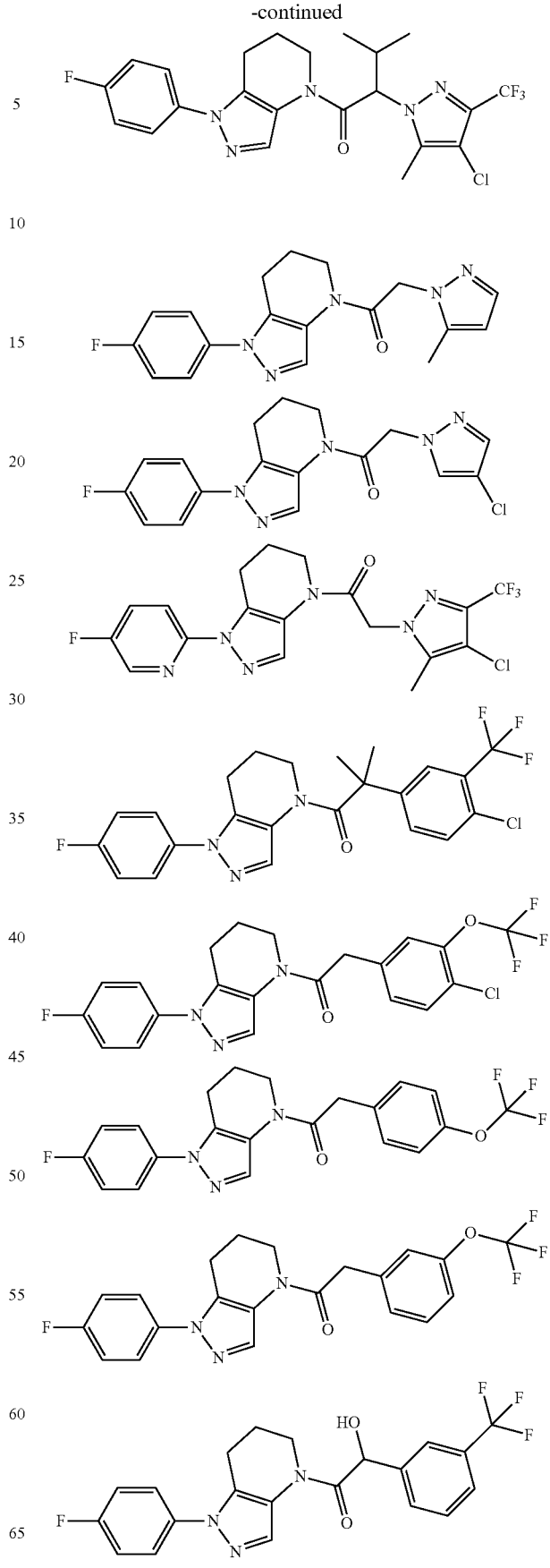

137
-continued
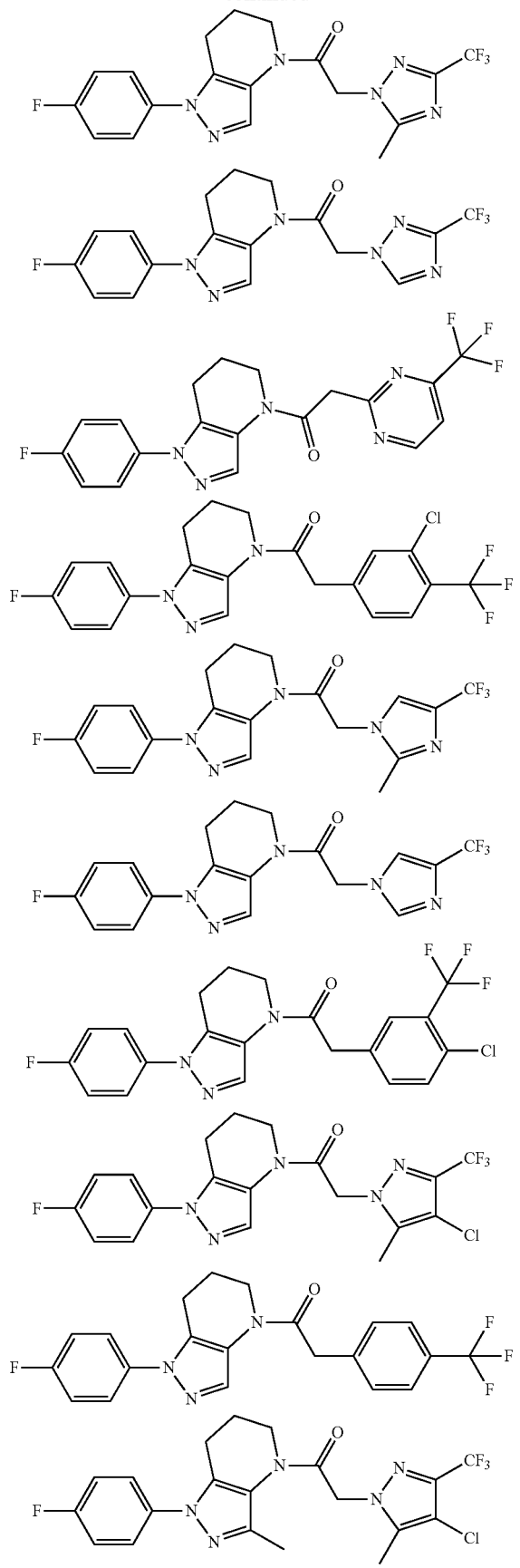
138
-continued
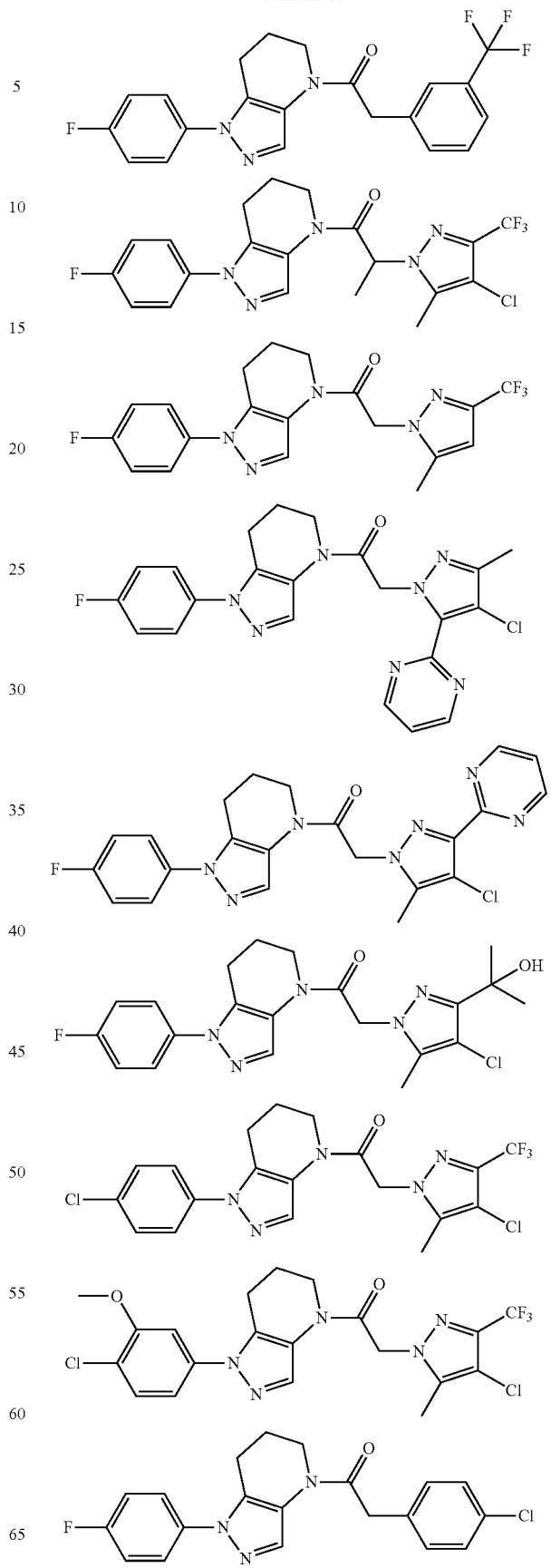

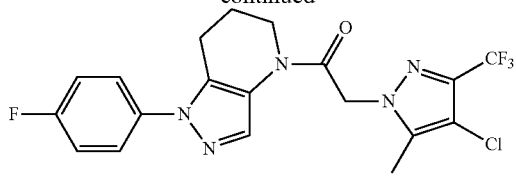
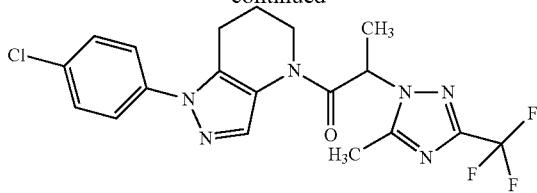
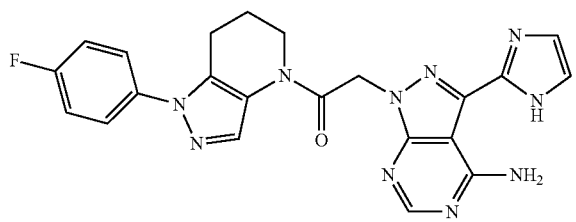
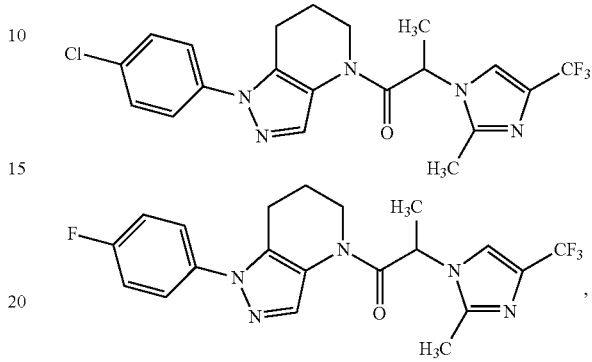
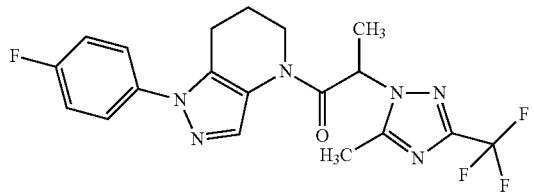
or a pharmaceutically acceptable salt or N-oxide thereof.
18. A pharmaceutical composition comprising a pharmaceutically acceptable excipient or carrier and a compound of claim 1.
19. A pharmaceutical composition of claim 18, wherein said composition is formed as a stent or stent-graft device.
* * * * *